(12) United States Patent
Luo et al.

(10) Patent No.: US 11,993,596 B2
(45) Date of Patent: May 28, 2024

(54) FUSED TRI-CYCLIC COMPOUND AS PDE3/PDE4 DUAL INHIBITOR

(71) Applicant: CHIA TAI TIANQING PHARMACEUTICAL GROUP CO., LTD., Lianyungang (CN)

(72) Inventors: Yunfu Luo, Shanghai (CN); Jianfeng Pan, Shanghai (CN); Guoli Zhang, Shanghai (CN); Sheng Su, Shanghai (CN); Yong Wang, Shanghai (CN); Shuhui Chen, Shanghai (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 653 days.

(21) Appl. No.: 17/259,089

(22) PCT Filed: Jul. 12, 2019

(86) PCT No.: PCT/CN2019/095826
§ 371 (c)(1),
(2) Date: Jan. 8, 2021

(87) PCT Pub. No.: WO2020/011254
PCT Pub. Date: Jan. 16, 2020

(65) Prior Publication Data
US 2021/0323960 A1 Oct. 21, 2021

(30) Foreign Application Priority Data

Jul. 13, 2018 (CN) .......................... 201810772374.3

(51) Int. Cl.
| C07D 471/04 | (2006.01) |
| A61P 11/00 | (2006.01) |
| C07D 487/04 | (2006.01) |
| C07D 498/04 | (2006.01) |

(52) U.S. Cl.
CPC ............ *C07D 471/04* (2013.01); *A61P 11/00* (2018.01); *C07D 487/04* (2013.01); *C07D 498/04* (2013.01)

(58) Field of Classification Search
CPC .................................................. C07D 471/04
See application file for complete search history.

(56) References Cited

U.S. PATENT DOCUMENTS

| 4,482,556 | A | 11/1984 | Hoechst |
| 9,062,047 | B2 | 6/2015 | Walker |
| 2012/0302533 | A1 | 11/2012 | Oxford |

FOREIGN PATENT DOCUMENTS

| CN | 1348453 A | 5/2002 |
| EP | 0124893 A2 | 11/1984 |
| GB | 1597717 | † 9/1981 |
| GB | 1597717 A | 9/1981 |
| RU | 2577541 C2 | 9/2014 |
| WO | 00/58308 A1 | † 10/2000 |
| WO | WO 2000/58308 A1 | 10/2000 |

OTHER PUBLICATIONS

Kienzle et al., Die synthese von 6,7-dihydro-2H-pyrimido[6,1-a]isochinolin-4(3H)-onen und analogen verbindungen und deren wirkung als blutplattchenaggregationshemmer. Helvetica chimica acta, 1986, vol. 69, No. 7, pp. 1671-1680.
Banner et al., "Dual PDE3/4 inhibitors as therapeutic agents for chronic obstructive pulmonary disease", British Journal of Pharmacology (2009), 157, pp. 892-906.
Dundee et al., "Midazolam A Review of its Pharmacological Properties and Therapeutic Use", Drugs 28(6): 1984, pp. 519-543.
Meanwell, "Synopsis of Some Recent Tactical Application of Bioisosteres in Drug Design", J. Med. Chem. 2011, 54(8), pp. 2529-2591.
Subramanian et al., "Design, Synthesis, and Biological Evaluation of Tetrazole Analogs of Cl-Amidine as Protein Arginine Deiminase Inhibitors", J. Med. Chem., 2015, 58(3), pp. 1337-1344.
Bonandi et al., "The 1,2,3-triazole ring as a bioisostere in medicinal chemistry", Drug Discovery Today, 2017, 22(10), pp. 1572-1581.
Bostrom et al., "Oxadiazoles in Medicinal Chemistry", J. Med. Chem., 2012, 55(5), pp. 1817-1830.
International Search Report in International Patent Application No. PCT/CN2019/095826, dated Oct. 15, 2019 (5 pages).
Meanwell, Synopsis of Some Recent Tactical Application of Bioisosteres in Drug Design, J. Med. Chem., 2011, 54(8), 2529-2591.†
Subramanian et al., Design, Synthesis, and Biological Evaluation of Tetrazole Analogs of CI-Amidine as Protein Arginine Deiminase Inhibitors, J. Med. Chem., 2015, 58(3), 1337-1344.†

(Continued)

*Primary Examiner* — Golam M Shameem
(74) *Attorney, Agent, or Firm* — NIXON PEABODY LLP

(57) ABSTRACT

Provided is a fused tri-cyclic compound as PDE3/PDE4 dual inhibitor, and a use thereof in the preparation of drugs for PDE3/PDE4 associated diseases, particularly in medicinal functions such as chronic obstructive pulmonary disease (COPD). Provided are specifically a compound of formula (I) and a pharmaceutically acceptable salt thereof.

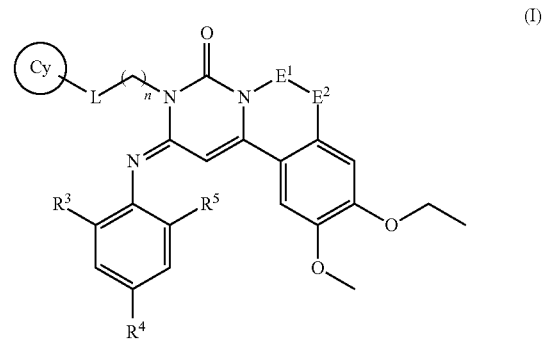

(I)

21 Claims, 1 Drawing Sheet

(56) References Cited

OTHER PUBLICATIONS

Bonandi et al., The 1,2,3-triazole ring as a bioisostere in medicinal chemistry, Drug Discovery Today, 2017, 22(10), 1572-1581.†
Bostrom et al., Oxadiazoles in Medicinal Chemistry, J. Med. Chem., 2012, 55(5), 1817-1830.†

† cited by third party

FUSED TRI-CYCLIC COMPOUND AS PDE3/PDE4 DUAL INHIBITOR

CROSS-REFERENCE TO RELATED APPLICATIONS

The present application is a U.S. national stage of PCT/CN2019/095826, filed on Jul. 12, 2019, which claims the benefit and priority to Chinese Patent No. 201810772374.3 filed with the National Intellectual Property Administration, PRC on Jul. 13, 2018, which are incorporated herein by reference in their entireties.

TECHNICAL FIELD

The present application relates to a tricyclic compound as a PDE3/PDE4 dual inhibitor, a preparation method thereof, a pharmaceutical composition containing the compound, and use thereof in treating a disease related to PDE3/PDE4, in particular chronic obstructive pulmonary disease (COPD).

BACKGROUND

Phosphodiesterases (PDEs) are a superfamily of enzyme systems and comprise 11 families, each of which is involved in different signaling and regulates different physiological processes. Among them, PDE3 is a major phosphodiesterase in human airway smooth muscle (ASM), and inhibition of PDE3 increases intracellular cAMP concentration and thus slackening bronchial smooth muscle. PDE4 plays a major regulatory role in the expression of proinflammatory and anti-inflammatory mediators, and a PDE4 inhibitor can inhibit the release of harmful mediators from inflammatory cells. Thus, in theory, an inhibitor that inhibits both PDE3 and PDE4 would have both the bronchodilation of a beta-adrenoreceptor agonist and the anti-inflammatory action of an inhaled glucocorticoid. The complementation of dual targeting functions is theoretically more effective than single targeting, and the treatment effect which can be achieved only by combined medication at present is achieved by a single medicament, thus the defect that the physicochemical properties of the ingredients of medicaments used in the combined medication cannot be completely matched is eliminated, the administration mode is simplified, and convenient determination of administration dosage is realized.

It has been reported by Victoria Boswell et al., *J. Pharmaco. Expert. Therap.* 2006, 318, 840-848 and WO200005830 that compounds RPL554 and RPL565 have long-acting bronchodilation and anti-inflammatory action and physicochemical properties like poor solubility and high plasma clearance, and they are suitable for inhalation administration. However, data also show that their inhibitory activity against PDE4 is unsatisfactory, and the anti-inflammatory effect is not ideal, either. Therefore, there is a need to develop a compound having good inhibitory activity against PDE3/4.

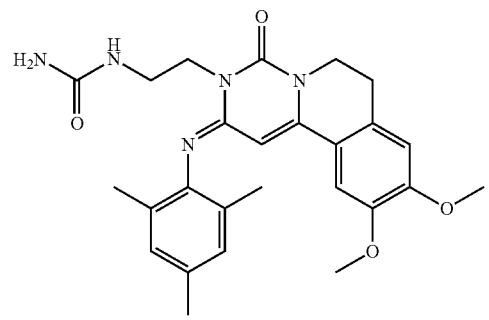

RPL554

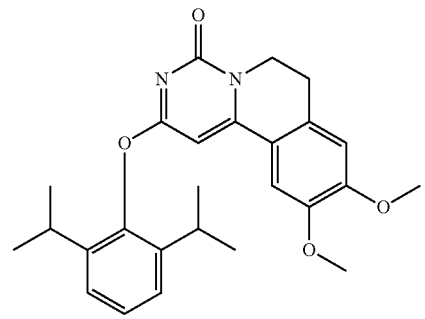

RPL565

SUMMARY

In one aspect, the present application provides a compound of formula (I), an isomer thereof or a pharmaceutically acceptable salt thereof,

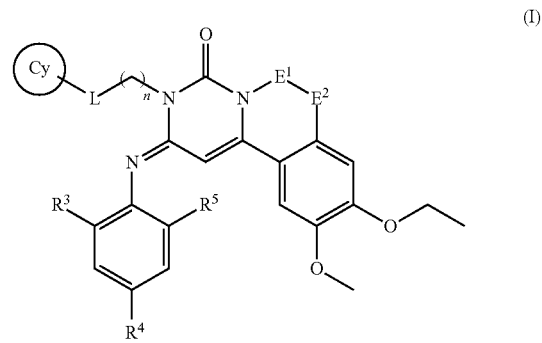

(I)

wherein, ring Cy is selected from the group consisting of 5 membered heterocyclyl and 5 membered heteroaryl, wherein the 5 membered heterocyclyl or 5 membered heteroaryl is optionally substituted by one or more of the following groups: amino, hydroxy, =O, halogen, cyano, $C_{1-12}$ alkyl, —C(O)NH$_2$, —C(O)NH($C_{1-6}$ alkyl), —C(O)N($C_{1-6}$ alkyl)$_2$, —COOH, —C(O)O ($C_{1-6}$ alkyl) or $C_{1-12}$ alkoxy, wherein the $C_{1-12}$ alkyl or $C_{1-12}$ alkoxy is optionally substituted by one or more groups selected from the group consisting of halogen, amino and hydroxy;

ring atoms of the ring Cy comprise at least one nitrogen atom;

L is selected from the group consisting of —N(R$^6$)—, —N(R$^6$)C(O)—, —C(O)N(R$^6$)—, —O—, —S—, —OC(O)—, —C(O)O—, —CH$_2$N(R$^6$)C(O)—, —CH$_2$C(O)N(R$^6$)—, —S(O)$_2$NH—, —NHS(O)$_2$— and a single bond;

n is 1,2,3 or 4;

E$^1$ is —(CH$_2$)$_m$—, wherein m is 1, 2 or 3;

E$^2$ is selected from the group consisting of —O—, —NH—, —S— and a single bond;

R$^3$, R$^4$ and R$^5$ are each independently selected from the group consisting of hydrogen, halogen and C$_{1-6}$ alkyl, wherein the C$_{1-6}$ alkyl is optionally substituted by one or more groups selected from the group consisting of halogen, amino and hydroxy; and each R$^6$ is independently selected from the group consisting of hydrogen, hydroxy and C$_{1-3}$ alkyl, wherein the C$_{1-3}$ alkyl is optionally substituted by one or more groups selected from the group consisting of halogen, amino and hydroxy.

In some embodiments, ring Cy is selected from the group consisting of 5 membered heterocyclyl and 5 membered heteroaryl, wherein the 5 membered heteroaryl or 5 membered heteroaryl is optionally substituted by one or more of the following groups: amino, hydroxy, =O, halogen, cyano, C$_{1-6}$ alkyl, —C(O)NH$_2$, —C(O)NH(C$_{1-3}$ alkyl), —C(O)N(C$_{1-3}$ alkyl)$_2$, —COOH, —C(O)O(C$_{1-3}$ alkyl), C$_{1-6}$ alkoxy, or C$_{1-6}$ alkyl substituted by one or more halogens; in some embodiments, ring Cy is selected from the group consisting of 5 membered heterocyclyl and 5 membered heteroaryl, wherein the 5 membered heteroaryl is optionally substituted by one or more of the following groups: amino, hydroxy, halogen, cyano, C$_{1-6}$ alkyl, —C(O)NH$_2$, —C(O)NH(C$_{1-3}$ alkyl), —C(O)N(C$_{1-3}$ alkyl)$_2$, —COOH, —C(O)O(C$_{1-3}$ alkyl), C$_{1-6}$ alkoxy, or C$_{1-6}$ alkyl substituted by one or more halogens, wherein the 5 membered heterocyclyl is optionally substituted by one or more =O; in some embodiments, ring Cy is selected from the group consisting of oxazolidin-2-one, imidazolyl, pyrazolyl, oxazolyl, triazolyl, oxadiazolyl, tetrazolyl, thiadiazolyl and isoxazolyl, wherein the imidazolyl, pyrazolyl, oxazolyl, triazolyl, oxadiazolyl, tetrazolyl, thiadiazolyl or isoxazolyl is optionally substituted by one or more of the following groups: amino, hydroxy, halogen, cyano, C$_{1-6}$ alkyl, —C(O)NH$_2$, —C(O)NH(C$_{1-3}$ alkyl), —C(O)N(C$_{1-3}$ alkyl)$_2$, —COOH, —C(O)O(C$_{1-3}$ alkyl), C$_{1-6}$ alkoxy, or C$_{1-6}$ alkyl substituted by one or more halogens.

In some embodiments, ring Cy is 5 membered heteroaryl, wherein the 5 membered heteroaryl is optionally substituted by one or more of the following groups: amino, hydroxy, fluoro, chloro, bromo, iodo, cyano, C$_{1-3}$ alkyl, —C(O)NH$_2$, —C(O)O(C$_{1-3}$ alkyl), C$_{1-3}$ alkoxy, or C$_{1-3}$ alkyl substituted by one or more halogens; in some embodiments, ring Cy is selected from the group consisting of imidazolyl, pyrazolyl, oxazolyl, triazolyl, oxadiazolyl, tetrazolyl, thiadiazolyl and isoxazolyl, wherein the imidazolyl, pyrazolyl, oxazolyl, triazolyl, oxadiazolyl, tetrazolyl, thiadiazolyl or isoxazolyl is optionally substituted by one or more of the following groups: amino, hydroxy, fluoro, chloro, bromo, iodo, cyano, C$_{1-3}$ alkyl, —C(O)NH$_2$, —C(O)O(C$_{1-3}$ alkyl), C$_{1-3}$ alkoxy, or C$_{1-3}$ alkyl substituted by one or more halogens.

In some embodiments, ring Cy is 5-membered heteroaryl, wherein the 5-membered heteroaryl is optionally substituted by one or more of the following groups: amino, hydroxy, fluoro, chloro, cyano, methyl, —C(O)NH$_2$, —C(O)OCH$_3$, methoxy or trifluoromethyl; in some embodiments, ring Cy is selected from the group consisting of imidazolyl, pyrazolyl, oxazolyl, triazolyl, oxadiazolyl, tetrazolyl, thiadiazolyl and isoxazolyl, wherein the imidazolyl, pyrazolyl, oxazolyl, triazolyl, oxadiazolyl, tetrazolyl, thiadiazolyl or isoxazolyl is optionally substituted by one or more of the following groups: amino, hydroxy, fluoro, chloro, cyano, methyl, —C(O)NH$_2$, —C(O)OCH$_3$, methoxy or trifluoromethyl.

In some embodiments, ring Cy is selected from the group consisting of structural units

wherein,

╱╱ represents a single bond or double bond;

T$^1$, T$^2$, T$^3$ and T$^4$ are each independently selected from the group consisting of C=O, C(R$^1$), C(R$^1$)$_2$, O, N(R$^2$), N and S;

each R$^1$ is independently selected from the group consisting of hydrogen, amino, hydroxy, halogen, cyano, C$_{1-12}$ alkyl, —C(O)NH$_2$, —C(O)NH(C$_{1-6}$ alkyl), —C(O)N(C$_{1-6}$ alkyl)$_2$, —COOH, —C(O)O(C$_{1-6}$ alkyl) and C$_{1-12}$ alkoxy, wherein the C$_{1-12}$ alkyl or C$_{1-12}$ alkoxy is optionally substituted by one or more groups selected from the group consisting of halogen, amino and hydroxy; and each R$^2$ is independently selected from the group consisting of hydrogen, hydroxy and C$_{1-3}$ alkyl, wherein the C$_{1-3}$ alkyl is optionally substituted by one or more groups selected from the group consisting of halogen, amino and hydroxy.

In some embodiments, ring Cy is the structural unit

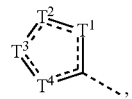

wherein,

╱╱ represents a single bond or double bond;

T$^1$, T$^2$, T$^3$ and T$^4$ are each independently selected from the group consisting of C(R$^1$), C(R$^1$)$_2$, O, N(R$^2$), N and S;

each R$^1$ is independently selected from the group consisting of hydrogen, amino, hydroxy, halogen, cyano, C$_{1-12}$ alkyl, —C(O)NH$_2$, —C(O)NH(C$_{1-6}$ alkyl), —C(O)N(C$_{1-6}$ alkyl)$_2$, —COOH, —C(O)O(C$_{1-6}$ alkyl) and C$_{1-12}$ alkoxy, wherein the C$_{1-12}$ alkyl or C$_{1-12}$ alkoxy is optionally substituted by one or more groups selected from the group consisting of halogen, amino and hydroxy; and each R$^2$ is independently selected from the group consisting of hydrogen, hydroxy and C$_{1-3}$ alkyl, wherein the C$_{1-3}$ alkyl is optionally substituted by one or more groups selected from the group consisting of halogen, amino and hydroxy. In some embodiments, ring Cy is the structural unit

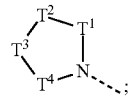

wherein, $T^1$, $T^2$, $T^3$ and $T^4$ are each independently selected from the group consisting of C=O, $C(R^1)_2$, O, $N(R^2)$ and S;

each $R^1$ is independently selected from the group consisting of hydrogen, amino, hydroxy, halogen, cyano, $C_{1-12}$ alkyl, —C(O)NH$_2$, —C(O)NH($C_{1-6}$ alkyl), —C(O)N($C_{1-6}$ alkyl)$_2$, —COOH, —C(O)O($C_{1-6}$ alkyl) and $C_{1-12}$ alkoxy, wherein the $C_{1-12}$ alkyl or $C_{1-12}$ alkoxy is optionally substituted by one or more groups selected from the group consisting of halogen, amino and hydroxy; and each $R^2$ is independently selected from the group consisting of hydrogen, hydroxy and $C_{1-3}$ alkyl, wherein the $C_{1-3}$ alkyl is optionally substituted by one or more groups selected from the group consisting of halogen, amino and hydroxy. In some embodiments, $T^1$ is selected from the group consisting of $C(R^1)$, $C(R^1)_2$ and N, and $T^2$, $T^3$ and $T^4$ are each independently selected from the group consisting of C=O, $C(R^1)$, $C(R^1)_2$, O, $N(R^2)$, N and S.

In some embodiments, $T^1$ is selected from the group consisting of $C(R^1)$ and N, and $T^2$, $T^3$ and $T^4$ are each independently selected from the group consisting of C=O, $C(R^1)$, O, $N(R^2)$, N and S.

In some embodiments, $T^1$ is selected from the group consisting of $C(R^1)$ and N, and $T^2$, $T^3$ and $T^4$ are each independently selected from the group consisting of $C(R^1)$, O, $N(R^2)$, N and S.

In some embodiments, in the structural unit

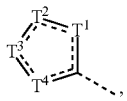

$T^1$ is selected from the group consisting of $C(R^1)$ and N, and $T^2$, $T^3$ and $T^4$ are each independently selected from the group consisting of $C(R^1)$, O, $N(R^2)$ and N.

In some embodiments, in the structural unit

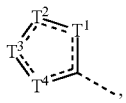

at least one of $T^1$, $T^2$, $T^3$, and $T^4$ is selected from the group consisting of $N(R^2)$ and N.

In some embodiments, in the structural unit

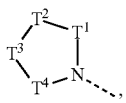

$T^1$ is $C(R^1)_2$, and $T^2$, $T^3$ and $T^4$ are each independently selected from the group consisting of C=O, $C(R^1)_2$ and O.

In some embodiments, each $R^1$ is independently selected from the group consisting of hydrogen, amino, hydroxy, halogen, cyano, $C_{1-6}$ alkyl, —C(O)NH$_2$, —C(O)NH($C_{1-3}$ alkyl), —C(O)N($C_{1-3}$ alkyl)$_2$, —COOH, —C(O)O($C_{1-3}$ alkyl) and $C_{1-6}$ alkoxy, wherein the $C_{1-6}$ alkyl or $C_{1-6}$ alkoxy is optionally substituted by one or more groups selected from the group consisting of halogen, amino and hydroxy; in some embodiments, each $R^1$ is independently selected from the group consisting of hydrogen, amino, hydroxy, halogen, cyano, $C_{1-6}$ alkyl, —C(O)NH$_2$, —C(O)O($C_{1-3}$ alkyl) and $C_{1-3}$ alkoxy, wherein the $C_{1-6}$ alkyl or $C_{1-3}$ alkoxy is optionally substituted by one or more groups selected from the group consisting of halogen, amino and hydroxy; in some embodiments, each $R^1$ is independently selected from the group consisting of hydrogen, amino, hydroxy, halogen, cyano, $C_{1-6}$ alkyl, —C(O)NH$_2$, —C(O)O($C_{1-3}$ alkyl) and $C_{1-3}$ alkoxy, wherein the $C_{1-6}$ alkyl is optionally substituted by one or more groups selected from the group consisting of halogen, amino and hydroxy; in some embodiments, each $R^1$ is independently selected from the group consisting of hydrogen, amino, hydroxy, halogen, cyano, $C_{1-3}$ alkyl, —C(O)NH$_2$, —C(O)OCH$_3$ and $C_{1-3}$ alkoxy, wherein the $C_{1-3}$ alkyl or $C_{1-3}$ alkoxy is optionally substituted by one or more groups selected from the group consisting of halogen, amino and hydroxy; in some embodiments, each $R^1$ is independently selected from hydrogen, amino, hydroxy, halogen, cyano, $C_{1-3}$ alkyl, —C(O)NH$_2$, —C(O)OCH$_3$ and $C_{1-3}$ alkoxy, wherein the $C_{1-3}$ alkyl is optionally substituted by one or more groups selected from the group consisting of halogen, amino and hydroxy; in some embodiments, each $R^1$ is independently selected from the group consisting of hydrogen, amino, hydroxy, halogen, cyano, $C_{1-3}$ alkyl, —C(O)NH$_2$, —C(O)OCH$_3$ and $C_{1-3}$ alkoxy, wherein the $C_{1-3}$ alkyl is optionally substituted by 1, 2, or 3 halogens, amino, or hydroxy; in some embodiments, each $R^1$ is independently selected from the group consisting of hydrogen, amino, hydroxy, fluoro, chloro, cyano, methyl, —C(O)NH$_2$, —C(O)OCH$_3$, methoxy and trifluoromethyl.

In some embodiments, each $R^1$ is independently selected from the group consisting of hydrogen, amino, hydroxy, $C_{1-6}$ alkyl and $C_{1-6}$ alkoxy, wherein the $C_{1-6}$ alkyl or $C_{1-6}$ alkoxy is optionally substituted by one or more groups selected from the group consisting of halogen, amino and hydroxy; in some embodiments, each $R^1$ is independently selected from the group consisting of hydrogen, amino, hydroxy, $C_{1-3}$ alkyl and $C_{1-3}$ alkoxy; in some embodiments, each $R^1$ is independently selected from the group consisting of hydrogen, amino, hydroxy, methyl and methoxy.

In some embodiments, each $R^2$ is independently selected from the group consisting of hydrogen, hydroxy and $C_{1-3}$ alkyl, wherein the $C_{1-3}$ alkyl is optionally substituted by one or more halogens, amino or hydroxy; in some embodiments, each $R^2$ is independently selected from the group consisting of hydrogen, hydroxy and $C_{1-3}$ alkyl, wherein the $C_{1-3}$ alkyl is optionally substituted by 1, 2 or 3 halogens, amino or hydroxy; in some embodiments, each $R^2$ is independently selected from the group consisting of hydrogen, hydroxy and methyl; in some embodiments, each $R^2$ is independently selected from the group consisting of hydrogen and methyl.

In some embodiments, the structural unit

preferably, the structural unit is selected from the group consisting of

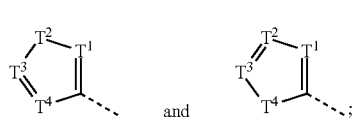

more preferably, the structural unit is selected from the group consisting of
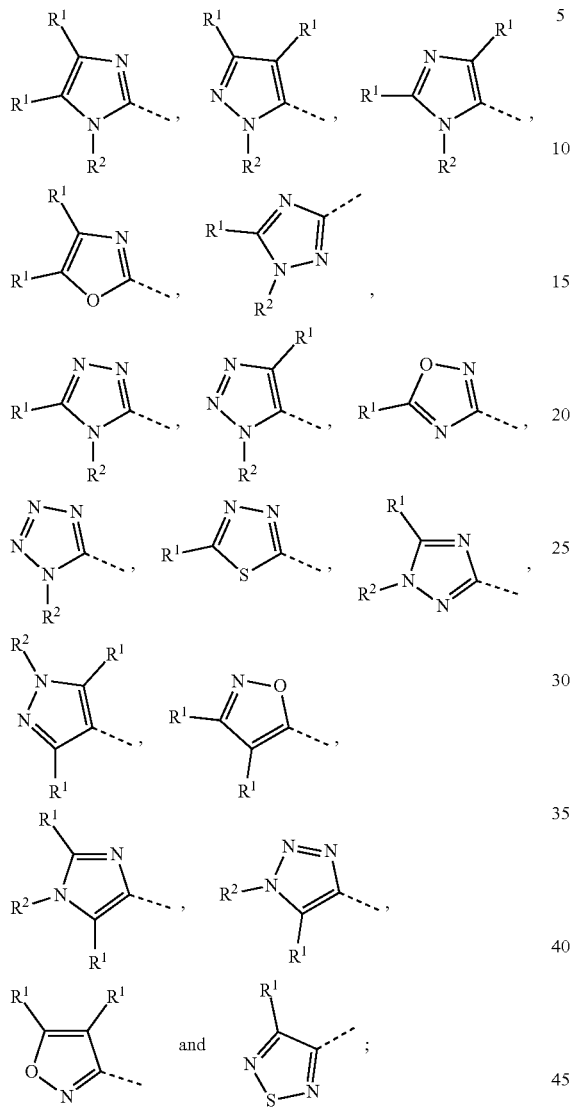
even more preferably, the structural unit is selected from the group consisting of
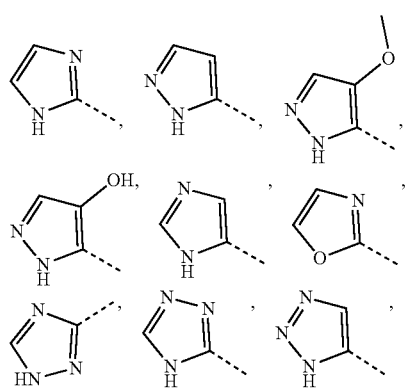
-continued
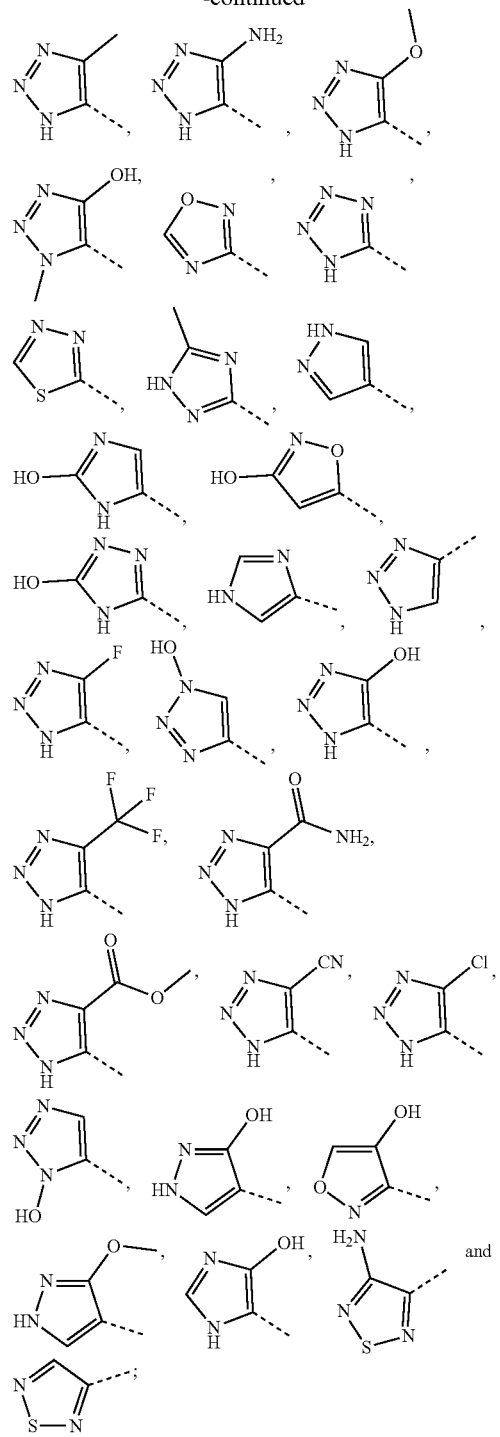
and still more preferably, the structural unit is selected from the group consisting of
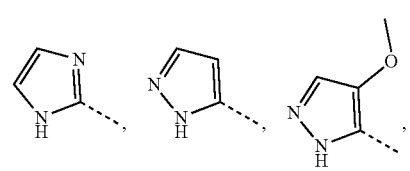

-continued

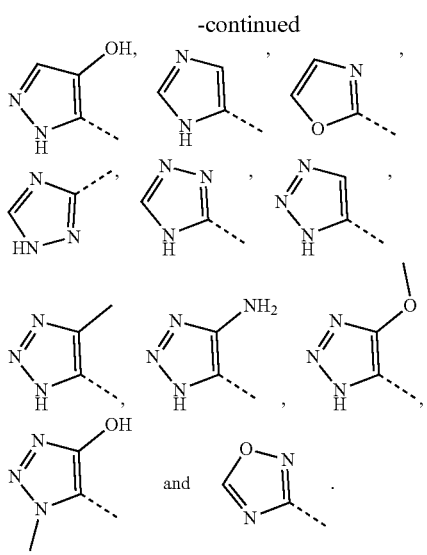

In some embodiments, the structural unit

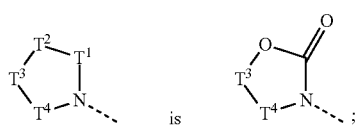

preferably, the structural unit is

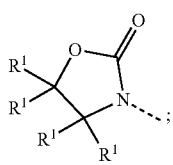

and more preferably, the structural unit is

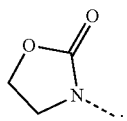

In some embodiments, L is selected from the group consisting of —N(R⁶)—, —N(R⁶)C(O)—, —C(O)N(R⁶)—, —CH₂N(R⁶)C(O)—, —CH₂C(O)N(R⁶)—, —S(O)₂NH—, —NHS(O)₂— or a single bond; in some embodiments, L is selected from the group consisting of —N(R⁶)—, —N(R⁶)C(O)—, —C(O)N(R⁶)—, —CH₂N(R⁶)C(O)—, —S(O)₂NH— and a single bond; in some embodiments, L is selected from the group consisting of —N(R⁶)—, —N(R⁶)C(O)—, —C(O)N(R⁶)— and —S(O)₂NH—; in some embodiments, L is selected from the group consisting of —N(R⁶)—, —N(R⁶)C(O)— and —C(O)N(R⁶)—; in some embodiments, L is selected from the group consisting of —NH—, —NHC(O)—, —C(O)NH—, —C(O)N(OH)—, —S(O)₂NH— and a single bond; in some embodiments, L is selected from the group consisting of —NH—, —NHC(O)—, —C(O)NH— and —C(O)N(OH)—.

In some embodiments, n is selected from the group consisting of 1, 2 and 3; in some embodiments, n is selected from the group consisting of 1 and 2; in some embodiments, n is 2.

In some embodiments, the structural unit

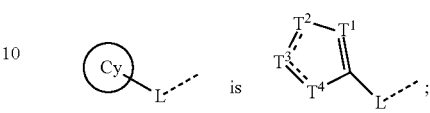

preferably, the structural unit is selected from the group consisting of

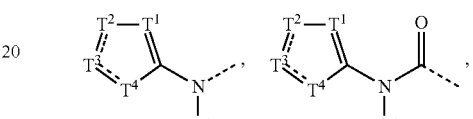

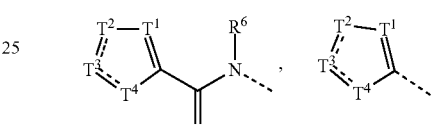

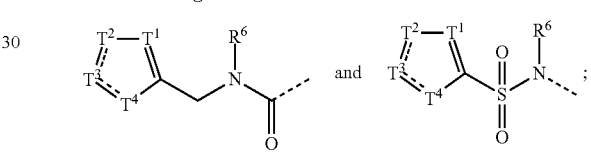

more preferably, the structural unit is selected from the group consisting of

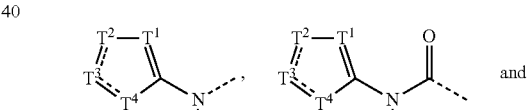

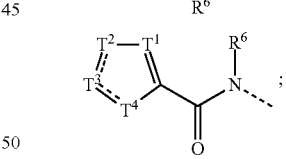

even more preferably, the structural unit is selected from the group consisting of

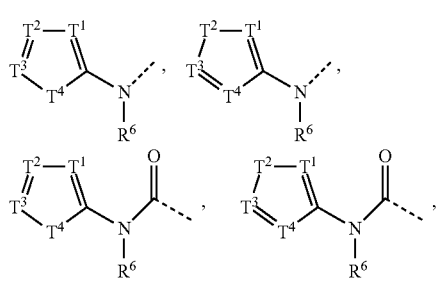

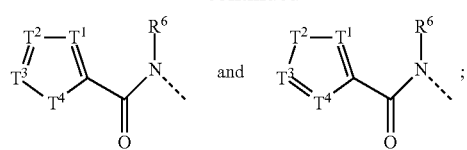 and 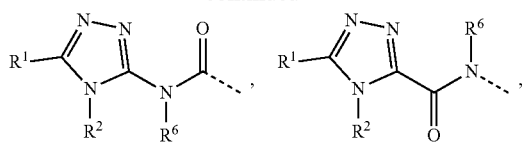
still more preferably, the structural unit is selected from the group consisting of
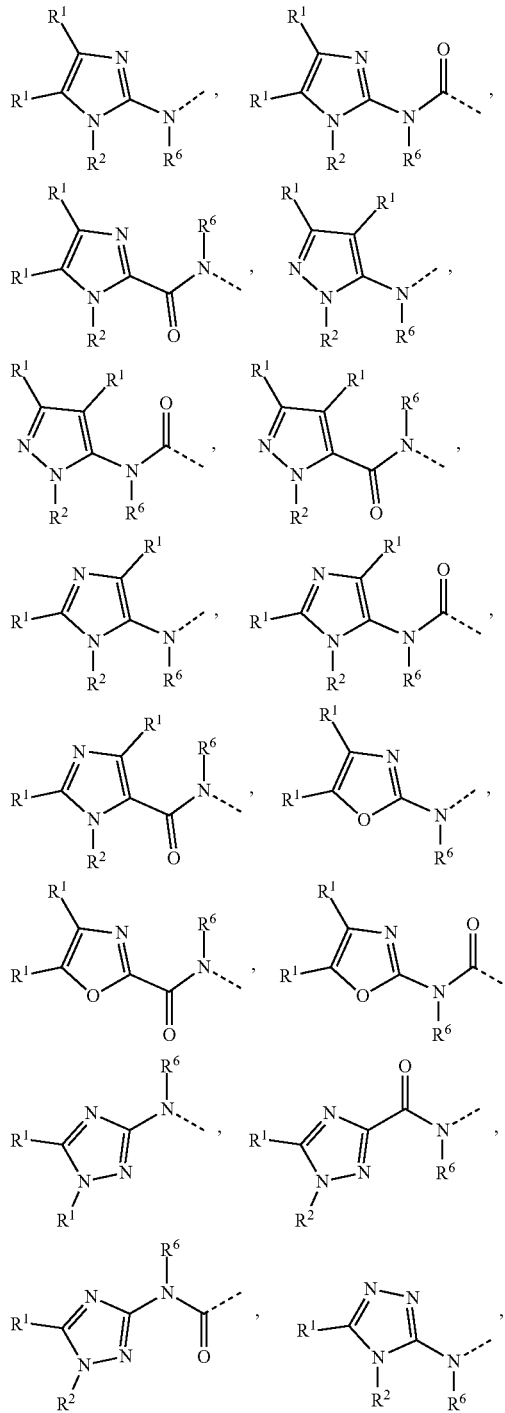
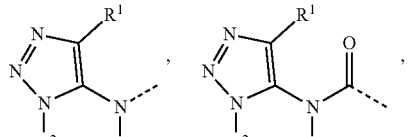
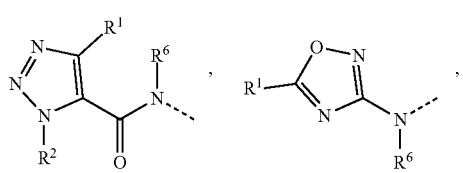
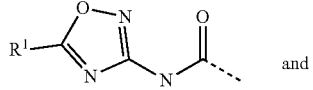
and
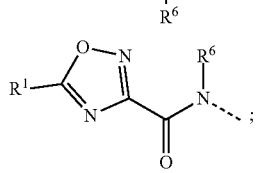
and still even more preferably, the structural unit is selected from the group consisting of
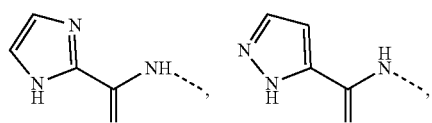
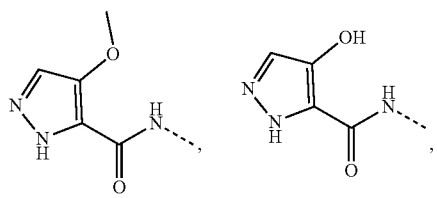
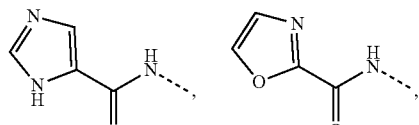
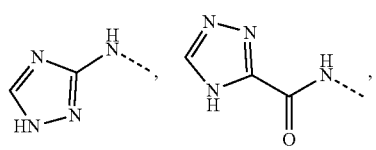
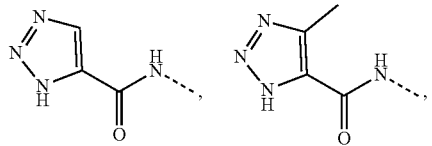

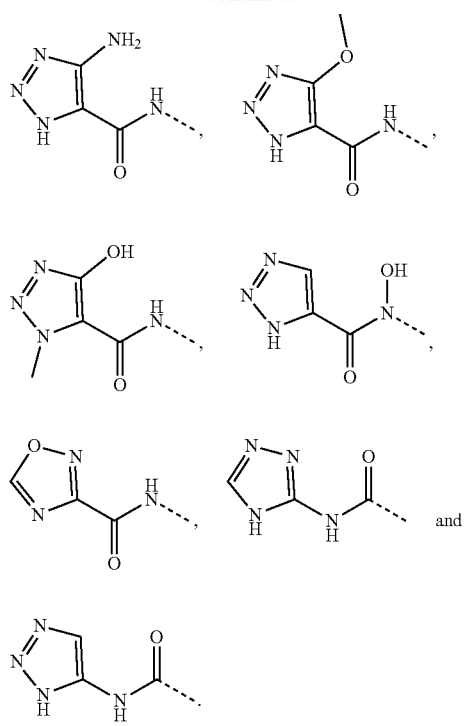
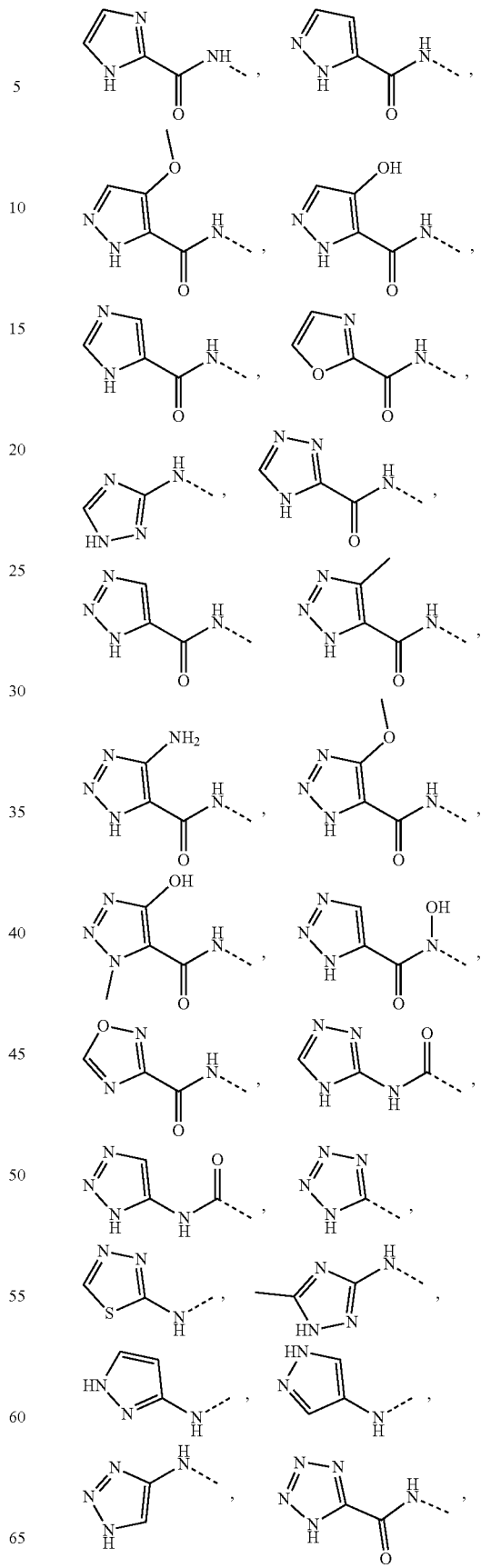
In some embodiments, the structural unit
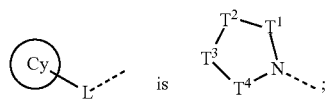
preferably, the structural unit is
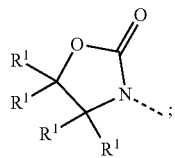
and more preferably, the structural unit is
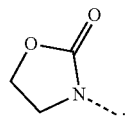
In some embodiments, the structural unit
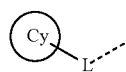
is selected from the group consisting of

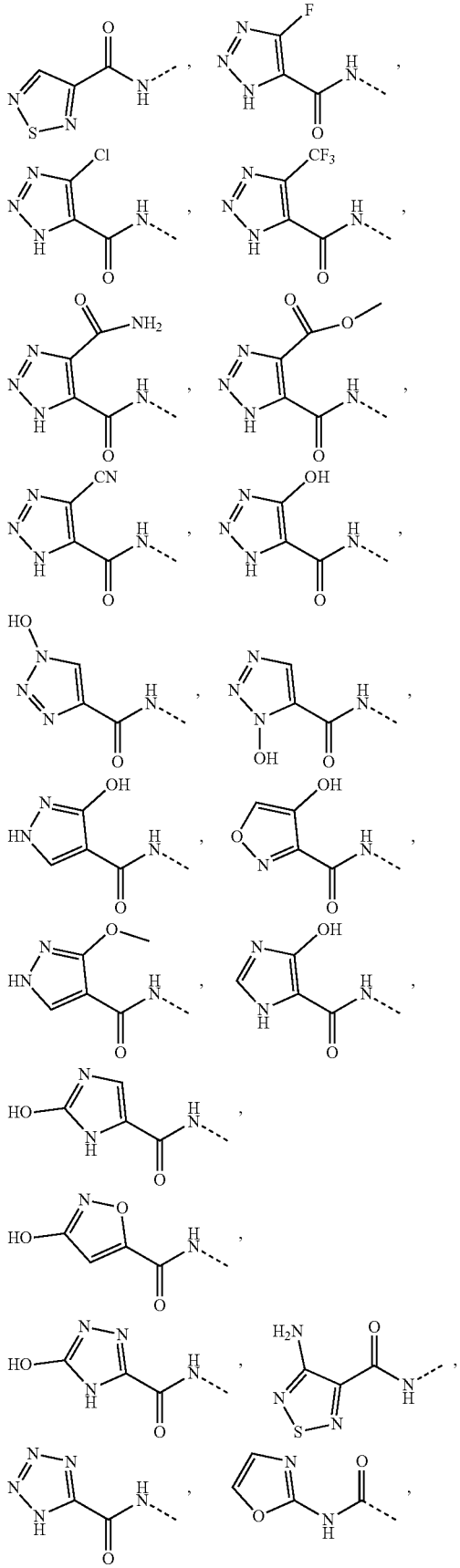

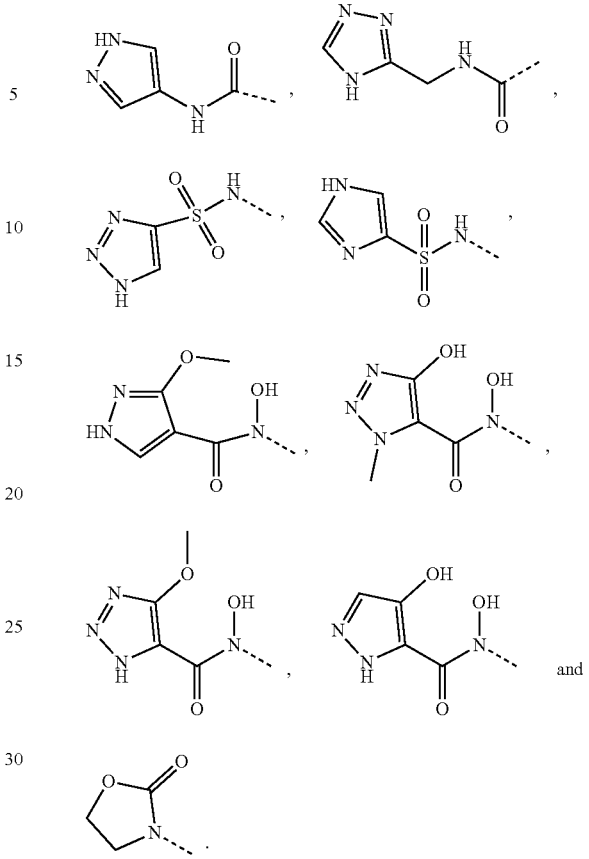

In some embodiments, $R^3$, $R^4$ and $R^5$ are each independently selected from the group consisting of halogen and $C_{1-3}$ alkyl, wherein the $C_{1-3}$ alkyl is optionally substituted by 1, 2, or 3 halogens, amino, or hydroxy; in some embodiments, $R^3$, $R^4$ and $R^5$ are each independently selected from the group consisting of halogen and methyl, wherein the methyl is optionally substituted by 1, 2, or 3 halogens, amino, or hydroxy; in some embodiments, $R^3$, $R^4$ and $R^5$ are each independently selected from methyl.

In some embodiments, each $R^6$ is independently selected from the group consisting of hydrogen, hydroxy and methyl, wherein the methyl is optionally substituted by 1, 2 or 3 halogens, amino or hydroxy; in some embodiments, each $R^6$ is independently selected from the group consisting of hydrogen, hydroxy and methyl; in some embodiments, each $R^6$ is independently selected from the group consisting of hydrogen and hydroxy.

In some embodiments, $E^1$ is selected from the group consisting of —(CH$_2$)$_2$— and —(CH$_2$)$_3$—.

In some embodiments, $E^2$ is selected from the group consisting of —O— and a bond.

In some embodiments, the structural unit -$E^1$-$E^2$- is selected from the group consisting of —(CH$_2$)$_2$—, —(CH$_2$)$_3$— and —(CH$_2$)$_2$—O—.

In some embodiments of the present application, the compound of formula (I), the isomer thereof or the pharmaceutically acceptable salt thereof is a compound of formula (II), an isomer thereof or a pharmaceutically acceptable salt thereof, (II)

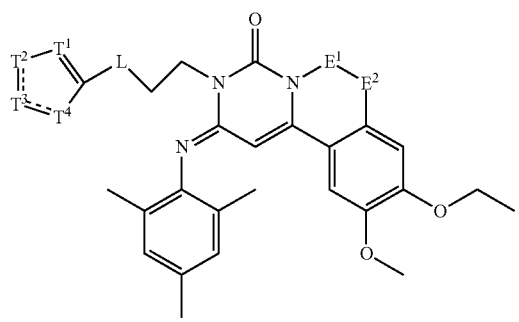

wherein,

T$^1$, T$^2$, T$^3$, T$^4$, E$^1$, E$^2$, L, and the structural unit

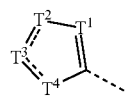

are as defined above.

In some embodiments, the structural unit

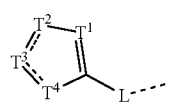

in the compound of formula (II) is as defined above.

In some embodiments, the structural unit -E$^1$-E$^2$- in the compound of formula (II) is as defined above.

In some embodiments of the present application, the compound of formula (II), the isomer thereof or the pharmaceutically acceptable salt thereof is a compound of formula (II-1), a compound of formula (II-2) or a compound of formula (II-3), an isomer thereof or a pharmaceutically acceptable salt thereof, (II-1)

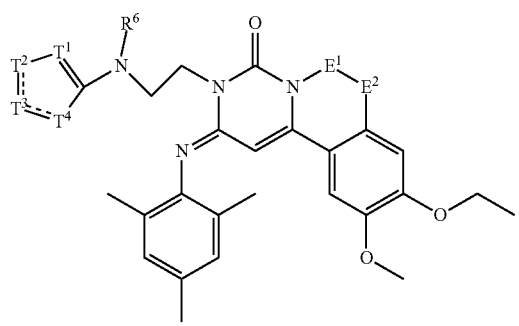

(II-2)

(II-3)

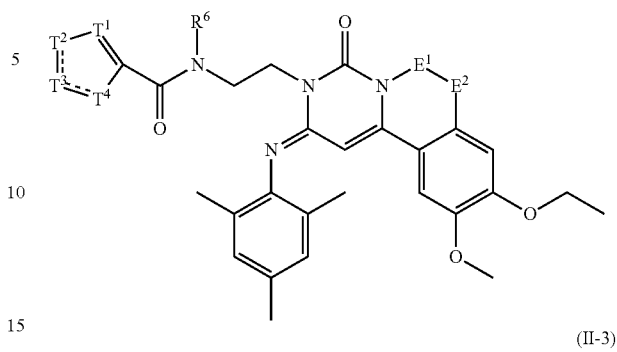

wherein,

R$^6$ is selected from the group consisting of hydrogen and hydroxy;

T$^1$, T$^2$, T$^3$, T$^4$, E$^1$, E$^2$, and the structural unit

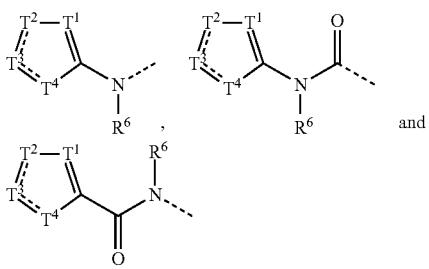

are as defined in formula (II) disclosed herein.

In some embodiments, the structural units in the compound of formula (II-1), formula (II-2), or formula (II-3) are as defined above.

In some embodiments, the structural unit -E$^1$-E$^2$- in the compound of formula (II-1), formula (II-2), or formula (II-3) is as defined above.

In another aspect, the present application also provides a compound of a formula, an isomer thereof or a pharmaceutically acceptable salt thereof, wherein the compound of the formula is selected from the group consisting of:

19
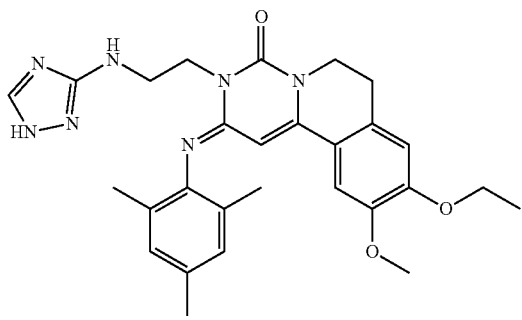 [SMILES: CCOc1cc2c(cc1OC)-c1c/c(=N\c3c(C)cc(C)cc3C)n(CCNc3cc[nH]n3)c(=O)n1CC2]
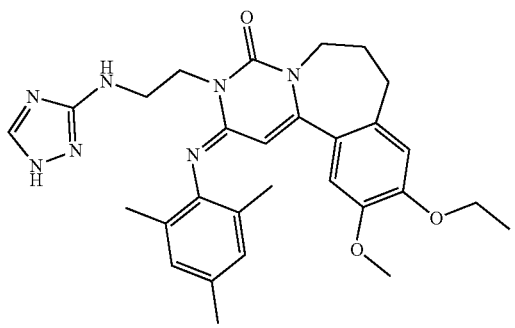
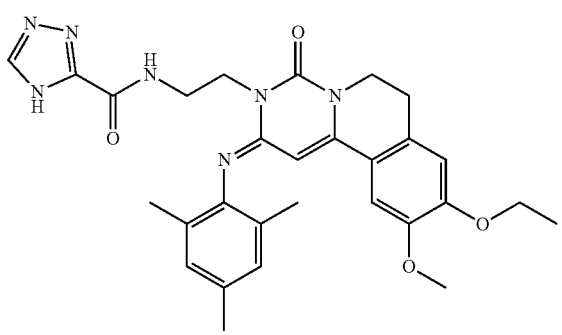
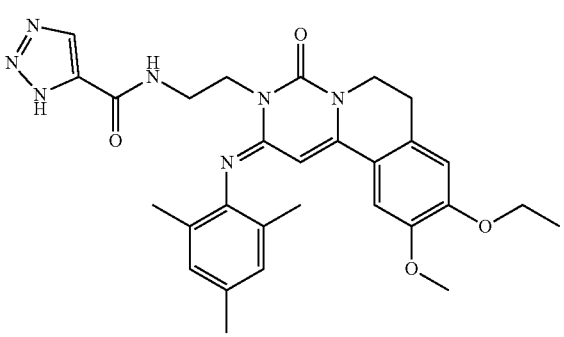 [SMILES: CCOc1cc2c(cc1OC)-c1c/c(=N\c3c(C)cc(C)cc3C)n(CCNC(=O)c3cnn[nH]3)c(=O)n1CC2]
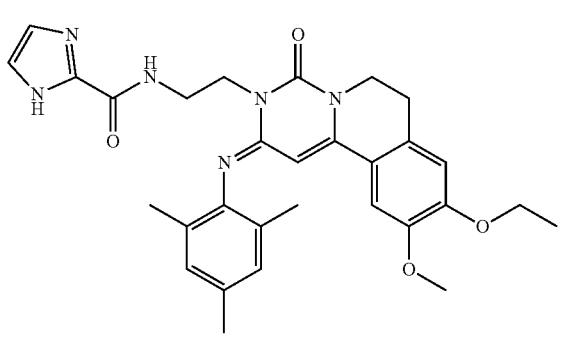 [SMILES: CCOc1cc2c(cc1OC)-c1c/c(=N\c3c(C)cc(C)cc3C)n(CCNC(=O)c3ncc[nH]3)c(=O)n1CC2]
20
-continued
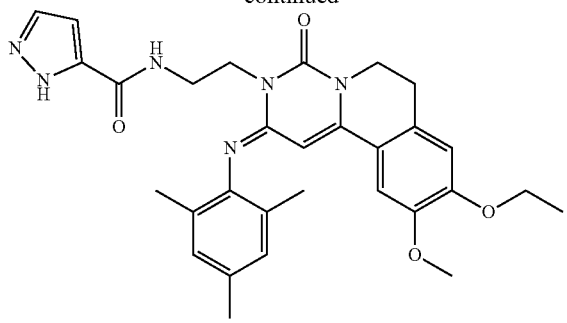
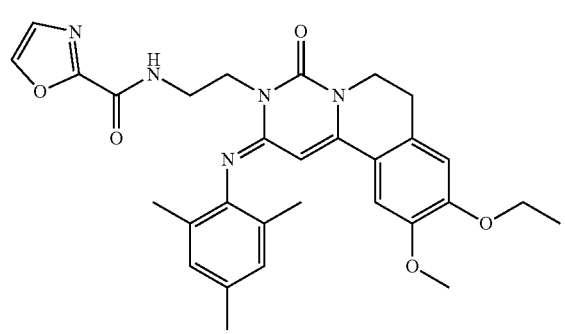 [SMILES: CCOc1cc2c(cc1OC)-c1c/c(=N\c3c(C)cc(C)cc3C)n(CCNC(=O)c3ncco3)c(=O)n1CC2]
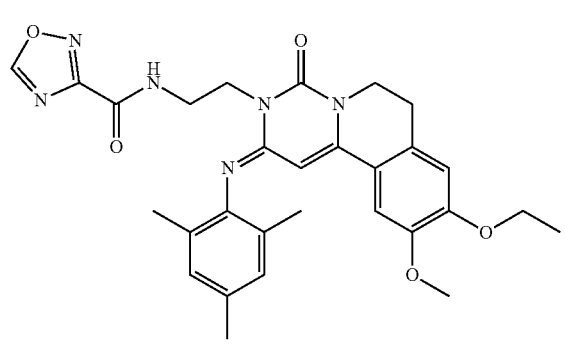 [SMILES: CCOc1cc2c(cc1OC)-c1c/c(=N\c3c(C)cc(C)cc3C)n(CCNC(=O)c3ncon3)c(=O)n1CC2]
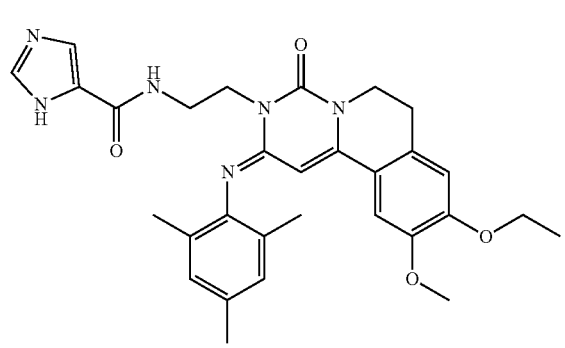 [SMILES: CCOc1cc2c(cc1OC)-c1c/c(=N\c3c(C)cc(C)cc3C)n(CCNC(=O)c3cnc[nH]3)c(=O)n1CC2]
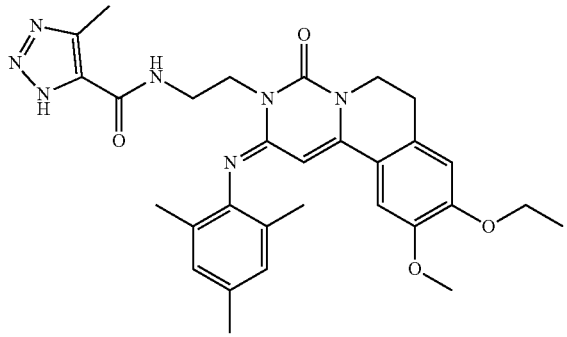 [SMILES: CCOc1cc2c(cc1OC)-c1c/c(=N\c3c(C)cc(C)cc3C)n(CCNC(=O)c3[nH]nnc3C)c(=O)n1CC2]

21
-continued
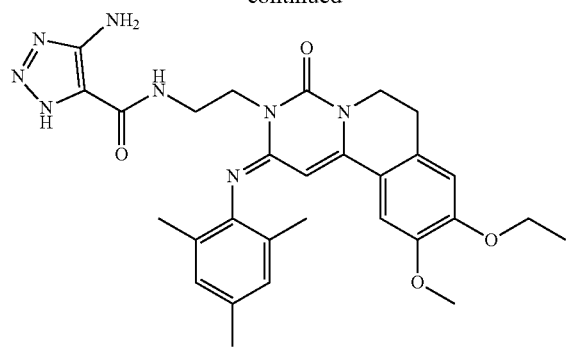
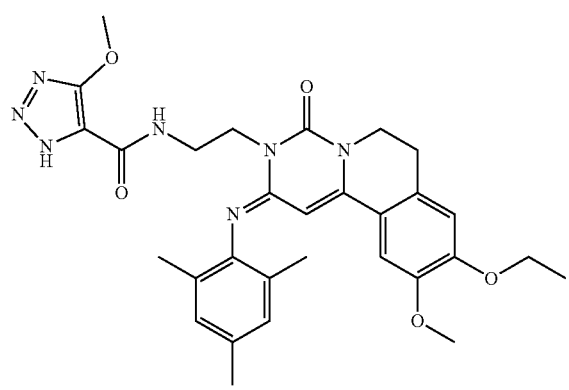 [SMILES: CCOc1cc2c(cc1OC)-c1c/c(=N\c3c(C)cc(C)cc3C)n(CCNC(=O)c3[nH]nnc3OC)c(=O)n1CC2]
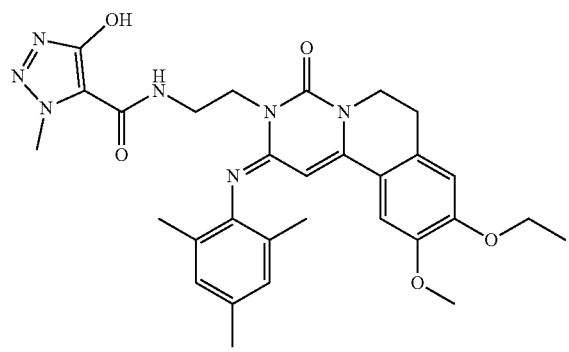
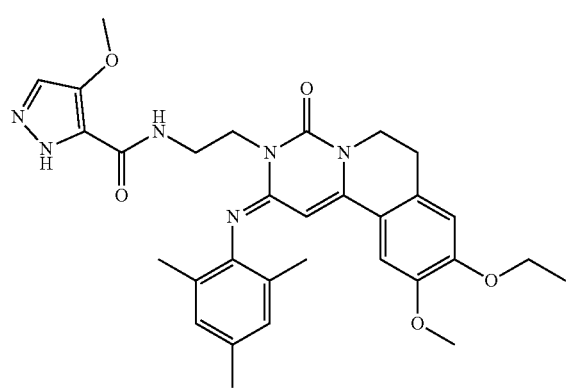
22
-continued
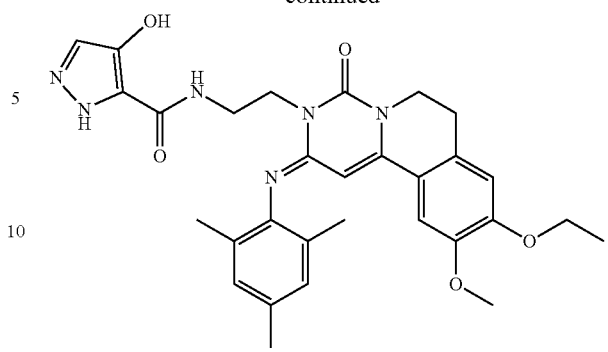
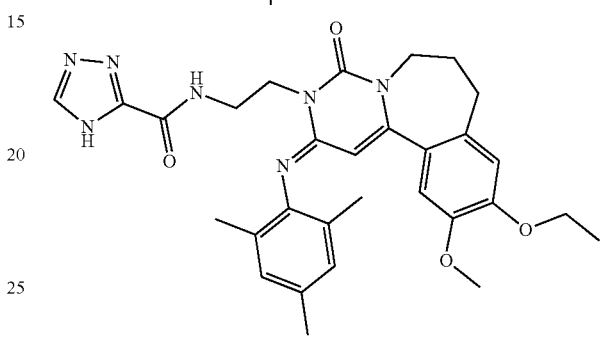
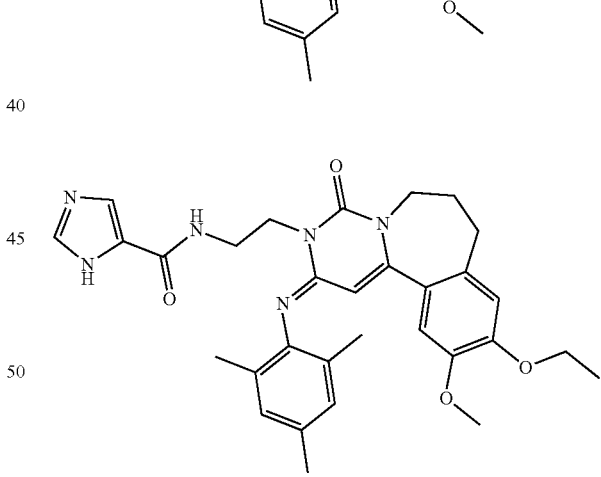
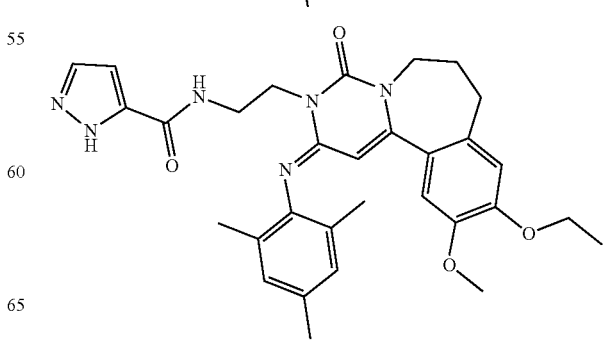

23
-continued
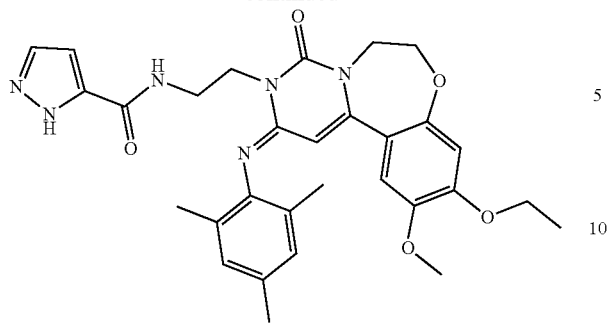
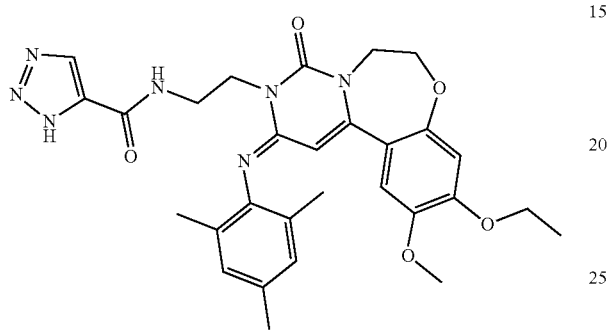
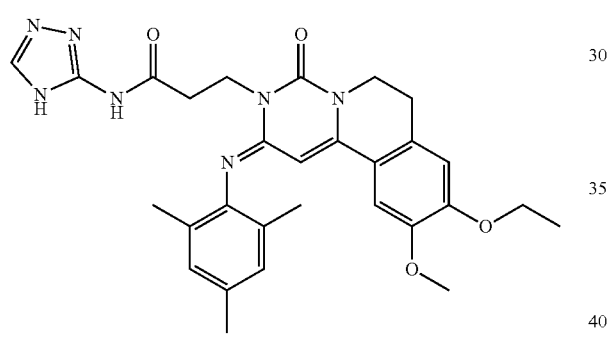
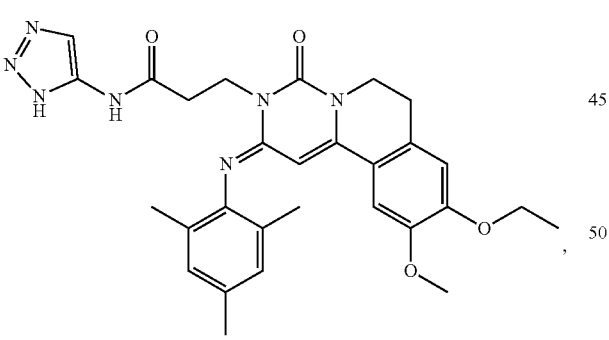
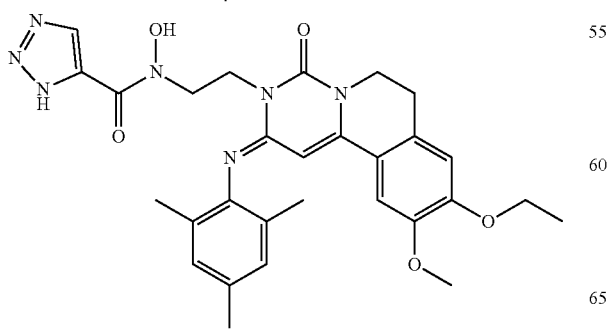
24
-continued
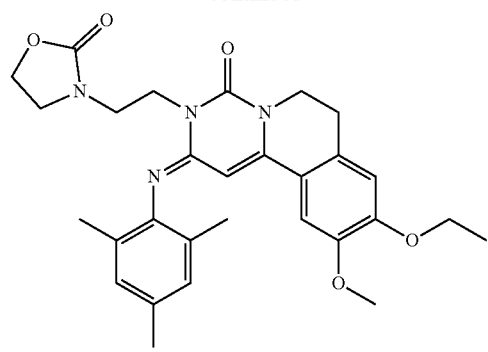
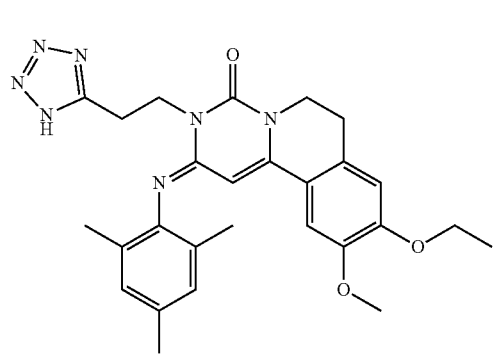
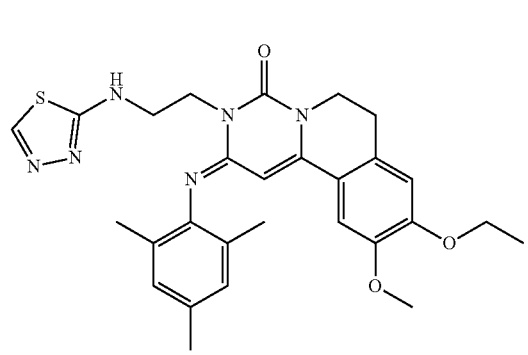
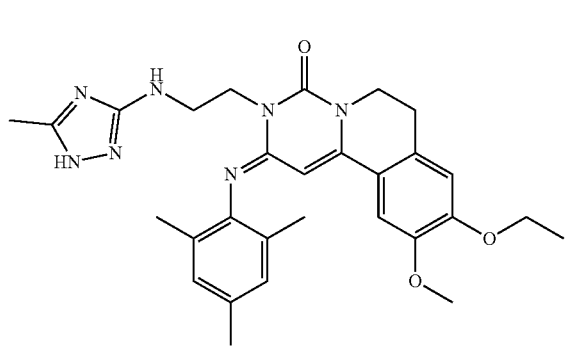
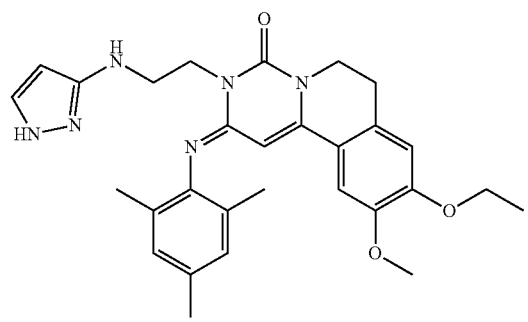

25
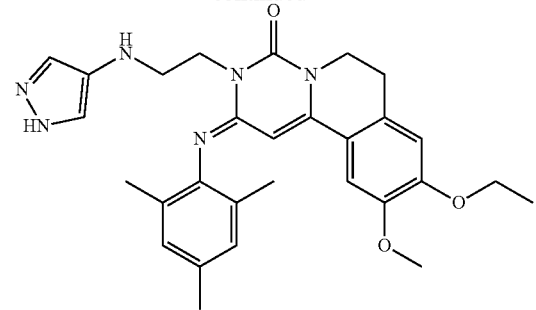
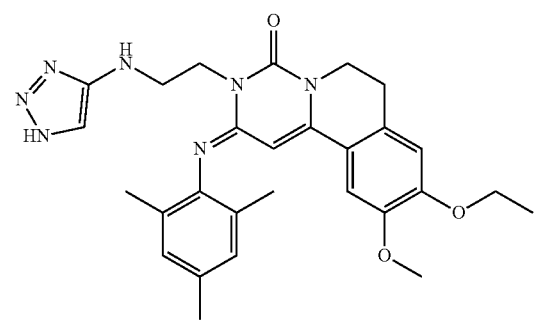
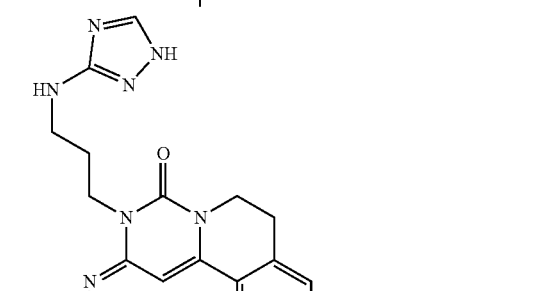
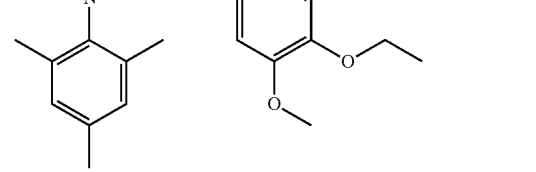
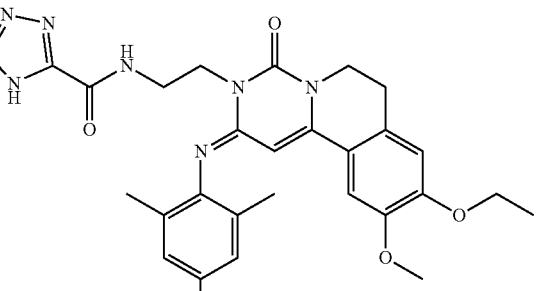
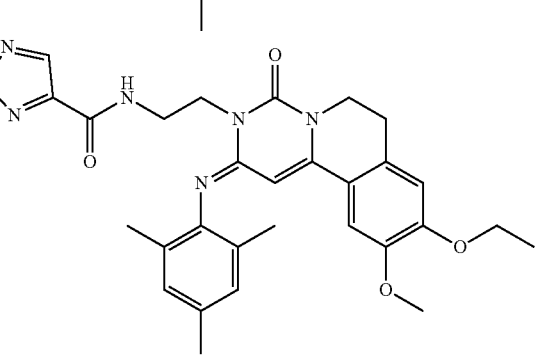
26
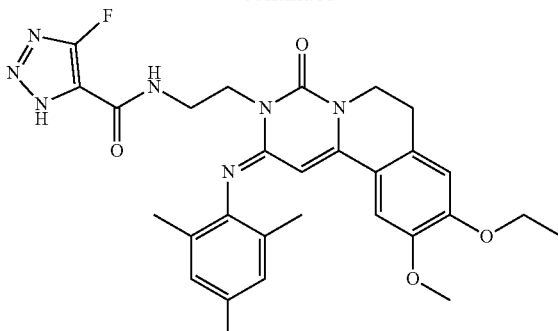
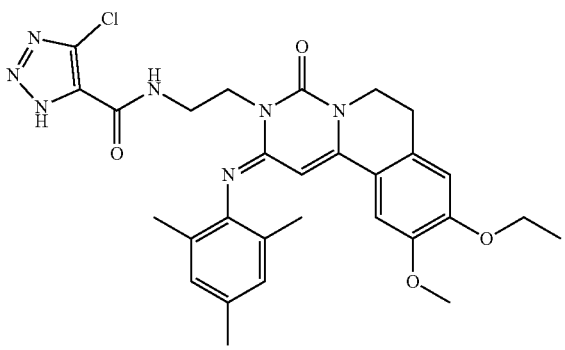 [SMILES: CCOc1cc2c(cc1OC)-c1c/c(=N\c3c(C)cc(C)cc3C)n(CCNC(=O)c3[nH]nnc3F)c(=O)n1CC2]
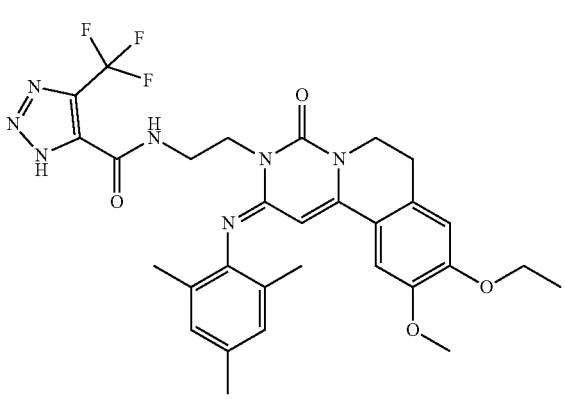
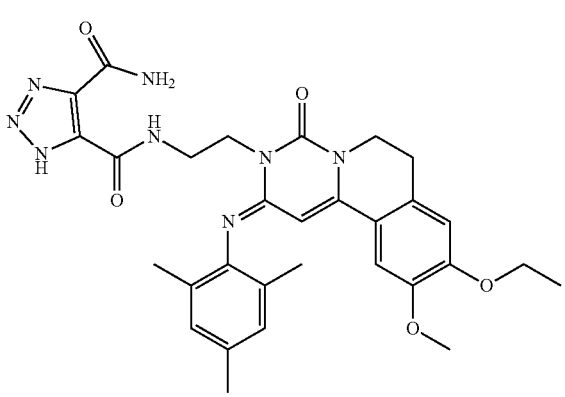 [SMILES: CCOc1cc2c(cc1OC)-c1c/c(=N\c3c(C)cc(C)cc3C)n(CCNC(=O)c3[nH]nnc3C(=O)OC)c(=O)n1CC2]

27
-continued
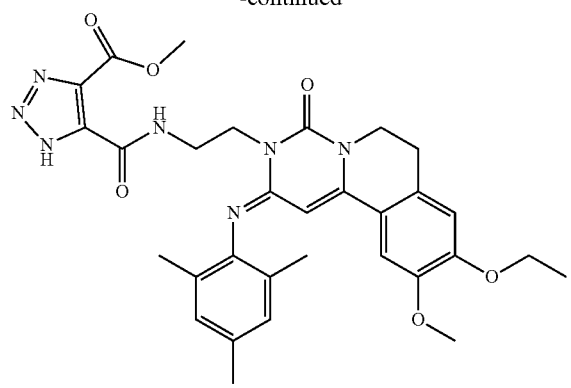
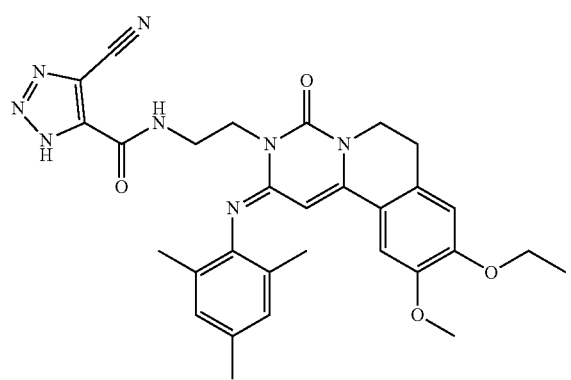 [SMILES: CCOc1cc2c(cc1OC)-c1c/c(=N\c3c(C)cc(C)cc3C)n(CCNC(=O)c3[nH]nnc3C#N)c(=O)n1CC2]
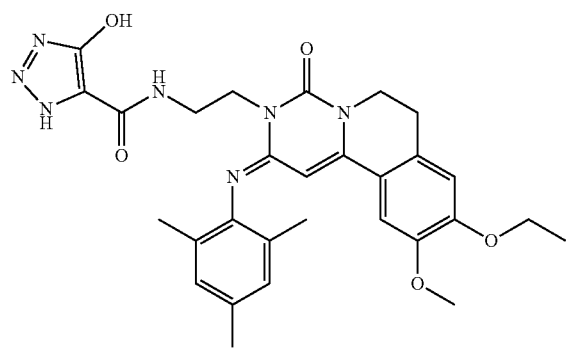
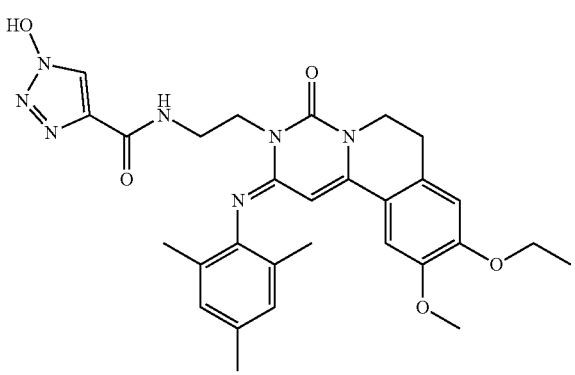 [SMILES: CCOc1cc2c(cc1OC)-c1c/c(=N\c3c(C)cc(C)cc3C)n(CCNC(=O)c3cn(O)nn3)c(=O)n1CC2]
28
-continued
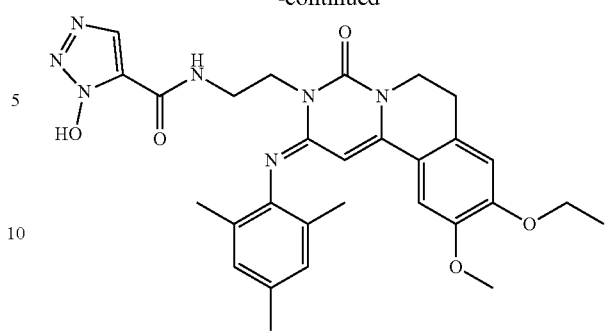
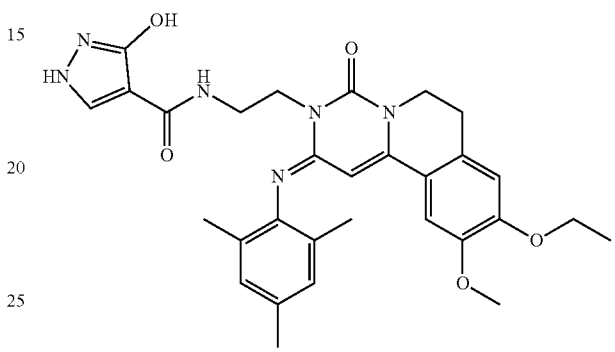
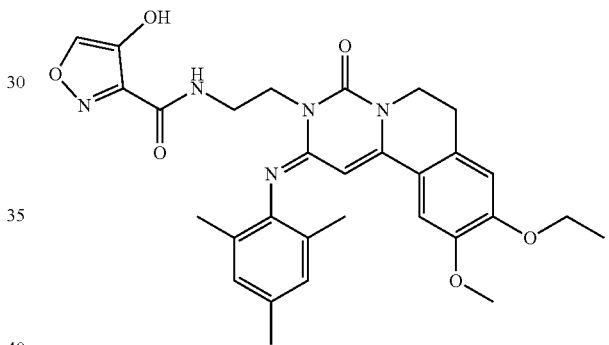
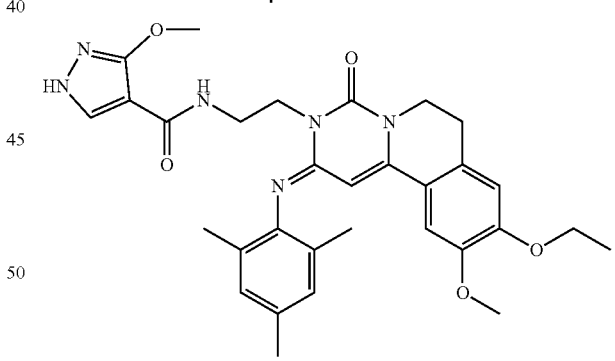
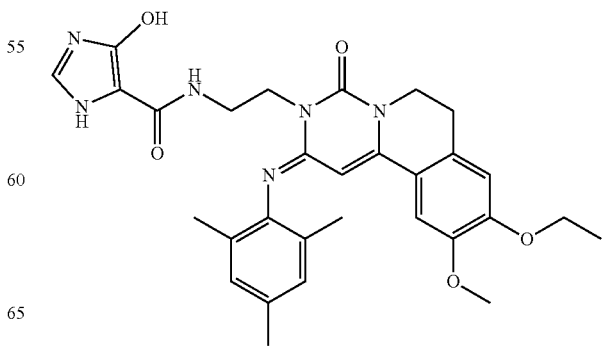

29
-continued
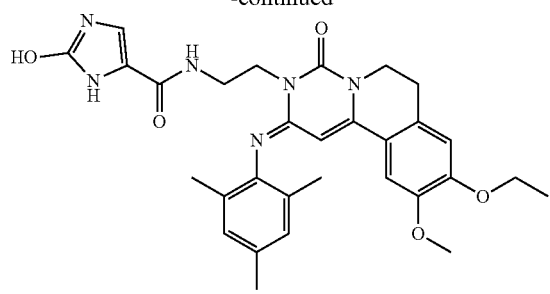
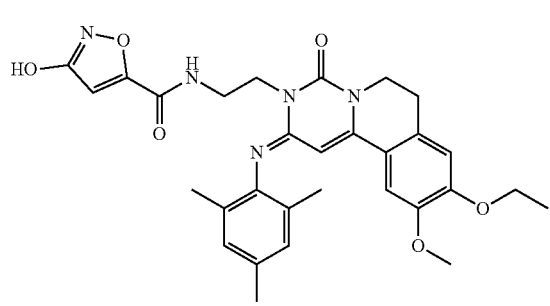
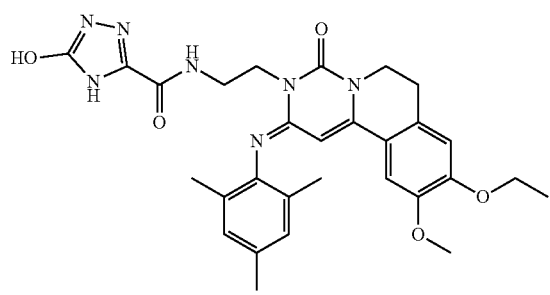
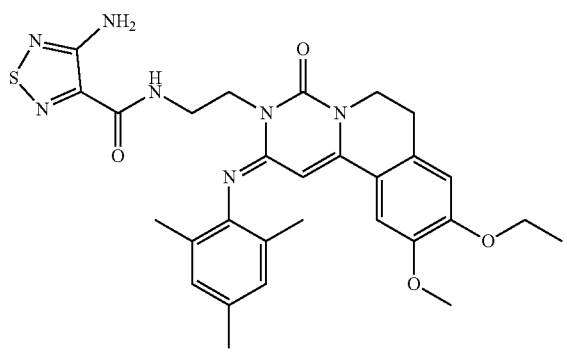
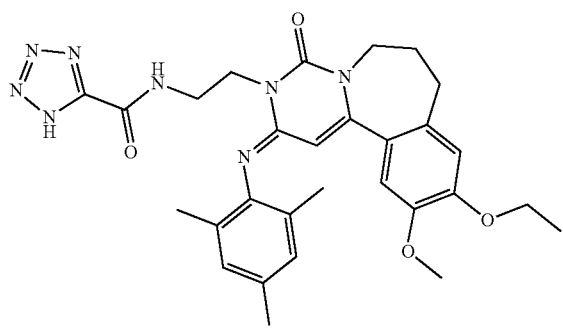
30
-continued
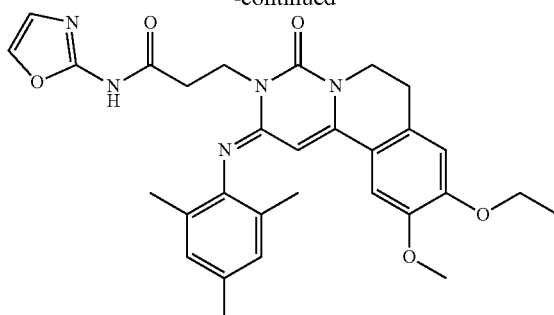
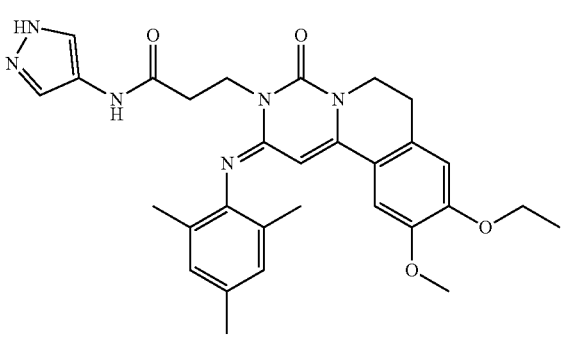
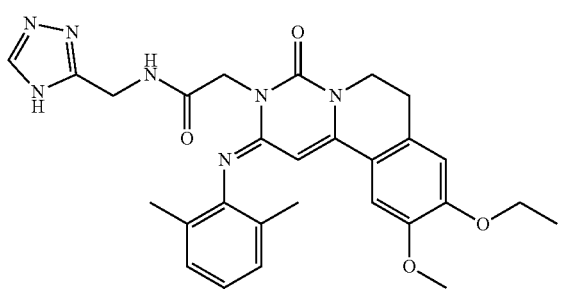
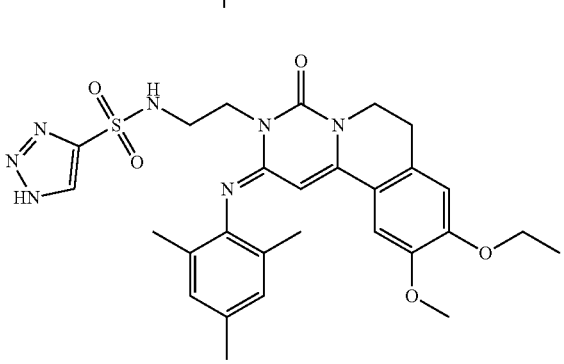
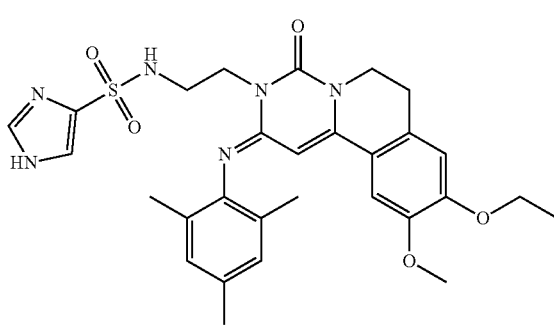

-continued

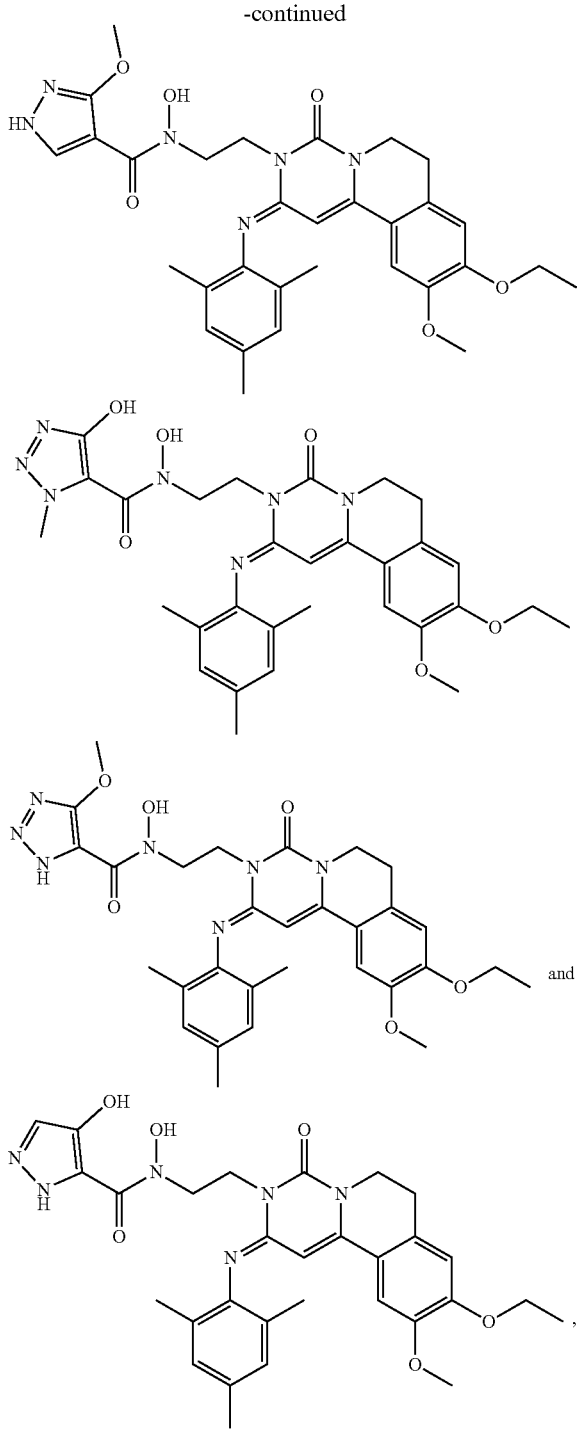

an isomer thereof or a pharmaceutically acceptable salt thereof.

In another aspect, the present application also provides a pharmaceutical composition comprising the compound of formula (I), the compound of formula (II), the compound of formula (II-1), the compound of (II-2), the compound of formula (II-3) or the specific compound described above, the isomer thereof or the pharmaceutically acceptable salt thereof. In some embodiments, the pharmaceutical composition disclosed herein also comprises a pharmaceutically acceptable excipient, carrier or diluent.

In another aspect, the present application also provides a method for treating a disease related to PDE3 and/or PDE4 in a mammal, comprising administering to the mammal, preferably a human, in need of the treatment a therapeutically effective amount of the compound of formula (I), the compound of formula (II), the compound of formula (II-1), the compound of formula (II-2), the compound of formula (II-3) or the specific compound described above, the isomer thereof or the pharmaceutically acceptable salt thereof, or the pharmaceutical composition thereof.

In another aspect, the present application also provides use of the compound of formula (I), the compound of formula (II), the compound of formula (II-1), the compound of formula (II-2), the compound of formula (II-3) or the specific compound, the isomer thereof or the pharmaceutically acceptable salt thereof, or the pharmaceutical composition thereof described above, in preparing a medicament for preventing or treating a disease related to PDE3 and/or PDE4.

In another aspect, the present application also provides use of the compound of formula (I), the compound of formula (II), the compound of formula (II-1), the compound of formula (II-2), the compound of formula (II-3) or the specific compound described above, the isomer thereof or the pharmaceutically acceptable salt thereof, or the pharmaceutical composition thereof in preventing or treating a disease related to PDE3 and/or PDE4.

In another aspect, the present application also provides the compound of formula (I), the compound of formula (II), the compound of formula (II-1), the compound of formula (II-2), the compound of formula (II-3) or the specific compound described above, the isomer thereof or the pharmaceutically acceptable salt thereof, or the pharmaceutical composition thereof for preventing or treating a disease related to PDE3 and/or PDE4.

In some embodiments of the present application, the disease related to PDE3 and/or PDE4 is selected from asthma and chronic obstructive pulmonary disease (COPD).

TECHNICAL EFFECTS

The compound disclosed herein has remarkable dual inhibition effect on PDE3 and PDE4, has significant inhibition effect on TNF-α in human peripheral blood mononuclear cells (hPBMC), and also shows excellent anti-inflammatory action in model of rat acute lung injury induced by lipopolysaccharide (LPS). The compound has high in vivo plasma clearance, low systemic exposure in plasma by oral administration and low oral bioavailability, and good safety in administration via a local route. Its inhibition effect is low on 5 isozymes (CYP1A2, CYP2C9, CYP2C19, CYP2D6 and CYP3A4) of human liver microsomal cytochrome P450, and the risk of drug-drug interaction is avoided. Besides, the compound reduces the total white blood cells in BALF, has remarkable anti-inflammatory effect, takes effect at a low dose, and reduces the airway resistance index Penh.

DEFINITIONS AND DESCRIPTION

Unless otherwise stated, the following terms and phrases used herein are intended to have the following meanings.

A particular term or phrase, unless otherwise specifically defined, should not be considered as uncertain or unclear, but construed according to its common meaning. When referring to a trade name, it is intended to refer to its corresponding commercial product or its active ingredient.

The valence of each atom is normal in the compound formed by connecting each group, and the formed compound can exist stably.

The listed linking groups in the present application have the direction for linking. For example, in

when the linking group L is —N(R$^6$)C(O)—, the —N(R$^6$)C(O)— links two ends in a direction same as left-to-right reading order to form

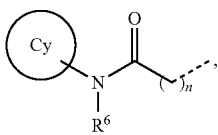

and when L is —C(O)N(R$^6$)—, the —C(O)N(R$^6$)— links two ends in a direction same as left-to-right reading order to form

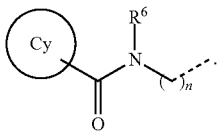

A combination of the linking group, a substituent and/or a variant thereof is permissible only if the combination can result in a stable compound.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The pharmaceutically acceptable salts disclosed herein can be synthesized from a parent compound having an acidic or basic group by conventional chemical methods. In general, such salts are prepared by the following method: the free acid or base form of the compound reacting with a stoichiometric amount of the appropriate base or acid in water or an organic solvent or a mixture thereof.

The compounds disclosed herein can be in the form of a geometric isomer or stereoisomer. All such compounds are contemplated herein, including cis-isomers and trans-isomers, (-)- and (+)-enantiomers, (R)- and (S)-enantiomers, diastereomers, (D)-isomers, (L)-isomers, and racemic mixtures and other mixtures thereof, such as an enantiomer or diastereomer enriched mixture, all of which are included within the scope of the present application. Substituents such as alkyl may have an additional asymmetric carbon atom. All these isomers and mixtures thereof are encompassed within the scope of the present application.

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerization and imine-enamine isomerization. A specific example of the proton tautomer is an imidazole moiety where a proton can transfer between two ring nitrogens. A valence tautomer includes the interconversion via recombination of some bonding electrons.

The compound disclosed herein can be asymmetrical, for example, has one or more stereoisomers. Unless otherwise stated, all stereoisomers are included, for example, enantiomers and diastereoisomers. The compound with asymmetric carbon atoms disclosed herein can be separated in an optically pure form or in a racemic form.

The optically pure form can be separated from a racemic mixture or can be synthesized using a chiral raw material or a chiral reagent.

Optically active (R)- and (S)-isomers and D and L isomers can be prepared by chiral synthesis or chiral reagents or other conventional techniques. An enantiomer of certain compound disclosed herein can be prepared by asymmetric synthesis or derivatization using a chiral auxiliary, wherein the resulting diastereomeric mixture is separated and the auxiliary group is cleaved so as to provide the desired pure enantiomer. Alternatively, when the molecule contains a basic functional group (such as amino) or an acidic functional group (such as carboxyl), the compound reacts with an appropriate optically active acid or base to form a salt of the diastereoisomer, which is then subjected to diastereomeric resolution through conventional methods in the art to get the pure enantiomer.

Furthermore, the enantiomer and the diastereomer are generally isolated through chromatography using a chiral stationary phase, optionally in combination with chemical derivatization (e.g., carbamate formation from amines).

The present application also comprises isotopically-labeled compounds which are identical to those recited herein but one or more atoms thereof are replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl.

The compound disclosed herein may contain an unnatural proportion of atomic isotope at one or more of the atoms that constitute the compound. For example, the compound may be labeled with a radioisotope, such as tritium ($^3$H), iodine-125 ($^{125}$I), or C-14 ($^{14}$C). For another example, hydrogen can be substituted by deuterium to form a deuterated drug, and the bond formed by deuterium and carbon is firmer than that formed by common hydrogen and carbon. Compared with an un-deuterated drug, the deuterated drug has the advantages of reduced toxic side effect, increased stability, enhanced efficacy, prolonged biological half-life and the like. All isotopic variations of the compound described herein, whether radioactive or not, are encompassed within the scope of the present application.

Furthermore, substitution with heavier isotopes such as deuterium (i.e., $^2$H) may provide certain therapeutic advantages (e.g., increased in vivo half-life or reduced dosage requirement) resulting from greater metabolic stability and hence may be preferred in some circumstances in which deuterium substitution may be partial or complete, wherein partial deuterium substitution refers to substitution of at least one hydrogen with at least one deuterium.

"Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted by substituents which may include deuterium and hydrogen variants, as long as the valence of the specific atom is normal and the compound after substitution is stable. When the substituent is oxygen (i.e., =O), it means that two hydrogen atoms are substituted. Substitution by oxygen does not occur on aromatic groups.

The term "optionally substituted" means that an atom can be or cannot be substituted by a substituent. Unless otherwise specified, the type and number of the substituent may be arbitrary as long as being chemically achievable.

When any variable (e.g., R) occurs more than once in the constitution or structure of a compound, the definition of the variable in each case is independent. Thus, for example, if a group is substituted by 0-2 R, the group can be optionally substituted by two R at most, and the definition of R in each case is independent. Furthermore, a combination of a substituent and/or a variant thereof is permissible only if the combination can result in a stable compound.

When a variable is a single bond, it means that the two groups are directly linked. For example, in A-L-Z, when L represents a single bond, it means that the structure is actually A-Z.

When a bond of a substituent is cross-linked to two atoms on a ring, the substituent can be bonded to any atom on the ring. For example, structural unit

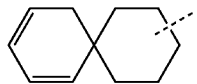

represents that substitution may occur at any position of cyclohexyl or cyclohexadienyl.

The term "halo-" or "halogen" refers to fluorine, chlorine, bromine and iodine.

The term "hydroxy" refers to —OH group.

The term "cyano" refers to —CN group.

The term "amino" refers to —NH$_2$ group.

When a substituent is absent, it means that the substituent does not exist. For example, when X is absent in A-X, the structure of A-X is actually A. When it is not specified by which atom the listed substituent is linked to the group to be substituted, the substituent can be linked via any atom of the group. For example, pyridinyl as a substituent can be linked to the group to be substituted through any carbon atom on the pyridine ring.

The term "alkyl" refers to hydrocarbyl with a general formula of C$_n$H$_{2n+1}$. The alkyl can be linear or branched. For example, the term "C$_{1-6}$ alkyl" refers to alkyl with 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). The alkyl moiety (namely alkyl) of alkoxy, alkylamino, dialkylamino, alkylsulfonyl and alkylthio is similarly defined as above.

The term "alkoxy" refers to —O-alkyl.

Unless otherwise specified, $C_{n-n+m}$ or $C_n$—$C_{n+m}$ includes any one of the specific cases of n to n+m carbons; for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$; $C_{n-n+m}$ or $C_n$-$C_{n+m}$ also includes any one of the ranges of n to n+m; for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc.

Similarly, n–n+m membered represents the number of atoms on the ring is n to n+m; for example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring; n–n+m membered also represents any range in n to n+m; for example, 3-12 membered ring includes 3-6 membered ring, 3-9 membered ring, 5-6 membered ring, 5-7 membered ring, 6-7 membered ring, 6-8 membered ring, 6-10 membered ring, etc.

The term "heterocyclyl" refers to a fully saturated or partially unsaturated (but not fully unsaturated heteroaromatic group) nonaromatic ring which may exist in the form of a monocyclic, bridged cyclic or spiro structure. Unless otherwise specified, the heterocyclyl is usually a 3-7 membered ring containing 1-3 heteroatoms (preferably 1 or 2 heteroatoms) independently selected from the group consisting of sulfur, oxygen and/or nitrogen. Non-limiting examples of heterocyclyl include, but are not limited to, oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, thiomorpholinyl, tetrahydrothienyl, dihydropyridazinyl, dihydropyrimidinyl, dihydropyridinyl, dihydroimidazolyl, dihydroisoxazolyl, dihydrotriazolyl, and dihydropyridazinyl. Preferably, the heterocyclyl is a monocyclic heterocyclyl with 5 ring atoms.

The term "heteroaryl" refers to a monocyclic or fused polycyclic system which comprises at least one ring atom selected from the group consisting of N, O and S, with the remaining ring atoms being C, and which has at least one aromatic ring. Preferably, the heteroaryl has a single 4-8 membered ring, in particular, a 5-8 membered ring, or is a plurality of fused rings comprising 6-14 ring atoms, in particular 6-10 ring atoms. Non-limiting examples of heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl, isoxazolyl, oxadiazolyl, thiadiazolyl, and thiazolyl.

The term "treating" refers to administering the compound or formulation described herein to prevent, ameliorate or eliminate a disease or one or more symptoms associated with the disease, and includes:
  (i) preventing the occurrence of the disease or disease state in a mammal, particularly when such a mammal is predisposed to the disease state but has not yet been diagnosed as having it;
  (ii) inhibiting a disease or disease state, i.e., arresting its development; and
  (iii) alleviating a disease or disease state, i.e., causing its regression.

The term "therapeutically effective amount" refers to an amount of the compound disclosed herein for (i) treating or preventing a specific disease, condition or disorder, (ii) alleviating, improving or eliminating one or more symptoms of a specific disease, condition or disorder, or (iii) preventing or delaying onset of one or more symptoms of a specific disease, condition or disorder described herein. The amount of the compound disclosed herein composing the "therapeutically effective amount" varies dependently on the compound, the disease state and its severity, the administration regimen, and the age of the mammal to be treated, but can be determined routinely by those skilled in the art in accordance with their knowledge and the present disclosure.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound disclosed herein to an organic entity.

The term "pharmaceutically acceptable excipients" refers to those excipients which do not have a significant irritating effect on an organic entity and do not impair the biological activity and properties of the active compound. Suitable excipients are well known to those skilled in the art, such as carbohydrate, wax, water-soluble and/or water-swellable polymers, hydrophilic or hydrophobic material, gelatin, oil, solvent, water.

The word "comprise" and variations thereof such as "comprises" or "comprising" will be understood in an open, non-exclusive sense, i.e., "including but not limited to".

The pharmaceutical composition disclosed herein can be prepared by combining the compound disclosed herein with a suitable pharmaceutically acceptable excipient, and can be formulated. For example, it can be formulated into a solid, semisolid, liquid, or gaseous formulation, such as tablet, pill, capsule, powder, granule, ointment, emulsion, suspension, suppository, injection, inhalant, gel, microsphere and aerosol.

Typical routes of administration of a compound or a pharmaceutically acceptable salt thereof or a pharmaceutical composition thereof disclosed herein include, but are not limited to, oral, rectal, local, inhalation, parenteral, sublingual, intravaginal, intranasal, intraocular, intraperitoneal, intramuscular, subcutaneous and intravenous administration.

The pharmaceutical composition disclosed herein can be manufactured by methods well known in the art, such as by conventional mixing, dissolving, granulating, dragee-making, levigating, emulsifying and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to, binders, diluents, disintegrants, lubricants, glidants, sweeteners or flavoring agents.

The pharmaceutical compositions may also be suitable for parenteral administration, such as sterile solutions, suspensions or lyophilized products in suitable unit dosage forms.

In all of the administration methods of the compound of general formula I described herein, the daily dose administered is from 0.01-200 mg/kg body weight.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein.

The chemical reactions of the embodiments disclosed herein are carried out in a suitable solvent that must be suitable for the chemical changes in the present application and the reagents and materials required therefor. In order to acquire the compounds disclosed herein, it is sometimes necessary for one skilled in the art to modify or select a synthesis procedure or a reaction scheme based on the existing embodiments.

An important consideration in synthesis route planning in the art is the selection of suitable protecting groups for reactive functional groups (e.g., amino in the present application). For example, reference may be made to Greene's Protective Groups in Organic Synthesis (4th Ed.) Hoboken, New Jersey: John Wiley & Sons, Inc. All references cited herein are incorporated by reference in their entirety.

In some embodiments, the compound of formula (I) disclosed herein may be prepared by one skilled in the art of organic synthesis using standard methods in the art by the following routes:

Preparation of intermediates:

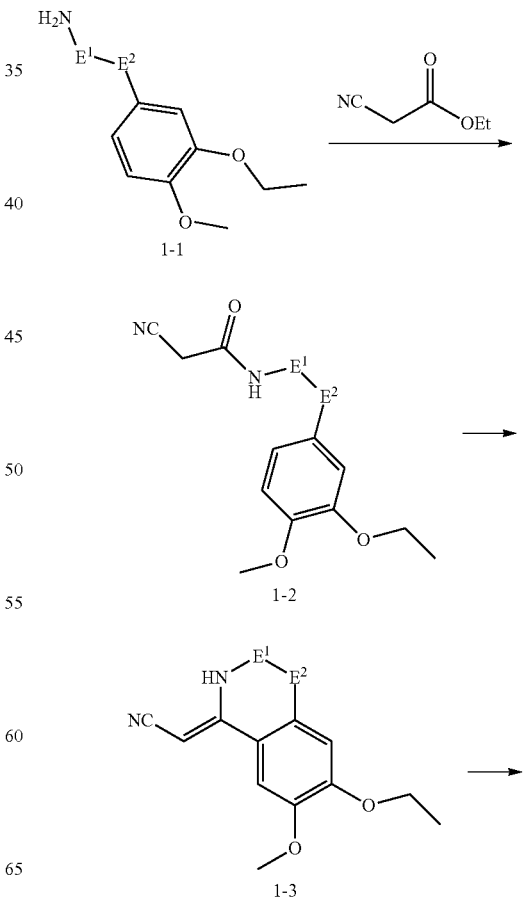

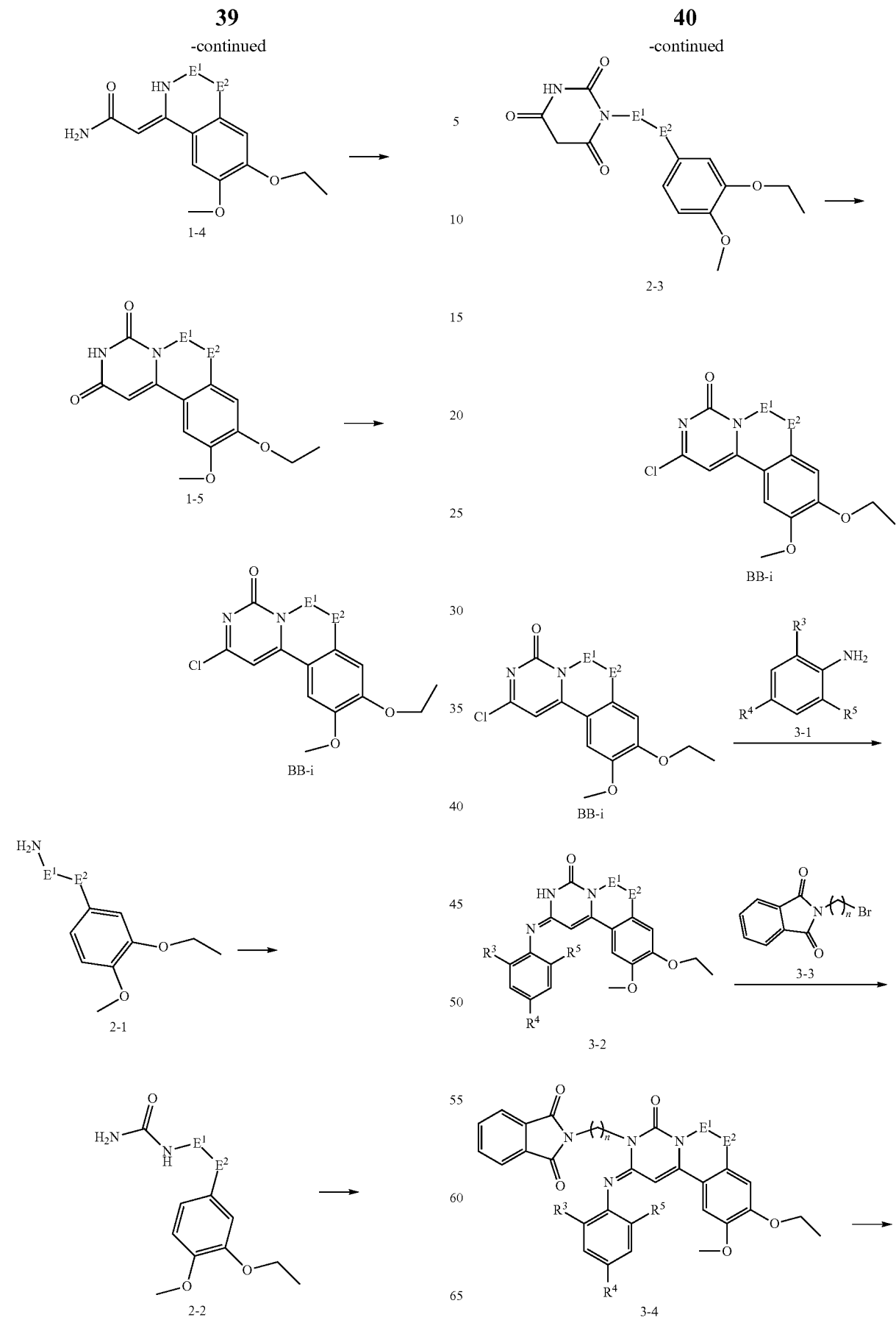

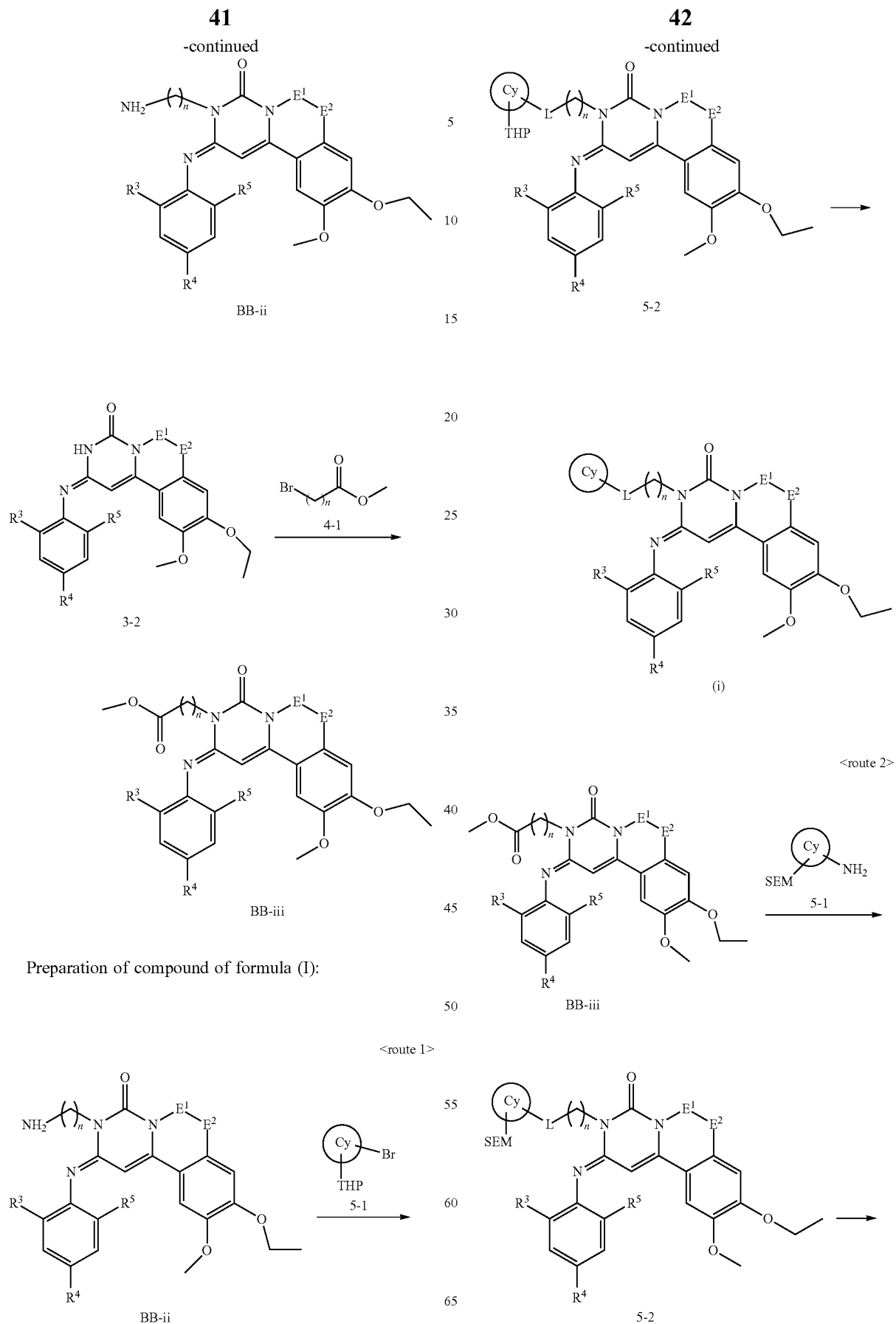
Preparation of compound of formula (I):

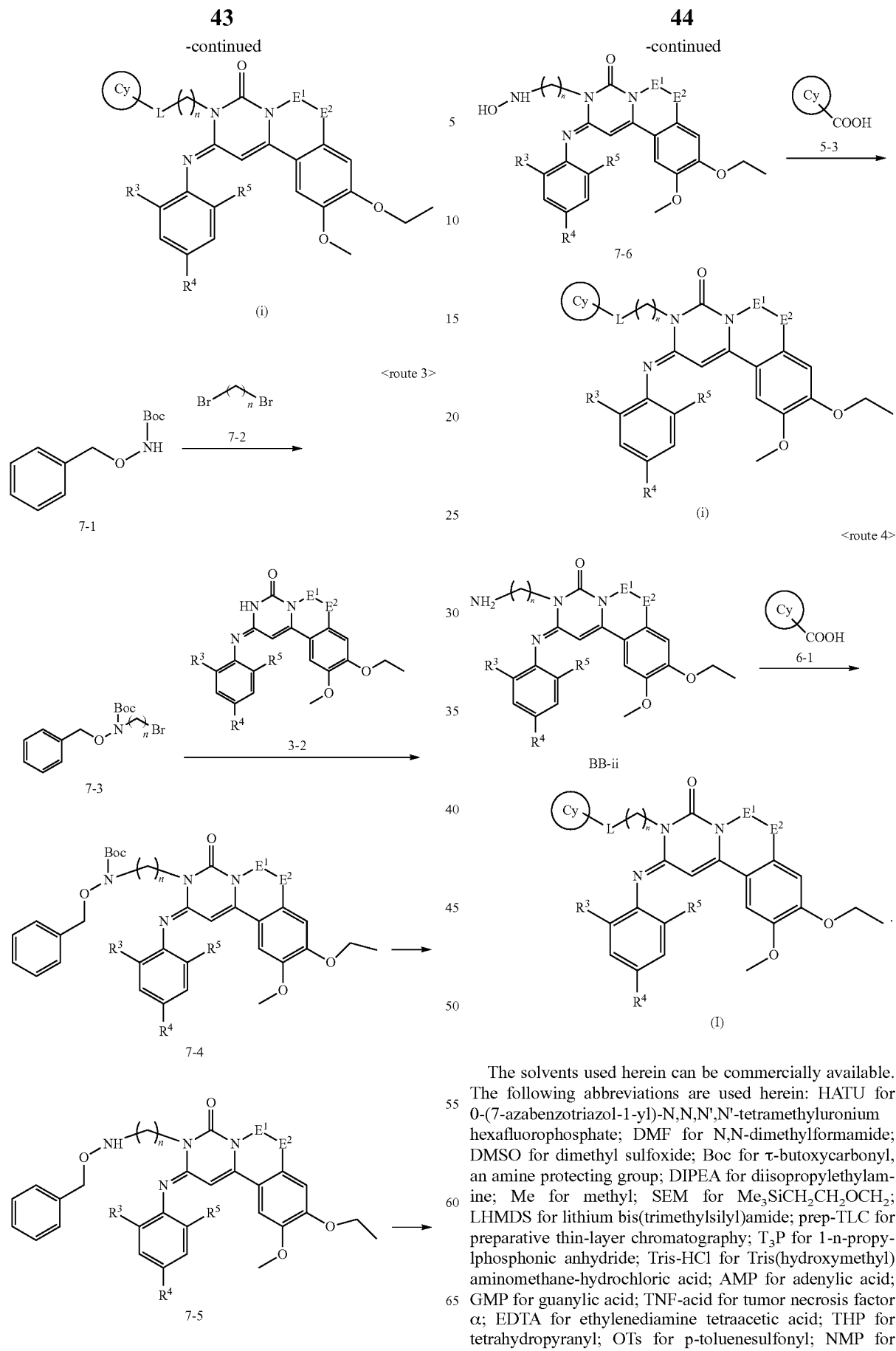

The solvents used herein can be commercially available. The following abbreviations are used herein: HATU for 0-(7-azabenzotriazol-1-yl)-N,N,N',N'-tetramethyluronium hexafluorophosphate; DMF for N,N-dimethylformamide; DMSO for dimethyl sulfoxide; Boc for τ-butoxycarbonyl, an amine protecting group; DIPEA for diisopropylethylamine; Me for methyl; SEM for $Me_3SiCH_2CH_2OCH_2$; LHMDS for lithium bis(trimethylsilyl)amide; prep-TLC for preparative thin-layer chromatography; $T_3P$ for 1-n-propylphosphonic anhydride; Tris-HCl for Tris(hydroxymethyl) aminomethane-hydrochloric acid; AMP for adenylic acid; GMP for guanylic acid; TNF-acid for tumor necrosis factor α; EDTA for ethylenediamine tetraacetic acid; THP for tetrahydropyranyl; OTs for p-toluenesulfonyl; NMP for N-methylpyrrolidone; THF for tetrahydrofuran; MeCN for acetonitrile; PyBop for benzotriazol-1-yl-oxytripyrrolidino-phosphonium hexafluorophosphate; and Et for ethyl.

DETAILED DESCRIPTION

Figure 1:
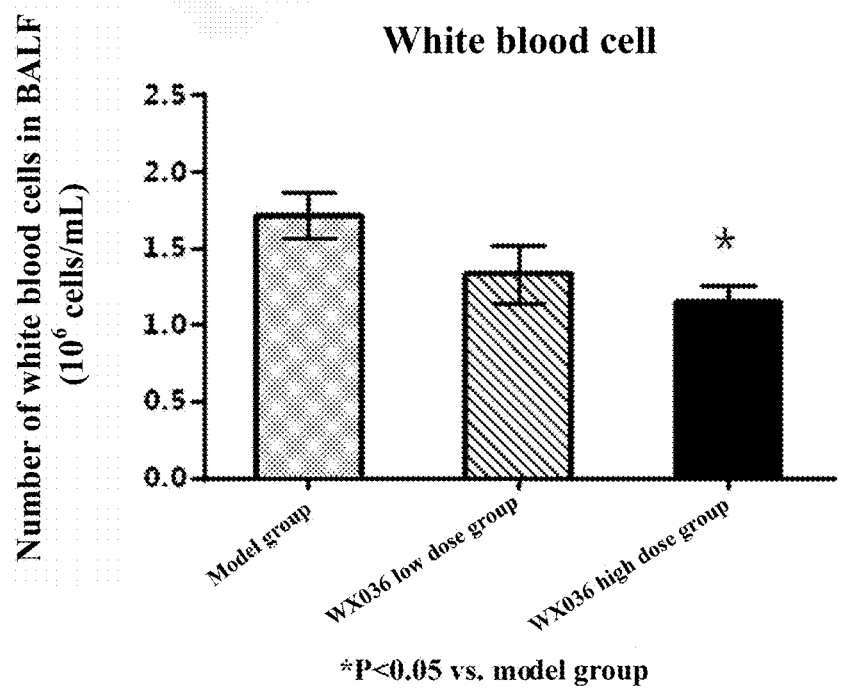
FIG. 1 shows the total white blood cells in bronchoalveolar lavage fluid (BALF)

The present application is described in detail below by way of examples. However, this is by no means disadvantageously limiting the scope of the present application. Although the present application has been described in detail herein and specific examples have also been disclosed, it will be apparent to those skilled in the art that various changes and modifications can be made to the specific embodiments without departing from the spirit and scope of the present application.

Example 1

Synthesis of Compound BB-1

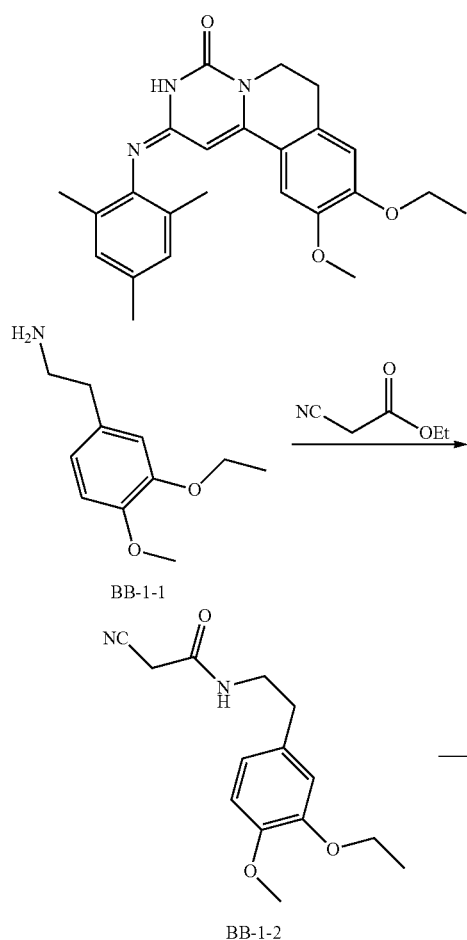

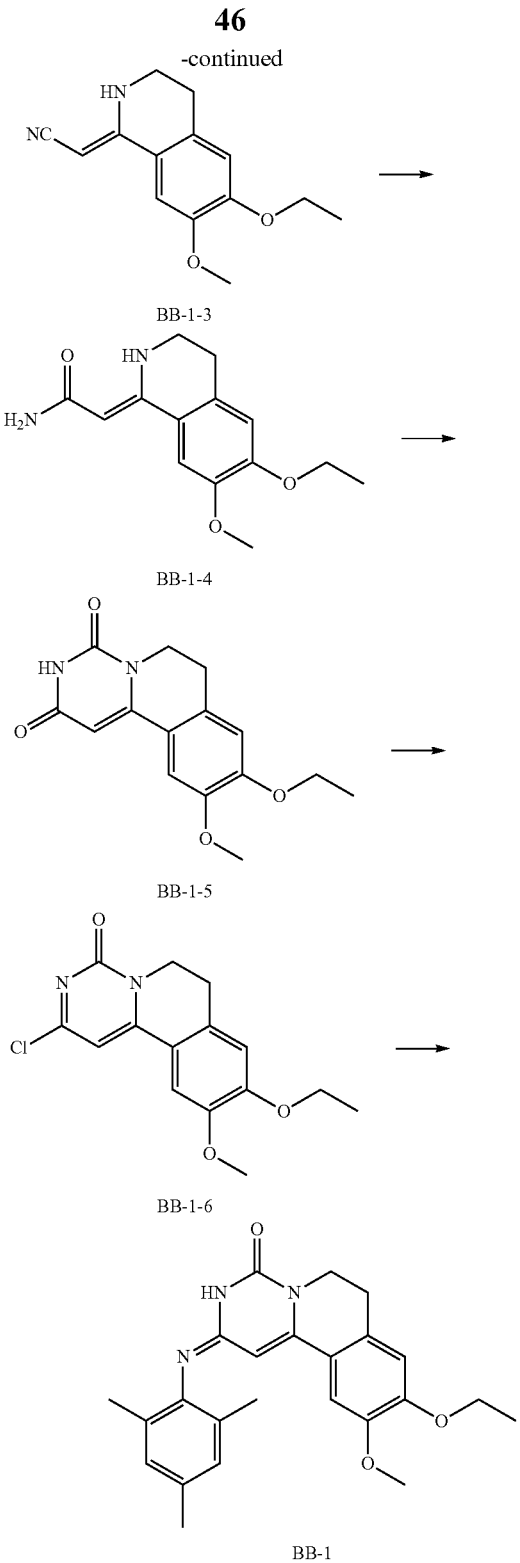

Step 1: Synthesis of Compound BB-1-2

A mixture of compound BB-1-1 (21.10 g) and ethyl cyanoacetate (11.00 g, 10.38 mL) was stirred at 100° C. for 16 hours under nitrogen atmosphere. After the reaction was completed, the mixture was cooled to 70° C. and ethanol (30 mL) was slowly added dropwise, and a large amount of solid was precipitated. The resulting mixture was filtered, and the filter cake was dried under reduced pressure to give product BB-1-2.

$^1$H NMR (400 MHz, DMSO-d6) δ=8.26 (t, J=5.2 Hz, 1H), 6.86 (d, J=8.0 Hz, 1H), 6.79 (br s, 1H), 6.71 (d, 8.0 Hz, 1H), 4.00 (q, J=6.8 Hz, 2H), 3.72 (s, 3H), 3.59 (s, 2H), 3.31-3.23 (m, 2H), 2.64 (t, J=7.2 Hz, 2H), 1.32 (t, J=6.8 Hz, 3H). MS-ESI m/z: 263.1[M+H]$^+$.

Step 2: Synthesis of Compound BB-1-3

Phosphorus oxychloride (379.50 g, 230.00 mL) was heated to 85° C. under nitrogen atmosphere and compound BB-1-2 (26.00 g) was added in portions. The reaction mixture was stirred at 85° C. for 2 hours. After the reaction was completed, most of the phosphorus oxychloride was removed by reduced pressure distillation. To the residue was added dichloromethane (200 mL) and the mixture was washed with water (100 mL×2). The organic phase was dried over anhydrous sodium sulfate, filtered to remove the desiccant, and then concentrated under reduced pressure. The resulting crude product was purified by slurrying with ethyl acetate (20 mL) to give compound BB-1-3.

$^1$H NMR (400 MHz, CD$_3$OD) δ=7.16 (s, 1H), 6.83 (s, 1H), 4.62 (s, 1H), 4.12 (q, J=6.8 Hz, 2H), 3.86 (s, 3H), 3.35 (d, J=6.4 Hz, 2H), 2.84 (t, J=6.4 Hz, 2H), 1.44 (t, J=6.8 Hz, 3H). MS-ESI m/z: 245.1[M+H]$^+$.

Step 3: Synthesis of Compound BB-1-4

Compound BB-1-3 (1.00 g) was added in portions to 98% concentrated sulfuric acid (12.88 g, 128.69 mmol, 7.00 mL) at 0° C. The reaction mixture was stirred at 27° C. for 3 hours. After the reaction was completed, the mixture was added to cold water (15 mL), and then aqueous sodium hydroxide solution (4 mol/L, 32 mL) was added dropwise to adjust the pH to neutral, followed by extraction with ethyl acetate (100 mL×3). Then the organic phases were combined, dried over anhydrous sodium sulfate, filtered to remove the desiccant, and concentrated under reduced pressure to give compound BB-1-4.

MS-ESI m/z: 263.1[M+H]$^+$.

Step 4: Synthesis of Compound BB-1-5

Sodium (2.42 g) was added to ethanol (80 mL) in portions at 0° C. After the mixture was stirred at 28° C. for 0.5 hour, compound BB-1-4 (6.90 g) was added to the solution in portions, and the mixture was stirred at 80° C. for 0.5 hour. Diethyl carbonate (9.32 g, 9.51 mL) was then added in one portion and the mixture was stirred for an additional 5 hours at 80° C. After the reaction was completed, the mixture was cooled to room temperature, ice water (30 mL) was slowly added, and then diluted hydrochloric acid (2 mol/L, 53 mL) was added to adjust the pH to neutral. A large amount of solid was precipitated. The mixture was filtered, and the resulting filter cake was purified by slurrying with ethanol (10 mL) to give compound BB-1-5.

$^1$H NMR (400 MHz, DMSO-d$_6$) δ=11.22 (br s, 1H), 7.35 (s, 1H), 6.95 (s, 1H), 6.22 (s, 1H), 4.09 (q, J=6.8 Hz, 2H), 3.90 (br s, 2H), 3.83 (s, 3H), 2.89 (br s, 2H), 1.35 (t, J=6.8 Hz, 3H). MS-ESI m/z: 289.1[M+H]$^+$.

Step 5: Synthesis of Compound BB-1-6

Compound BB-1-5 (5.00 g) was dissolved in phosphorus oxychloride (30 mL) at room temperature. The reaction mixture was stirred at 100° C. for 16 hours under nitrogen atmosphere. After the reaction was completed, most of the solvent was removed by reduced pressure distillation. Water (100 mL) was added and the resulting mixture was extracted with dichloromethane (150 mL×2). Then the organic phases were combined, dried over anhydrous sodium sulfate, filtered to remove the desiccant, and concentrated under reduced pressure to give compound BB-1-6. MS-ESI m/z: 306.9[M+H]$^+$.

Step 6: Synthesis of Compound BB-1

Compound BB-1-6 (925.67 mg) was dissolved in isopropanol (8 mL) at room temperature, and then 2,4,6-trimethylaniline (2.10 g) was added. The reaction mixture was stirred at 90° C. for 15 hours under nitrogen atmosphere. After the reaction was completed, the mixture was cooled to room temperature and concentrated under reduced pressure, and the resulting residue was purified by slurrying with ethanol (6 mL) to give compound BB-1.

$^1$H NMR (400 MHz, DMSO-d$_6$) δ=8.85 (br s, 1H), 7.27 (s, 1H), 6.97 (s, 1H), 6.90 (s, 2H), 6.45 (s, 1H), 4.10 (q, J=6.8 Hz, 2H), 3.90 (t, J=6.0 Hz, 2H), 3.86 (s, 3H), 2.87 (t, J=6.0 Hz, 2H), 2.45 (s, 3H), 2.11 (s, 6H), 1.37 (t, J=6.8 Hz, 3H). MS-ESI m/z: 406.2[M+H]$^+$.

Example 2

Synthesis of Compound BB-2

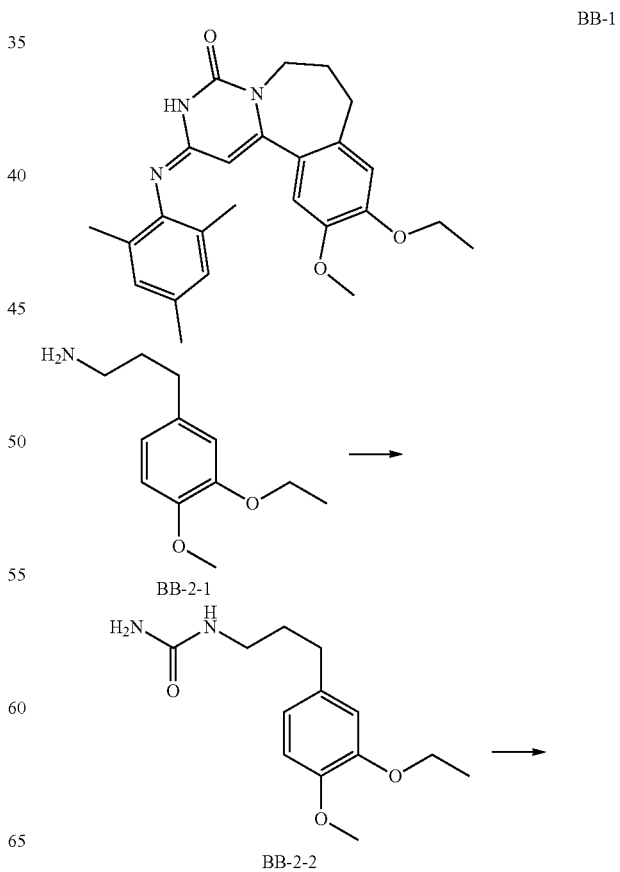

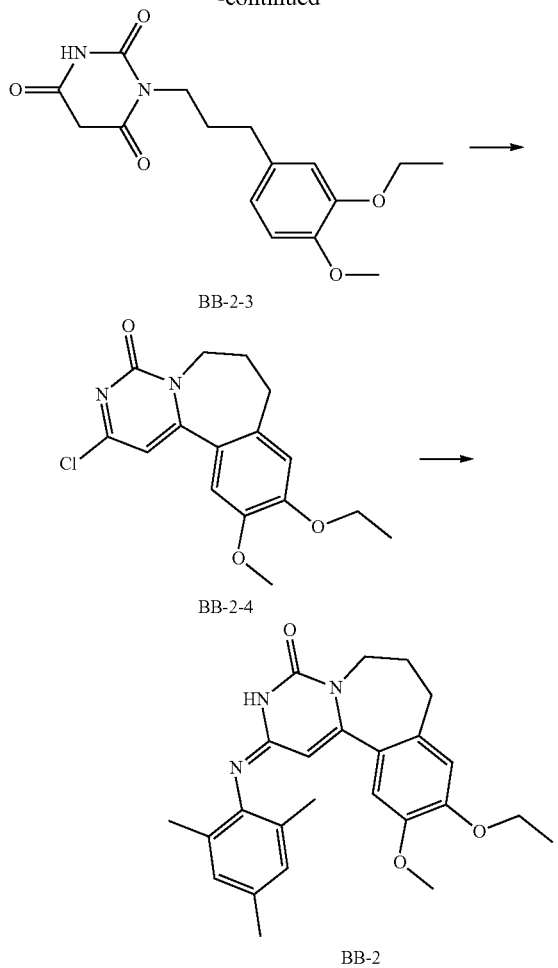

Step 1: Synthesis of Compound BB-2-2

Compound BB-2-1 (8 g) and urea (9.18 g) were dissolved in water (80 mL) at room temperature and then concentrated hydrochloric acid (12 mol/L, 9.56 mL) was added dropwise, and the mixture was stirred at 110° C. for 24 hours. After the reaction was completed, the reaction solution was cooled to room temperature and filtered. Then the filter cake was washed with water (50 mL×2) and dried in vacuum to give compound BB-2-2.

$^1$H NMR (400 MHz, DMSO-$d_6$) δ=6.84 (br d, J=8.0 Hz, 1H), 6.78 (br s, 1H), 6.69 (br d, J=8.0 Hz, 1H), 6.02 (br t, J=5.2 Hz, 1H), 5.43 (br s, 2H), 4.04-3.94 (m, 2H), 3.71 (s, 3H), 2.95 (q, J=6.4 Hz, 2H), 2.50-2.40 (m, 2H), 1.66-1.59 (m, 2H), 1.35-1.25 (m, 3H). MS-ESI m/z: 253.2[M+H]$^+$.

Step 2: Synthesis of Compound BB-2-3

Sodium (6.38 g) was added to anhydrous ethanol (150 mL) in portions under nitrogen atmosphere, and the mixture was stirred until the sodium was completely dissolved to give a freshly prepared sodium ethoxide solution. Compound BB-2-2 (7 g) and diethyl malonate (11.11 g) were added and the mixture was stirred at reflux for 16 hours. The reaction solution was cooled to room temperature and concentrated under reduced pressure to remove ethanol. Water was added to dissolve the residue, and then 2 mol/L hydrochloric acid was added dropwise under an ice bath to adjust the pH to 5. The mixture was filtered with diatomite, and the filtrate was extracted with ethyl acetate (150 mL×2). The organic phases were combined, washed with saturated brine (150 mL), drying over anhydrous sodium sulfate, filtered to remove the desiccant, and concentrated under reduced pressure. The resulting residue was purified by flash silica gel column chromatography (eluent: petroleum ether/ethyl acetate=5/1-1/1; dichloromethane/methanol=50/1-20/1) to give compound BB-2-3.

$^1$H NMR (400 MHz, CD$_3$OD) δ=6.90-6.82 (m, 2H), 6.78-6.72 (m, 1H), 4.07 (q, J=6.8 Hz, 2H), 3.89-3.84 (m, 2H), 3.81 (s, 3H), 3.37 (s, 2H), 2.62 (t, J=7.2 Hz, 2H), 1.94 (q, J=7.2 Hz, 2H), 1.39 (t, J=6.8 Hz, 3H). MS-ESI m/z: 321.2[M+H]$^+$.

Step 3: Synthesis of Compound BB-2-4

The compound BB-2-3 (2.4 g) was added to phosphorus oxychloride (26.40 g) under nitrogen atmosphere, and the mixture was heated to 80° C. and stirred for 12 hours. The reaction solution was cooled to room temperature and concentrated under reduced pressure to remove phosphorus oxychloride so as to give compound BB-2-4, which was used directly in next step. MS-ESI m/z: 321.1[M+H]$^+$.

Step 4: Synthesis of Compound BB-2

To a solution of compound BB-2-4 (2.4 g) in THF (24 mL) was added dropwise a solution of 2,4,6-trimethylaniline (2.02 g) in THF (10 mL) at 20° C. The mixture was stirred at 20° C. for 3 hours, and then heated to 50° C. and stirred for 2 hours. After the reaction was completed, the reaction mixture was concentrated under reduced pressure to remove most of the solvent. The residue was dissolved in ethyl acetate (50 mL), and the mixture was washed with water (50 mL) and saturated brine (50 mL) successively, dried over anhydrous sodium sulfate, filtered to remove the desiccant, and concentrated under reduced pressure. The concentrate was purified by flash silica gel column chromatography (eluent: dichloromethane/methanol=100/1-20/1) to give compound BB-2.

$^1$H NMR (400 MHz, CD$_3$OD) δ=7.26 (s, 1H), 7.11 (br s, 2H), 6.97 (s, 1H), 6.31 (s, 1H), 4.20-4.14 (m, 2H), 4.03-4.01 (m, 2H), 3.95 (s, 3H), 2.84-2.82 (m, 2H), 2.37 (s, 3H), 2.29 (s, 6H), 1.90-1.78 (m, 2H), 1.49-1.42 (m, 3H). MS-ESI m/z: 420.3[M+H]$^+$.

Example 3

Synthesis of Compound BB-3

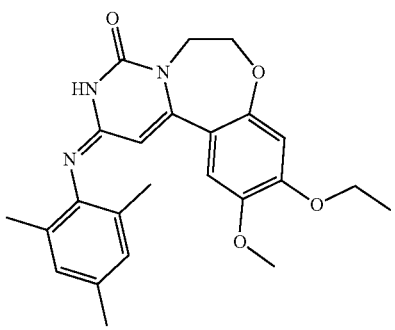

-continued

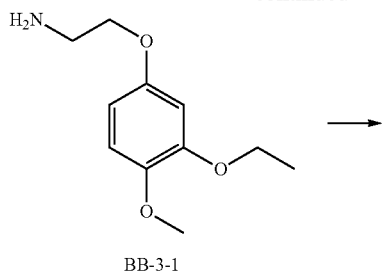

BB-3-1

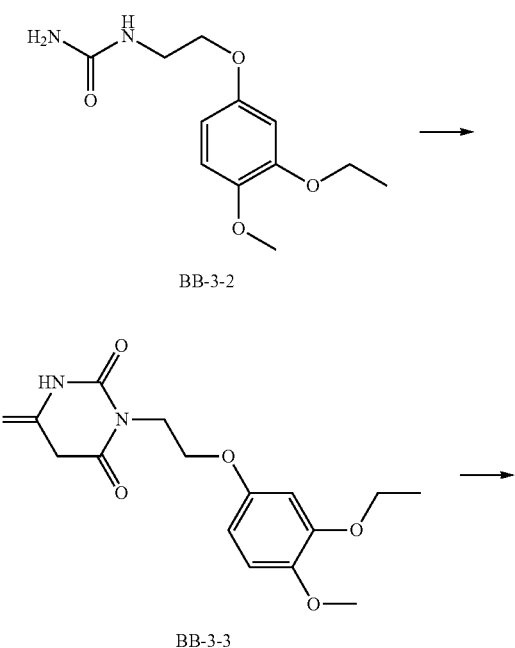

BB-3-2

BB-3-3

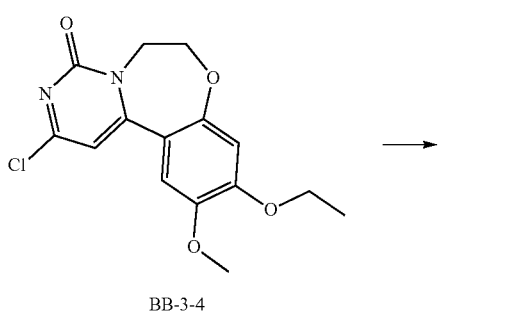

BB-3-4

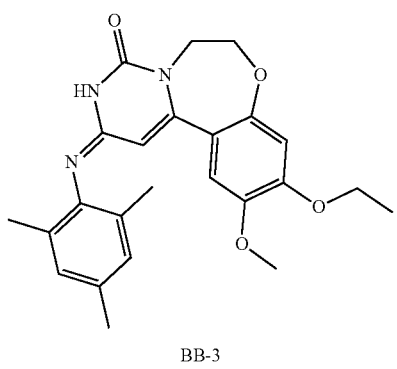

BB-3

Step 1: Synthesis of Compound BB-3-2

Compound BB-3-1 (2 g) was dissolved in 1,2-dichloroethane (20 mL) at room temperature, trimethylsilyl isocyanate (3.82 g) was then added dropwise, and the mixture was heated to 90° C. and stirred for 18 hours. After the reaction was completed, the reaction solution was cooled to room temperature and concentrated under reduced pressure. The resulting residue was slurried with methyl t-butyl ether (10 mL) to give compound BB-3-2.

MS-ESI m/z: 255.1[M+H]$^+$.

Step 2: Synthesis of Compound BB-3-3

Sodium (1.13 g) was added to anhydrous ethanol (85 mL) in portions under nitrogen atmosphere, and the mixture was stirred until the sodium was completely dissolved to give a freshly prepared sodium ethoxide solution.

Compound BB-3-2 (2.5 g) and diethyl malonate (3.94 g) were added and the mixture was stirred at reflux for 12 hours. The reaction solution was cooled to room temperature and concentrated to remove ethanol. Water was added to dissolve the residue and then 2 mol/L hydrochloric acid was added dropwise under an ice bath to adjust the pH to 5. The mixture was filtered with diatomite, and the filtrate was extracted with ethyl acetate (50 mL×2). The organic phases were combined, washed with saturated brine (50 mL), dried over anhydrous sodium sulfate, filtered to remove the desiccant, and concentrated under reduced pressure to give compound BB-3-3.

$^1$H NMR (400 MHz, CD$_3$OD) δ=6.83 (dd, J=8.8 Hz, 2.4 Hz, 1H), 6.58 (d, J=3.2 Hz, 1H), 6.44 (dd, J=8.8 Hz, 3.2 Hz, 1H), 4.19-4.15 (m, 2H), 4.11-4.09 (m, 2H), 4.04-4.00 (m, 2H), 3.76 (s, 3H), 3.35 (s, 2H), 1.39 (t, J=6.8 Hz, 3H). MS-ESI m/z: 323.1[M+H]$^+$.

Step 3: Synthesis of Compound BB-3-4

The compound BB-3-3 (1.3 g) was added to phosphorus oxychloride (12.37 g) under nitrogen atmosphere, and the mixture was heated to 80° C. and stirred for 12 hours. The reaction solution was cooled to room temperature and concentrated under reduced pressure to remove phosphorus oxychloride so as to give compound BB-3-4, which was used directly in next step. MS-ESI m/z: 323.1[M+H]$^+$.

Step 4: Synthesis of Compound BB-3

To a solution of compound BB-3-4 (1.2 g) in THF (20 mL) was added 2,4,6-trimethylaniline (1.01 g) dropwise at 20° C. The mixture was stirred at 25° C. for 12 hours, and then heated to 40° C. and stirred for 3 hours. After the reaction was completed, the reaction mixture was concentrated under reduced pressure to remove most of the solvent. The residue was dissolved in ethyl acetate (50 mL), and the mixture was washed with water (50 mL) and saturated brine (50 mL) successively, dried over anhydrous sodium sulfate, filtered to remove the desiccant, and concentrated under reduced pressure. The concentrate was purified by flash silica gel column chromatography (eluent: dichloromethane/methanol=200/1-30/1) to give compound BB-3.

$^1$H NMR (400 MHz, DMSO-d$_6$) δ=8.89 (s, 1H), 7.11 (s, 1H), 6.92 (br s, 2H), 6.81 (s, 1H), 6.05 (s, 1H), 4.28 (t, J=5.6 Hz, 2H), 4.11-4.04 (m, 4H), 3.84 (s, 3H), 2.26 (s, 3H), 2.13 (br s, 6H), 1.38-1.32 (m, 3H). MS-ESI m/z: 422.2[M+H]$^+$.

Example 4

Synthesis of Compound BB-4

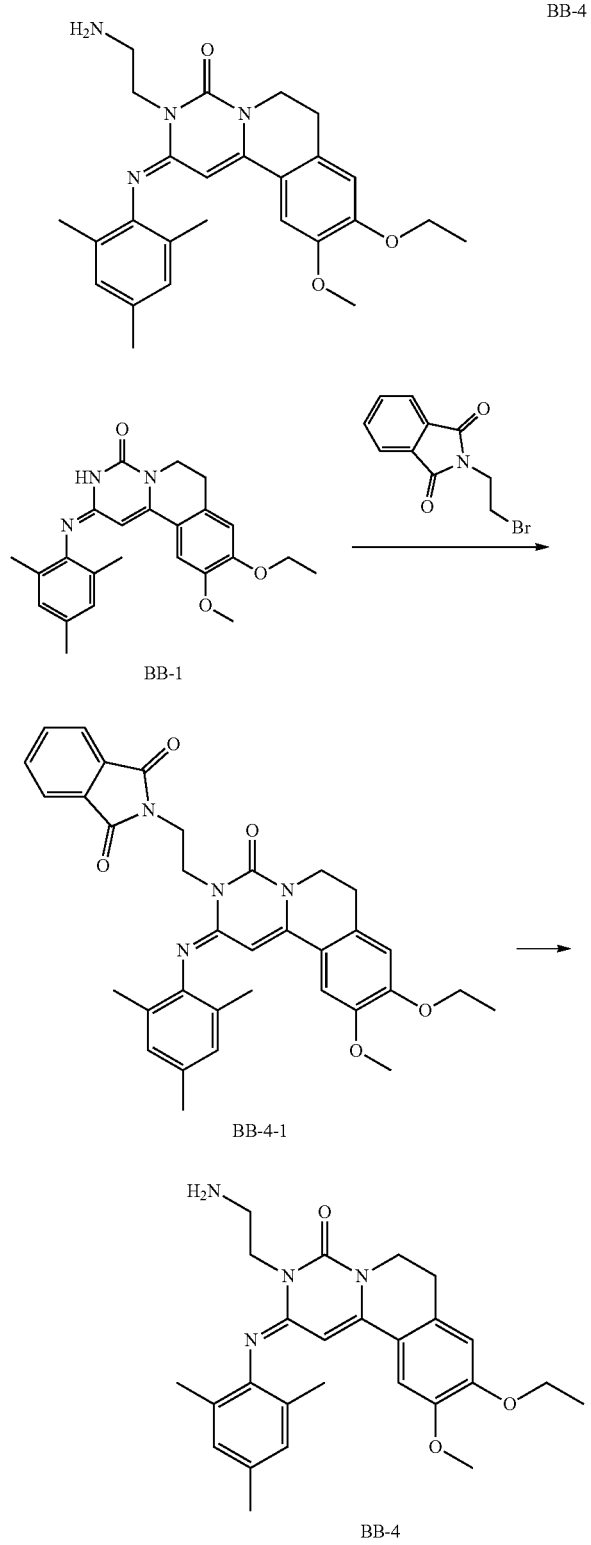

Step 1: Synthesis of Compound BB-4-1

Compound BB-1 (1.00 g) was dissolved in 2-butanone (35 mL) at room temperature, and 2-(2-bromoethyl)isoindoline-1,3-dione (3.76 g), potassium carbonate (3.07 g) and sodium iodide (2.22 g) were added successively. The reaction mixture was stirred at 85° C. for 72 hours under nitrogen atmosphere. After the reaction was completed, the mixture was concentrated to remove most of the organic solvent and then water (30 mL) was added, and the resulting mixture was extracted with ethyl acetate (25 mL×3). The organic phases were combined, dried over anhydrous sodium sulfate, and then filtered to remove the desiccant and concentrated under reduced pressure. The resulting residue was purified by flash silica gel column chromatography (eluent: petroleum ether/ethyl acetate=15/1-3/1) to give compound BB-4-1.

MS-ESI m/z: 579.3[M+H]$^+$.

Step 2: Synthesis of Compound BB-4

Compound BB-4-1 (500.00 mg) was dissolved in trichloromethane (3 mL) and ethanol (3 mL) at room temperature, and hydrazine hydrate (152.67 mg, 85% purity) was added. The mixture was stirred at 28° C. for 16 hours under nitrogen atmosphere. After the reaction was completed, the mixture was concentrated to remove most of the organic solvent and then water (15 mL) was added, and the resulting mixture was extracted with dichloromethane (15 mL×3). Then the organic phases were combined, dried over anhydrous sodium sulfate, filtered to remove the desiccant, and concentrated under reduced pressure to give compound BB-4.

$^1$H NMR (400 MHz, DMSO-d$_6$) δ=6.95 (s, 1H), 6.85 (br s, 2H), 6.66 (s, 1H), 5.31 (s, 1H), 4.14 (t, J=6.8 Hz, 2H), 4.05 (q, J=6.8 Hz, 2H), 3.91 (t, J=6.4 Hz, 2H), 3.62 (s, 3H), 2.90-2.86 (m, 4H), 2.22 (s, 3H), 1.95 (br s, 6H), 1.33 (t, J=6.8 Hz, 3H). MS-ESI m/z: 449.2[M+H]$^+$.

Examples in the following table were synthesized with reference to the synthesis method of Example 4.

| Example | Fragment 1 | Fragment 2 | Structure of compound | Compound number |
|---|---|---|---|---|
| 5 | | BB-2 | | BB-5 |
| 6 | | BB-3 | | BB-6 |

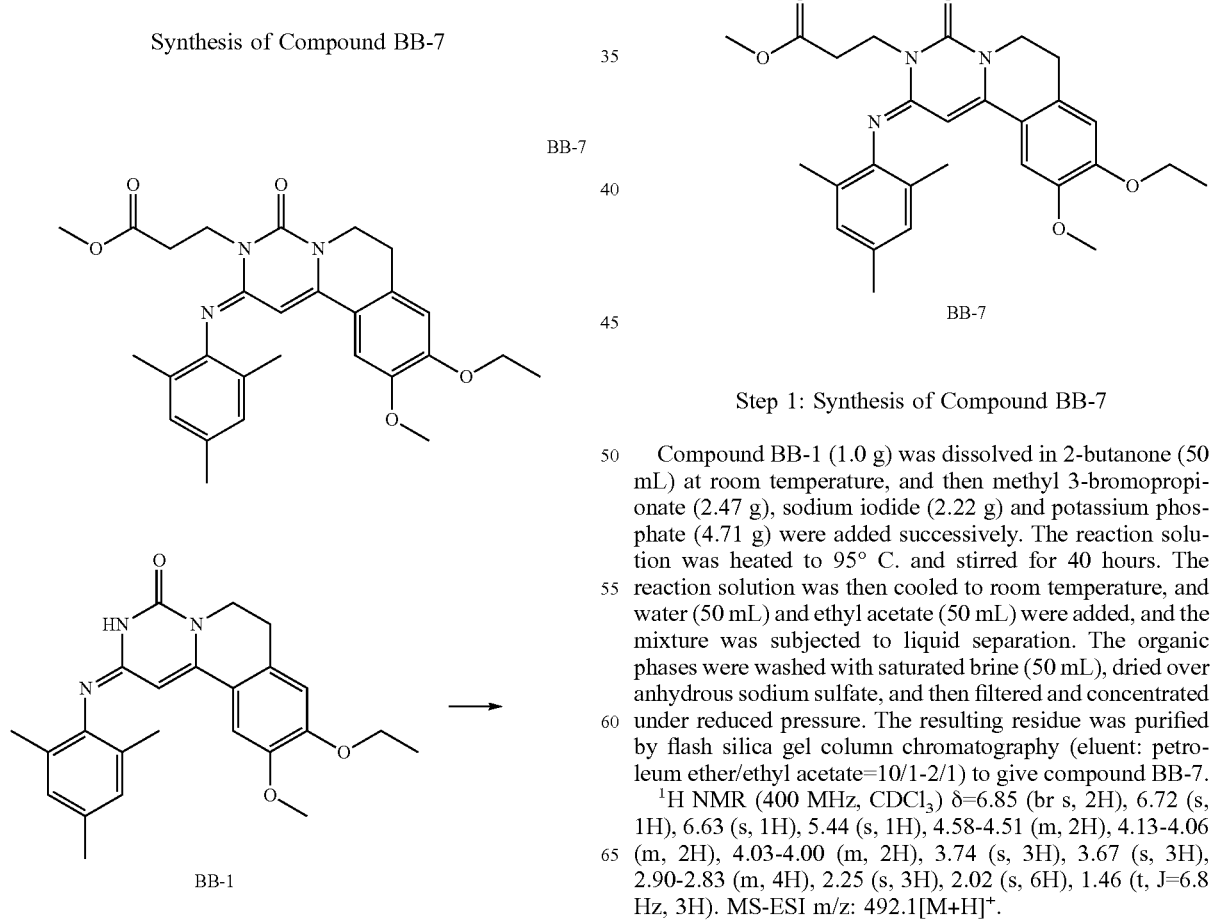

Example 7

Synthesis of Compound BB-7

Step 1: Synthesis of Compound BB-7

Compound BB-1 (1.0 g) was dissolved in 2-butanone (50 mL) at room temperature, and then methyl 3-bromopropionate (2.47 g), sodium iodide (2.22 g) and potassium phosphate (4.71 g) were added successively. The reaction solution was heated to 95° C. and stirred for 40 hours. The reaction solution was then cooled to room temperature, and water (50 mL) and ethyl acetate (50 mL) were added, and the mixture was subjected to liquid separation. The organic phases were washed with saturated brine (50 mL), dried over anhydrous sodium sulfate, and then filtered and concentrated under reduced pressure. The resulting residue was purified by flash silica gel column chromatography (eluent: petroleum ether/ethyl acetate=10/1-2/1) to give compound BB-7.

$^1$H NMR (400 MHz, CDCl$_3$) δ=6.85 (br s, 2H), 6.72 (s, 1H), 6.63 (s, 1H), 5.44 (s, 1H), 4.58-4.51 (m, 2H), 4.13-4.06 (m, 2H), 4.03-4.00 (m, 2H), 3.74 (s, 3H), 3.67 (s, 3H), 2.90-2.83 (m, 4H), 2.25 (s, 3H), 2.02 (s, 6H), 1.46 (t, J=6.8 Hz, 3H). MS-ESI m/z: 492.1[M+H]$^+$.

Example 8

Synthesis of Compound WX001

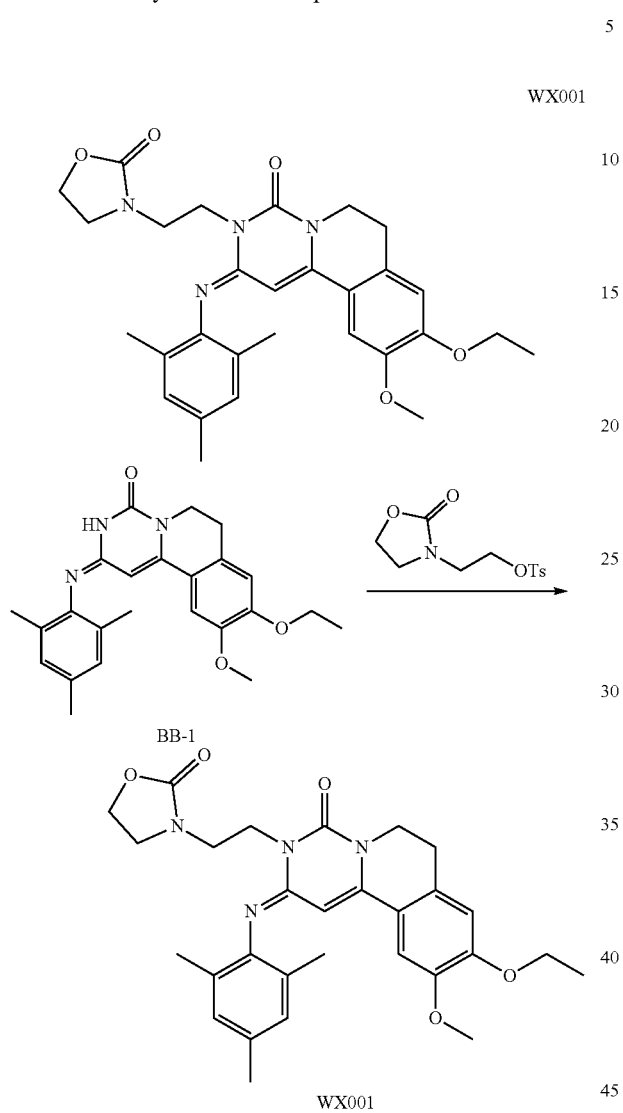

Step 1: Synthesis of Compound WX001

Compound BB-1 (100.00 mg) was dissolved in DMF (2 mL) at room temperature, and 4-methylbenzenesulfonic acid-2-(2-oxazolidinone-3-yl)ethyl ester (422.19 mg), potassium carbonate (306.76 mg) and sodium iodide (221.79 mg) were added successively. The reaction mixture was stirred at 80° C. for 72 hours under nitrogen atmosphere. After the reaction was completed, the reaction mixture was filtered, and the filtrate was concentrated, diluted with water (6 mL) and extracted with ethyl acetate (6 mL×3). The organic phases were combined, dried over anhydrous sodium sulfate, filtered to remove the desiccant, and concentrated under reduced pressure, and the resulting residue was purified by high performance liquid chromatography (HPLC) to give compound WX001.

$^1$H NMR (400 MHz, CDCl$_3$) δ=6.93 (s, 2H), 6.62 (s, 1H), 6.56 (s, 1H), 5.31 (s, 1H), 4.27 (br s, 2H), 4.15-4.01 (m, 6H), 3.91 (br s, 2H), 3.65 (s, 3H), 3.52 (br s, 2H), 2.84 (br s, 2H), 2.26 (s, 3H), 2.15 (br s, 6H), 1.41 (t, J=6.8 Hz, 3H). MS-ESI m/z: 519.0[M+H]$^+$.

Example 9

Synthesis of Compound WX002

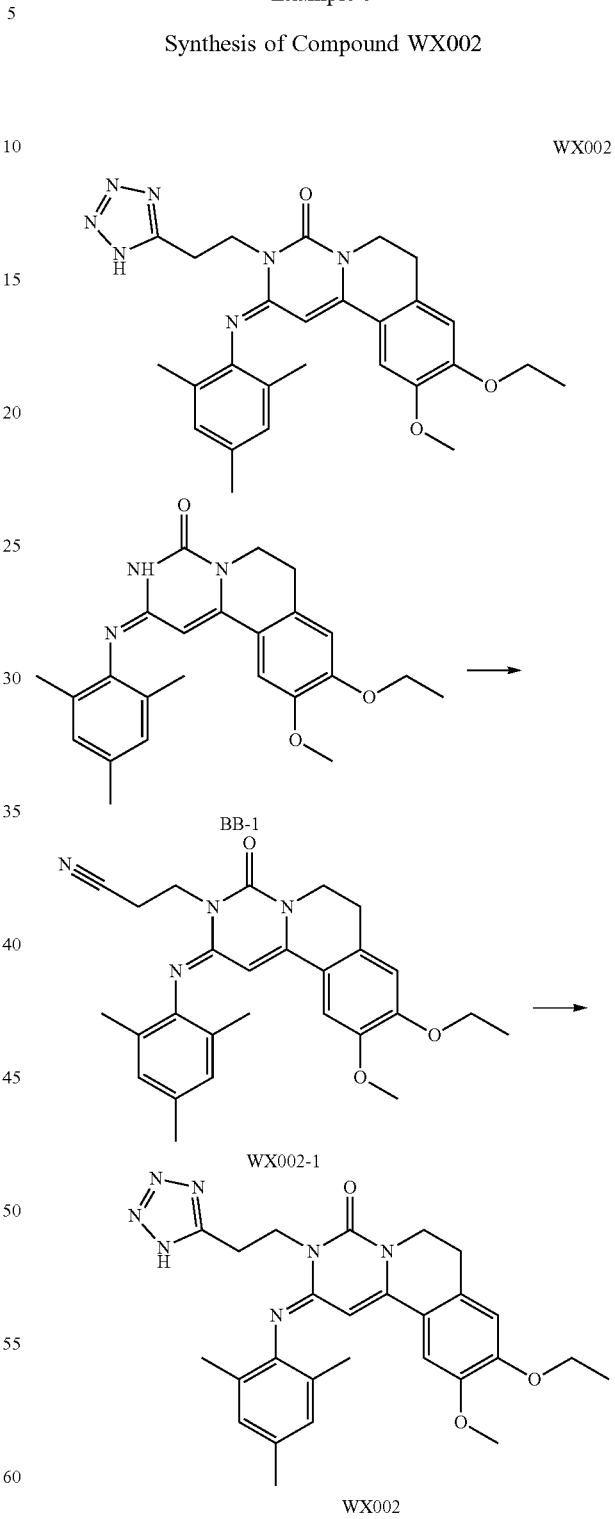

Step 1: Synthesis of Compound WX002-1

Compound BB-1 (4.5 g) was dissolved in 2-butanone (120 mL) at room temperature, and 3-bromopropionitrile (8.92 g), potassium carbonate (13.8 g), and potassium iodide (11.05 g) were added successively. The reaction mixture was stirred at 85° C. for 60 hours under nitrogen atmosphere. After the reaction was completed, the reaction mixture was filtered and the filtrate was concentrated. Then water (100 mL) was added and the resulting mixture was extracted with ethyl acetate (150 mL×3). The organic phases were combined, dried over anhydrous sodium sulfate, and then filtered to remove the desiccant and concentrated under reduced pressure. The resulting residue was purified by silica gel column chromatography (eluent: petroleum ether/ethyl acetate=3/1-1/1) to give compound WX002-1.

$^1$H NMR (400 MHz, CDCl$_3$) δ=6.79 (br s, 2H), 6.66 (s, 1H), 6.59 (s, 1H), 5.39 (s, 1H), 4.51 (t, J=6.8 Hz, 2H), 4.24 (q, J=6.8 Hz, 2H), 3.98 (t, J=6.0 Hz, 2H), 3.70 (s, 3H), 2.90 (t, J=6.8 Hz, 2H), 2.84 (t, J=6.0 Hz, 2H), 2.20 (s, 3H), 1.98 (br s, 6H), 1.41 (t, J=6.8 Hz, 3H). MS-ESI m/z: 459.5[M+H]$^+$.

Step 2: Synthesis of Compound WX002

Compound WX002-1 (160.00 mg) was dissolved in toluene (4 mL) at room temperature, and trimethylsilylmethyl azide (120.60 mg) and dibutyltin oxide (300.00 mg) were added successively. The reaction mixture was stirred at 110° C. for 12 hours under nitrogen atmosphere. After the reaction was completed, the mixture was cooled to 25° C. and concentrated. Then water (5 mL) was added and the resulting mixture was extracted with ethyl acetate (5 mL×3). The organic phases were combined, dried over anhydrous sodium sulfate, filtered to remove the desiccant, and concentrated under reduced pressure, and the resulting residue was purified by HPLC to give compound WX002.

$^1$H NMR (400 MHz, CD$_3$OD) δ=7.18 (br s, 2H), 7.00 (s, 1H), 6.83 (br s, 1H), 5.70 (br s, 1H), 4.76 (t, J=6.8 Hz, 2H), 4.19-4.12 (m, 4H), 3.72 (s, 3H), 3.60 (t, J=6.8 Hz, 2H), 3.06 (t, J=6.8 Hz, 2H), 2.40 (s, 3H), 2.30 (br s, 6H), 1.45 (t, J=6.8 Hz, 3H). MS-ESI m/z: 502.1[M+H]$^+$.

Example 10

Synthesis of Compound WX003

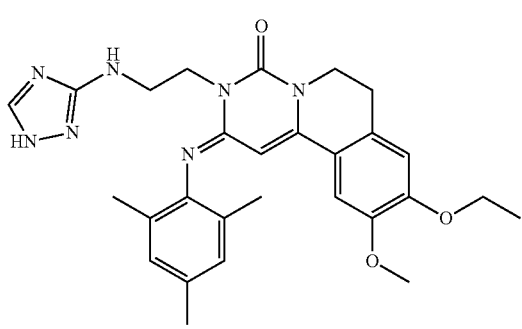

WX003

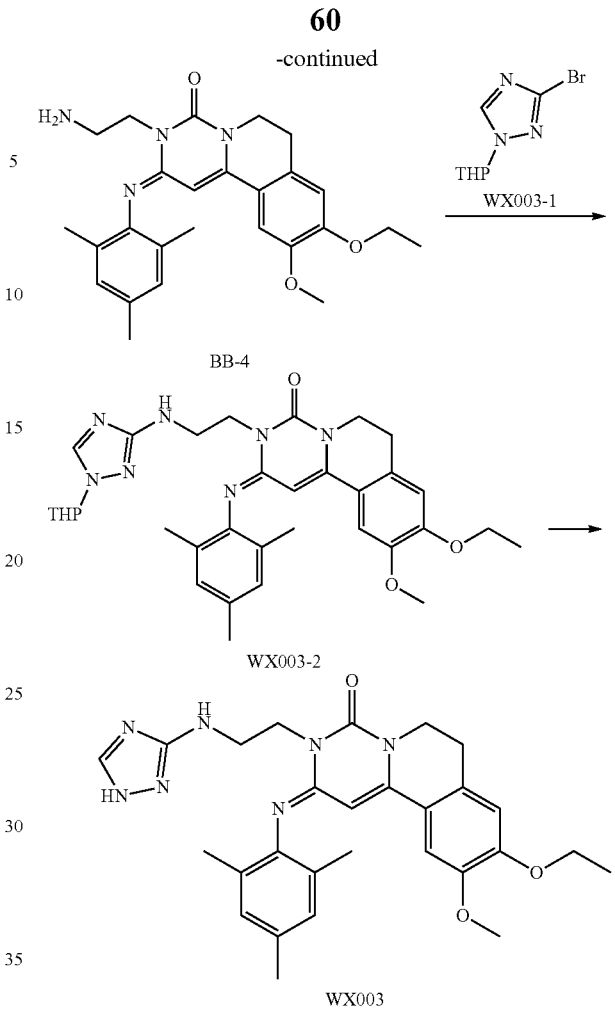

Step 1: Synthesis of Compound WX001-2

Compound BB-4 (500.00 mg) and WX003-1 (413.91 mg) were dissolved in t-butanol (20 mL) at room temperature, and to the above solution were added tris(dibenzylideneacetone)dipalladium (81.66 mg), 2-di-t-butylphosphino-3,4,5,6-tetramethyl-2,4,6-triisopropyl-1,1-biphenyl (85.74 mg) and anhydrous potassium phosphate (378.58 mg). The reaction mixture was stirred at 110° C. for 12 hours under nitrogen atmosphere. After the reaction was completed, the reaction mixture was cooled to room temperature, and water (30 mL) and ethyl acetate (50 mL) were added to quench the reaction. The mixture was subjected to liquid separation to get an organic phase, which was washed with saturated brine (20 mL), dried over anhydrous sodium sulfate, filtered to remove the desiccant, and concentrated under reduced pressure. The resulting residue was purified by flash silica gel column chromatography (eluent: dichloromethane/methanol=50/1-10/1) to give compound WX003-2.

MS-ESI m/z: 600.3[M+H]$^+$.

Step 2: Synthesis of Compound WX003

Compound WX003-2 (0.22 g) and hydrochloric acid-ethyl acetate solution (3 mL, 4 mol/L) were dissolved in ethyl acetate (20 mL) at room temperature. The reaction mixture was stirred at 25° C. for 1 hour under nitrogen atmosphere. The mixture was concentrated under reduced pressure, and the resulting residue was purified by HPLC to give compound WX003.

$^1$H NMR (400 MHz, CD$_3$OD-d$_4$) δ=8.26 (br s, 1H), 7.19 (s, 2H), 7.00 (s, 1H), 6.82 (s, 1H), 5.70 (s, 1H), 4.62 (t, J=6.0 Hz, 2H), 4.21-4.16 (m, 4H), 3.86 (t, J=6.0 Hz, 2H), 3.72 (s, 3H), 3.07 (t, J=6.4 Hz, 2H), 2.40 (s, 3H), 2.31 (s, 6H), 1.45 (t, J=6.8 Hz, 3H). MS-ESI m/z: 516.2[M+H]$^+$.

Examples in the following table were synthesized with reference to the synthesis method of Example 10.

| Example | Fragment 1 | Fragment 2 | Structure of compound | Compound number |
|---|---|---|---|---|
| 11 | 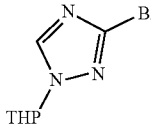 | BB-5 | 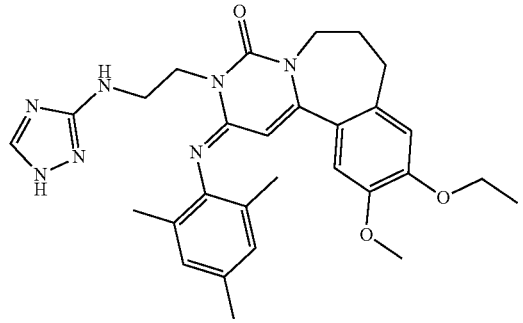 | WX004 |
| 14 | 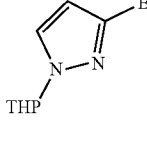 | BB-4 | 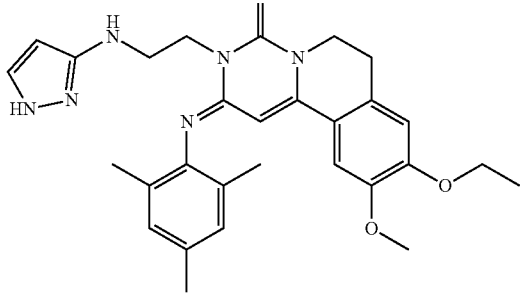 | WX007 |
| 15 | 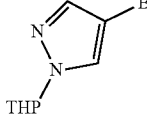 | BB-4 | 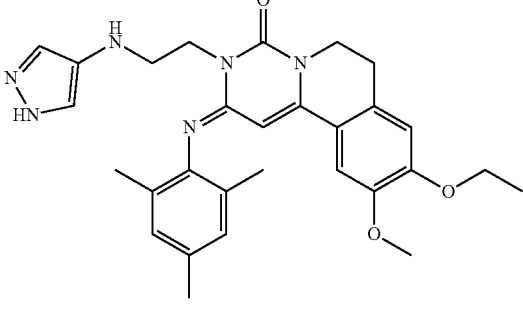 | WX008 |
| 16 | 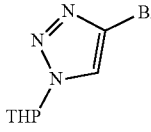 | BB-4 | 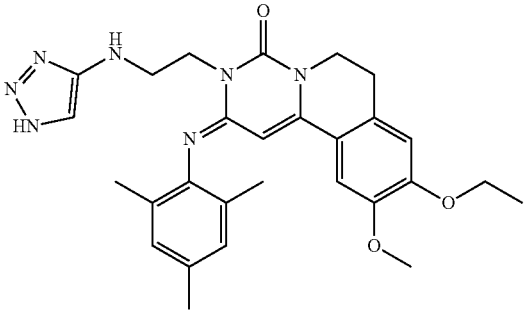 | WX009 |

Example 12

Synthesis of Compound WX005

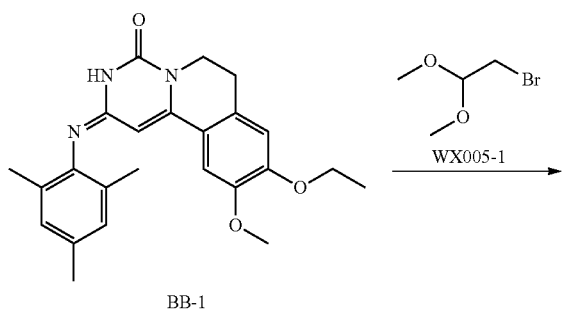

BB-1

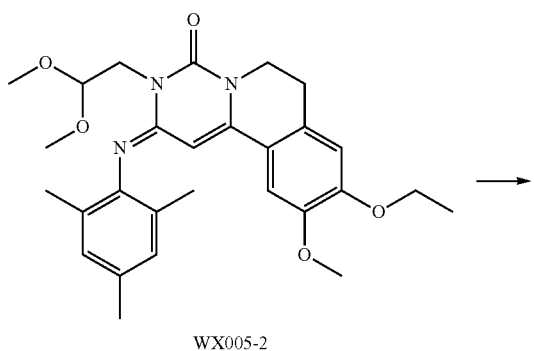

WX005-2

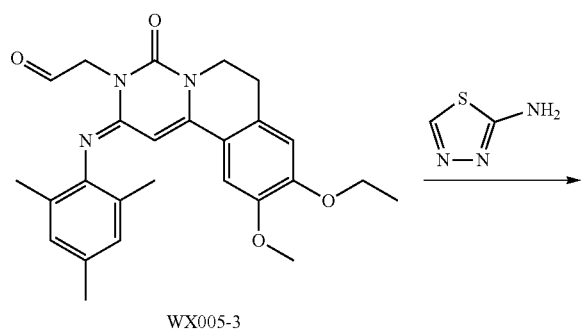

WX005-3

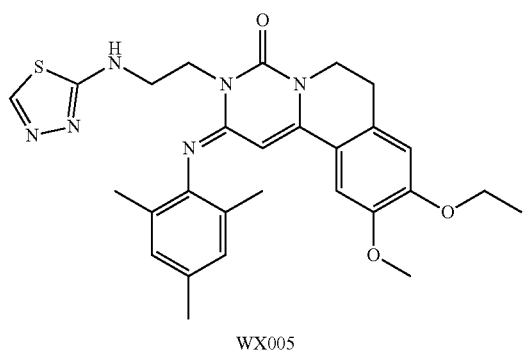

WX005

Step 1: Synthesis of Compound WX005-2

Compound BB-1 (3.22 g) was dissolved in DMF (30 mL) at room temperature, and WX005-1 (9.00 g), potassium carbonate (9.88 g) and sodium iodide (7.14 g) were added successively. The reaction mixture was stirred at 83° C. for 72 hours under nitrogen atmosphere. After the reaction was completed, the mixture was concentrated to remove most of the organic solvent and then water (70 mL) was added, and the resulting mixture was extracted with ethyl acetate (70 mL×3). The organic phases were combined, dried over anhydrous sodium sulfate, and then filtered to remove the desiccant and concentrated under reduced pressure. The resulting residue was purified by flash silica gel column chromatography (eluent: petroleum ether/ethyl acetate=$4/1$-$3/2$) to give compound WX005-2. MS-ESI m/z: 494.3[M+H]$^+$.

Step 2: Synthesis of Compound WX005-3

Compound WX005-2 (0.42 g) and concentrated hydrochloric acid (1 mL, 12 mol/L) were dissolved in 1,4-dioxane (3 mL) at room temperature. The reaction mixture was stirred at 25° C. for 12 hours under nitrogen atmosphere. To the mixture was added saturated aqueous sodium carbonate solution (3 mL) to adjust the pH to 7-8, followed by addition of water (3 mL) and extraction with ethyl acetate (5 mL×3). Then the organic phases were combined, dried over anhydrous sodium sulfate, filtered to remove the desiccant, and concentrated under reduced pressure to give compound WX005-3, which was used directly in next step.

MS-ESI m/z: 448.0[M+H]$^+$.

Step 3: Synthesis of Compound WX005

Compound WX005-3 (100.00 mg) and 2-amino-1,3,4-thiadiazole (45.19 mg) were dissolved in ethanol (2 mL) at room temperature. After being stirred at 78° C. for 12 hours under nitrogen atmosphere, the mixture was cooled to room temperature. NaBH$_4$ (67.62 mg) and methanol (0.5 mL) were added, and the resulting mixture was heated to 78° C. and stirred for an additional 12 hours. Water (1 mL) was added to quench the reaction, and then the mixture was concentrated under reduced pressure. The resulting residue was purified by HPLC to give compound WX005. $^1$H NMR (400 MHz, CDCl$_3$) δ=8.26 (s, 1H), 6.92 (br s, 1H), 6.82 (s, 2H), 6.64 (s, 1H), 6.59 (s, 1H), 5.41 (s, 1H), 4.61-4.54 (m, 2H), 4.08-3.94 (m, 4H), 3.81-3.73 (m, 2H), 3.68 (s, 3H), 2.82 (t, J=6.0 Hz, 2H), 2.22 (s, 3H), 2.00 (s, 6H), 1.41 (t, J=6.8 Hz, 3H). MS-ESI m/z: 533.0[M+H]$^+$ Examples in the following table were synthesized with reference to the synthesis method of Example 12.

| Example | Fragment 1 | Fragment 2 | Structure of compound | Compound number |
|---|---|---|---|---|
| 13 | (methyl-triazole-amine structure) | WX005-3 | (structure) | WX006 |

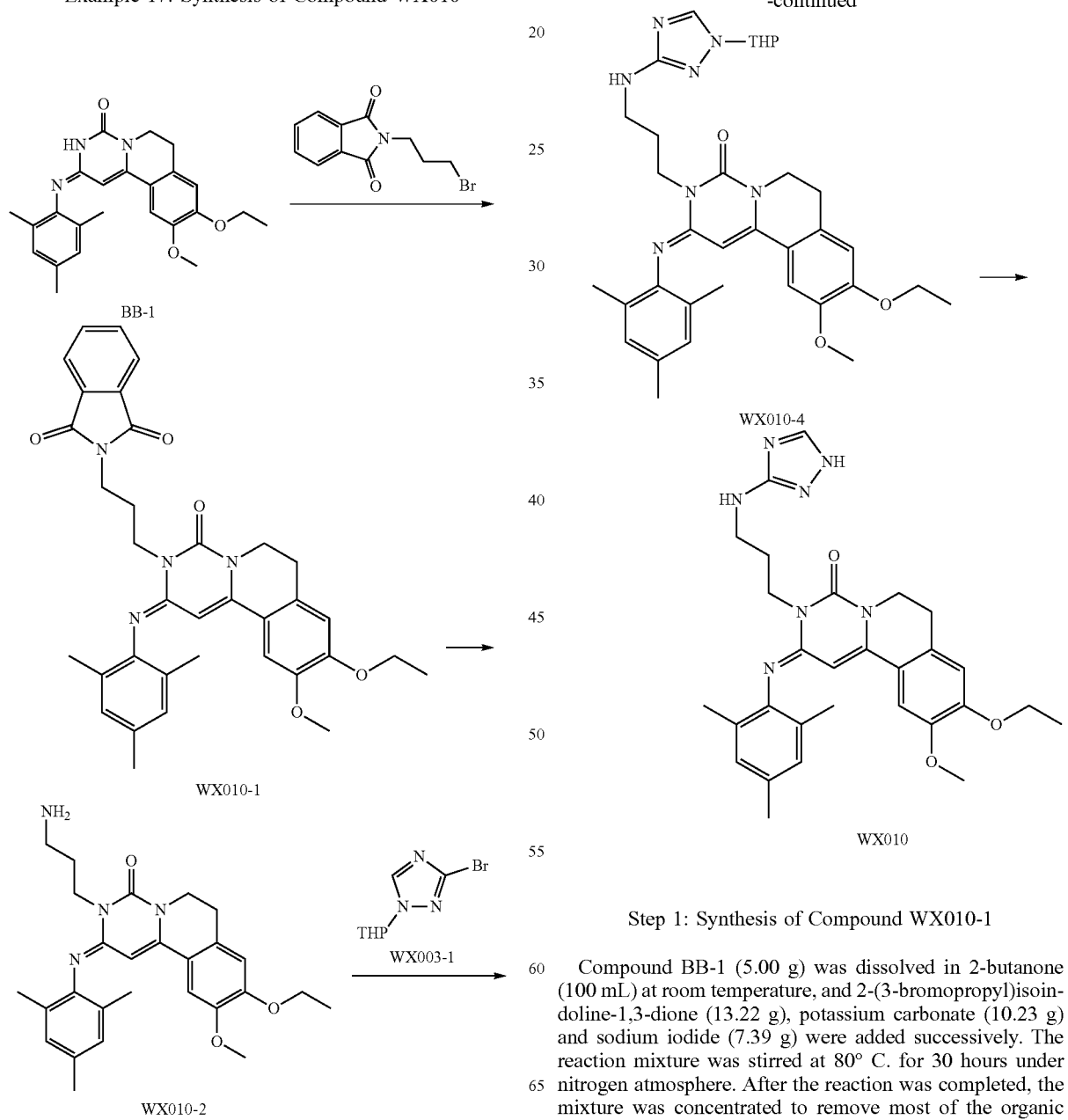

Example 17: Synthesis of Compound WX010

Step 1: Synthesis of Compound WX010-1

Compound BB-1 (5.00 g) was dissolved in 2-butanone (100 mL) at room temperature, and 2-(3-bromopropyl)isoindoline-1,3-dione (13.22 g), potassium carbonate (10.23 g) and sodium iodide (7.39 g) were added successively. The reaction mixture was stirred at 80° C. for 30 hours under nitrogen atmosphere. After the reaction was completed, the mixture was concentrated to remove most of the organic solvent and then water (50 mL) was added, and the resulting mixture was extracted with dichloromethane (50 mL×3). The organic phases were combined, dried over anhydrous sodium sulfate, and then filtered to remove the desiccant and concentrated under reduced pressure. The resulting residue was purified by flash silica gel column chromatography (eluent: petroleum ether/ethyl acetate=5/1-1/1) to give compound WX010-1. MS-ESI m/z: 593.2[M+H]$^+$.

Step 2: Synthesis of Compound WX010-2

Compound WX010-1 (1.30 g) was dissolved in trichloromethane (10 mL) and ethanol (10 mL) at room temperature, and hydrazine hydrate (5.15 g, 85% purity) was added. The mixture was stirred at 70° C. for 10 hours under nitrogen atmosphere. After the reaction was completed, the mixture was concentrated to remove most of the organic solvent and then water (30 mL) was added, and the resulting mixture was extracted with ethyl acetate (15 mL×2). Then the organic phases were combined, dried over anhydrous sodium sulfate, filtered to remove the desiccant, and concentrated under reduced pressure to give compound WX010-2. MS-ESI m/z: 463.2[M+H]$^+$.

Step 3: Synthesis of Compound WX010-4

Compound WX010-2 (900.00 mg) and WX003-1 (903.06 mg) were dissolved in t-butanol (5 mL) at room temperature, and to the above solution were added tris(dibenzylideneacetone)dipalladium (356.32 mg), 2-di-t-butylphosphino-3,4,5,6-tetramethyl-2,4,6-triisopropyl-1,1-biphenyl (187.07 mg) and anhydrous potassium phosphate (825.98 mg). The reaction mixture was stirred at 100° C. for 12 hours under nitrogen atmosphere. After the reaction was completed, the reaction mixture was cooled to the room temperature and filtered. The filtrate was concentrated under reduced pressure, and the resulting residue was purified by flash silica gel column chromatography (eluent: petroleum ether/ethyl acetate=20/1-1/1) to give compound WX010-4. MS-ESI m/z: 614.1[M+H]$^+$.

Step 4: Synthesis of Compound WX010

Compound WX010-4 (1.00 g) and hydrochloric acid-ethyl acetate solution (5 mL, 4 mol/L) were dissolved in ethyl acetate (5 mL) at room temperature. The reaction mixture was stirred at 25° C. for 10 minutes under nitrogen atmosphere. The mixture was concentrated under reduced pressure, and the resulting residue was purified by HPLC to give compound WX010.

$^1$H NMR (400 MHz, CD$_3$OD) δ=8.27 (s, 1H), 7.18 (s, 2H), 6.99 (s, 1H), 6.81 (s, 1H), 5.68 (s, 1H), 4.49 (t, J=6.8 Hz, 2H), 4.25-4.13 (m, 4H), 3.71 (s, 3H), 3.63 (t, J=6.8 Hz, 2H), 3.08 (t, J=6.4 Hz, 2H), 2.40 (s, 3H), 2.32-2.16 (m, 8H), 1.45 (t, J=6.8 Hz, 3H). MS-ESI m/z: 530.1[M+H]$^+$.

Example 18

Synthesis of Compound WX015

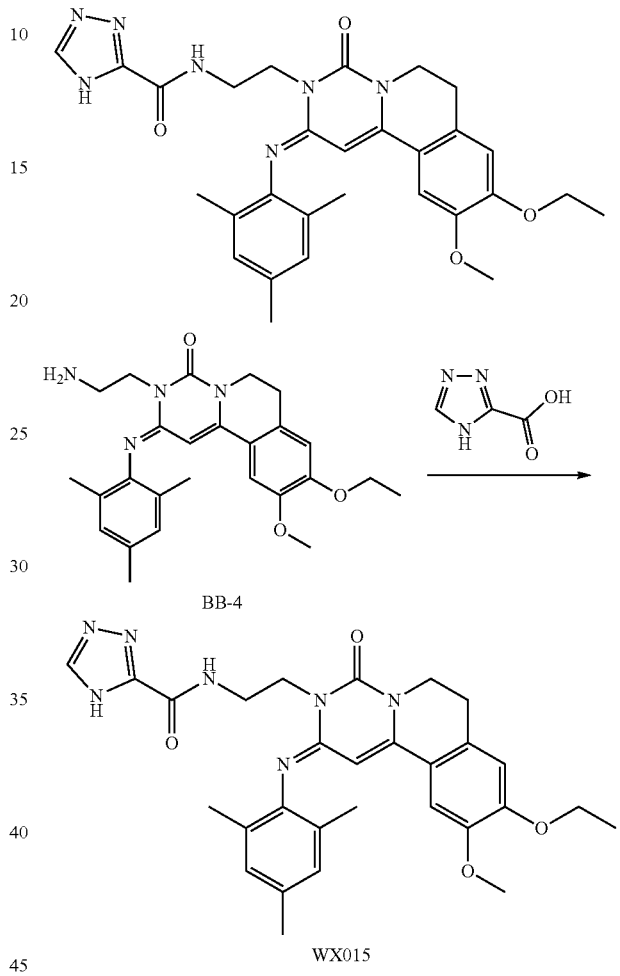

Step 1: Synthesis of Compound WX015

Compound BB-4 (50.0 mg) and 4H-1,2,4-triazole-3-carboxylic acid (12.6 mg) were dissolved in DMF (2 mL) at room temperature, and then HATU (50.86 mg) and DIPEA (28.81 mg) were added. The mixture was stirred at 25° C. for 24 hours. After the reaction was completed, the mixture was concentrated under reduced pressure, and the resulting residue was purified by HPLC to give compound WX015.

$^1$H NMR (400 MHz, CD$_3$OD) δ=8.39 (br s, 1H), 6.91 (s, 2H), 6.85 (s, 1H), 6.76 (s, 1H), 5.50 (s, 1H), 4.54-4.51 (m, 2H), 4.11 (q, J=6.8 Hz, 2H), 3.98 (t, J=6.0 Hz, 2H), 3.90 (t, J=5.6 Hz, 2H), 3.69 (s, 3H), 2.91 (t, J=6.0 Hz, 2H), 2.29 (s, 3H), 2.03 (s, 6H), 1.42 (t, J=6.8 Hz, 3H). MS-ESI m/z: 544.5[M+H]$^+$.

Examples in the following table were synthesized with reference to the synthesis method of Example 18.

| Example | Fragment 1 | Fragment 2 | Structure of compound | Compound number |
|---|---|---|---|---|
| 19 | 1H-1,2,3-triazole-4-carboxylic acid | BB-4 | (structure) | WX016 |
| 20 | 1H-imidazole-2-carboxylic acid | BB-4 | (structure) | WX017 |
| 21 | 1H-pyrazole-5-carboxylic acid | BB-4 | (structure) | WX018 |
| 22 | oxazole-2-carboxylic acid | BB-4 | (structure) | WX019 |

-continued
| Example | Fragment 1 | Fragment 2 | Structure of compound | Compound number |
|---|---|---|---|---|
| 23 | 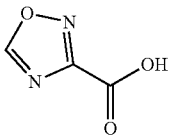 | BB-4 | 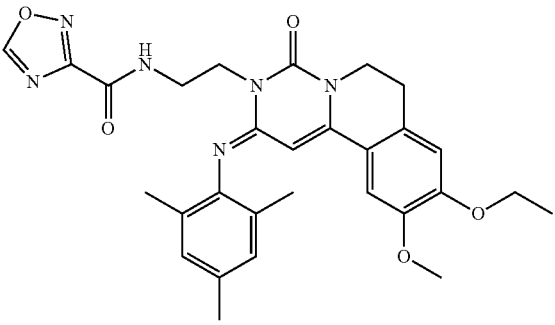 | WX020 |
| 24 | 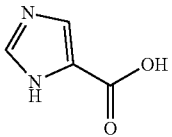 | BB-4 | 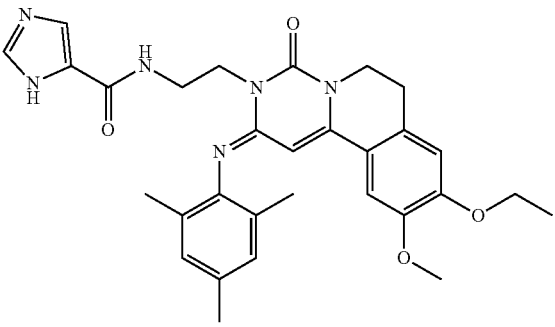 | WX021 |
| 25 | 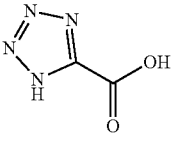 | BB-4 | 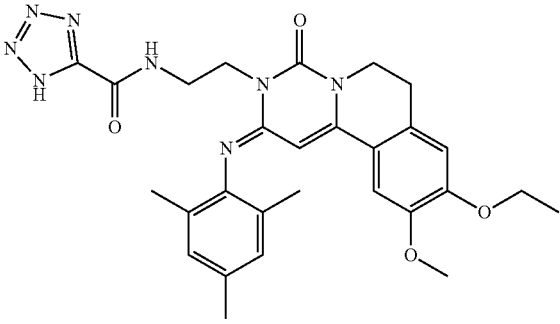 | WX022 |
| 26 | 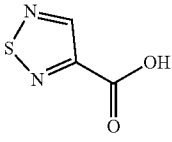 | BB-4 | 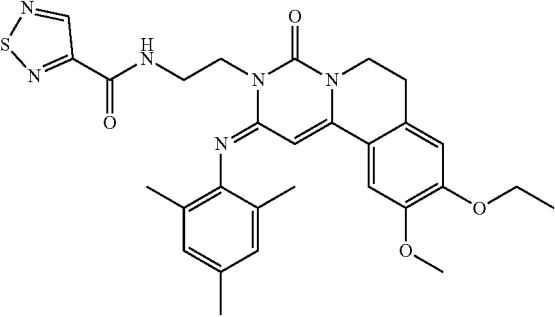 | WX023 |

-continued

| Example | Fragment 1 | Fragment 2 | Structure of compound | Compound number |
|---|---|---|---|---|
| 27 | (4-methyl-1H-1,2,3-triazole-5-carboxylic acid) | BB-4 | | WX024 |
| 28 | (4-amino-1H-1,2,3-triazole-5-carboxylic acid) | BB-4 | | WX025 |
| 29 | (4-methoxy-1H-1,2,3-triazole-5-carboxylic acid) | BB-4 | | WX026 |
| 30 | (4-fluoro-1H-1,2,3-triazole-5-carboxylic acid) | BB-4 | | WX027 |

-continued

| Example | Fragment 1 | Fragment 2 | Structure of compound | Compound number |
|---------|------------|------------|----------------------|-----------------|
| 31 | 5-chloro-1H-1,2,3-triazole-4-carboxylic acid | BB-4 | | WX028 |
| 32 | 5-(trifluoromethyl)-1H-1,2,3-triazole-4-carboxylic acid | BB-4 | | WX029 |
| 33 | 5-carbamoyl-1H-1,2,3-triazole-4-carboxylic acid | BB-4 | | WX030 |
| 34 | 4-(methoxycarbonyl)-1H-1,2,3-triazole-5-carboxylic acid | BB-4 | | WX031 |

-continued

| Example | Fragment 1 | Fragment 2 | Structure of compound | Compound number |
|---------|-----------|-----------|----------------------|-----------------|
| 35 | | BB-4 | | WX032 |
| 36 | | BB-4 | | WX033 |
| 37 | | BB-4 | | WX034 |
| 38 | | BB-4 | | WX035 |

-continued
| Example | Fragment 1 | Fragment 2 | Structure of compound | Compound number |
|---|---|---|---|---|
| 39 | 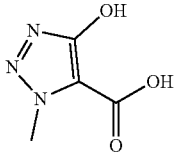 | BB-4 | 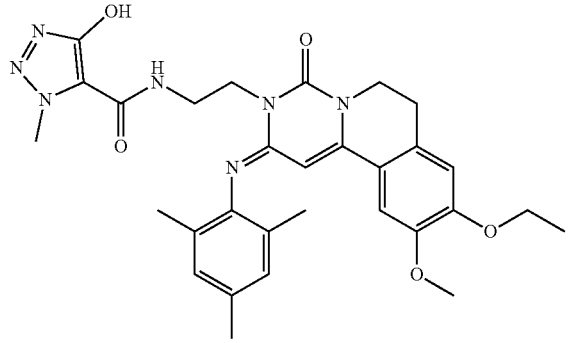 [SMILES: CCOc1cc2c(cc1OC)-c1c/c(=N\c3c(C)cc(C)cc3C)n(CCNC(=O)c3c(O)nnn3C)c(=O)n1CC2] | WX036 |
| 40 | 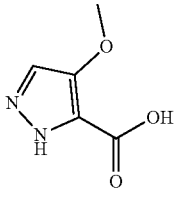 | BB-4 | 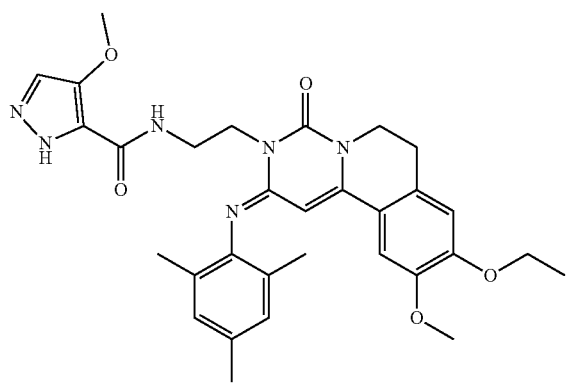 [SMILES: CCOc1cc2c(cc1OC)-c1c/c(=N\c3c(C)cc(C)cc3C)n(CCNC(=O)c3[nH]ncc3OC)c(=O)n1CC2] | WX037 |
| 41 | 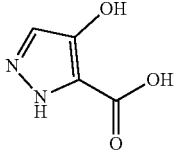 | BB-4 | 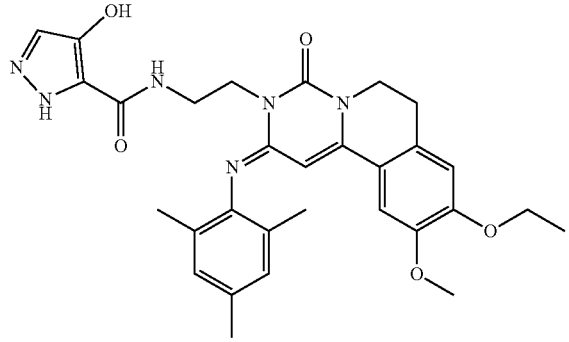 [SMILES: CCOc1cc2c(cc1OC)-c1c/c(=N\c3c(C)cc(C)cc3C)n(CCNC(=O)c3[nH]ncc3O)c(=O)n1CC2] | WX038 |
| 42 | 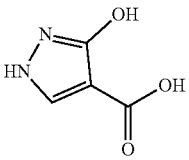 | BB-4 | 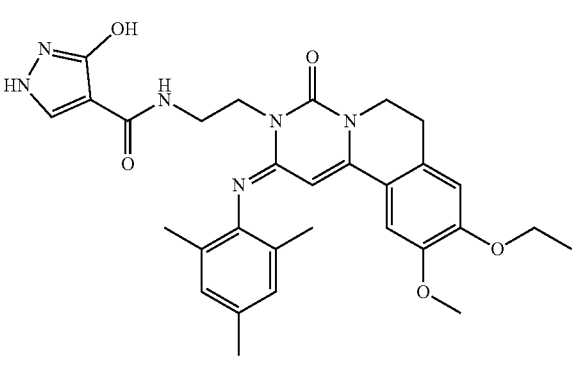 [SMILES: CCOc1cc2c(cc1OC)-c1c/c(=N\c3c(C)cc(C)cc3C)n(CCNC(=O)c3c[nH]nc3O)c(=O)n1CC2] | WX039 |

-continued

| Example | Fragment 1 | Fragment 2 | Structure of compound | Compound number |
|---|---|---|---|---|
| 43 | 4-hydroxyisoxazole-3-carboxylic acid | BB-4 | | WX040 |
| 44 | 3-methoxy-1H-pyrazole-4-carboxylic acid | BB-4 | | WX041 |
| 45 | 5-hydroxy-1H-imidazole-4-carboxylic acid | BB-4 | | WX042 |
| 46 | 2-hydroxy-1H-imidazole-5-carboxylic acid | BB-4 | | WX043 |

-continued

| Example | Fragment 1 | Fragment 2 | Structure of compound | Compound number |
|---------|------------|------------|----------------------|-----------------|
| 47 | 3-hydroxyisoxazole-5-carboxylic acid | BB-4 | | WX044 |
| 48 | 5-hydroxy-4H-1,2,4-triazole-3-carboxylic acid | BB-4 | | WX045 |
| 49 | 4-amino-1,2,5-thiadiazole-3-carboxylic acid | BB-4 | | WX046 |
| 50 | 4H-1,2,4-triazole-3-carboxylic acid | BB-5 | | WX047 |

| Example | Fragment 1 | Fragment 2 | Structure of compound | Compound number |
|---|---|---|---|---|
| 51 | 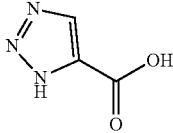 | BB-5 | 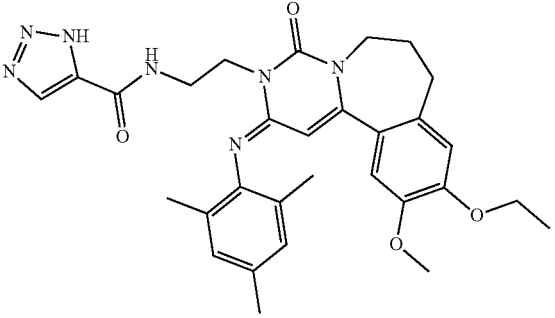 [SMILES: CCOc1cc2c(cc1OC)-c1c/c(=N\c3c(C)cc(C)cc3C)n(CCNC(=O)c3cnn[nH]3)c(=O)n1CCC2] | WX048 |
| 52 | 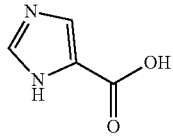 | BB-5 | 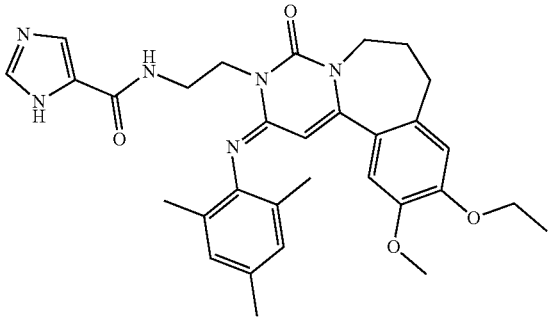 [SMILES: CCOc1cc2c(cc1OC)-c1c/c(=N\c3c(C)cc(C)cc3C)n(CCNC(=O)c3cnc[nH]3)c(=O)n1CCC2] | WX049 |
| 53 | 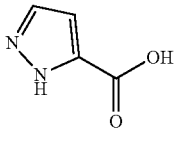 | BB-5 | 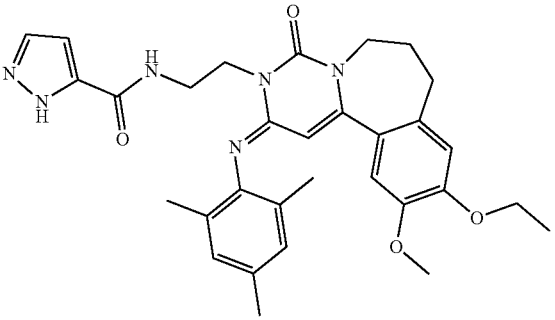 [SMILES: CCOc1cc2c(cc1OC)-c1c/c(=N\c3c(C)cc(C)cc3C)n(CCNC(=O)c3ccn[nH]3)c(=O)n1CCC2] | WX050 |
| 54 | 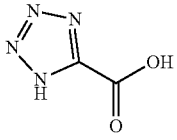 | BB-5 | 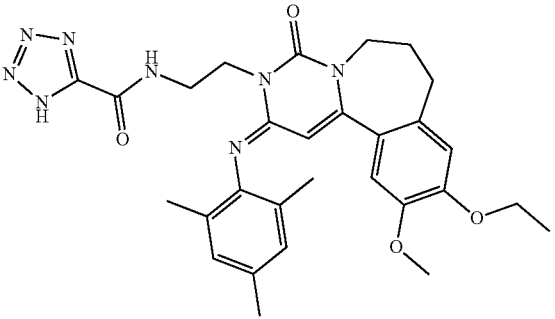 [SMILES: CCOc1cc2c(cc1OC)-c1c/c(=N\c3c(C)cc(C)cc3C)n(CCNC(=O)c3nnn[nH]3)c(=O)n1CCC2] | WX051 |

| Example | Fragment 1 | Fragment 2 | Structure of compound | Compound number |
|---|---|---|---|---|
| 55 | | BB-6 | | WX052 |
| 56 | | BB-6 | | WX053 |

Example 57: Synthesis of Compound WX054

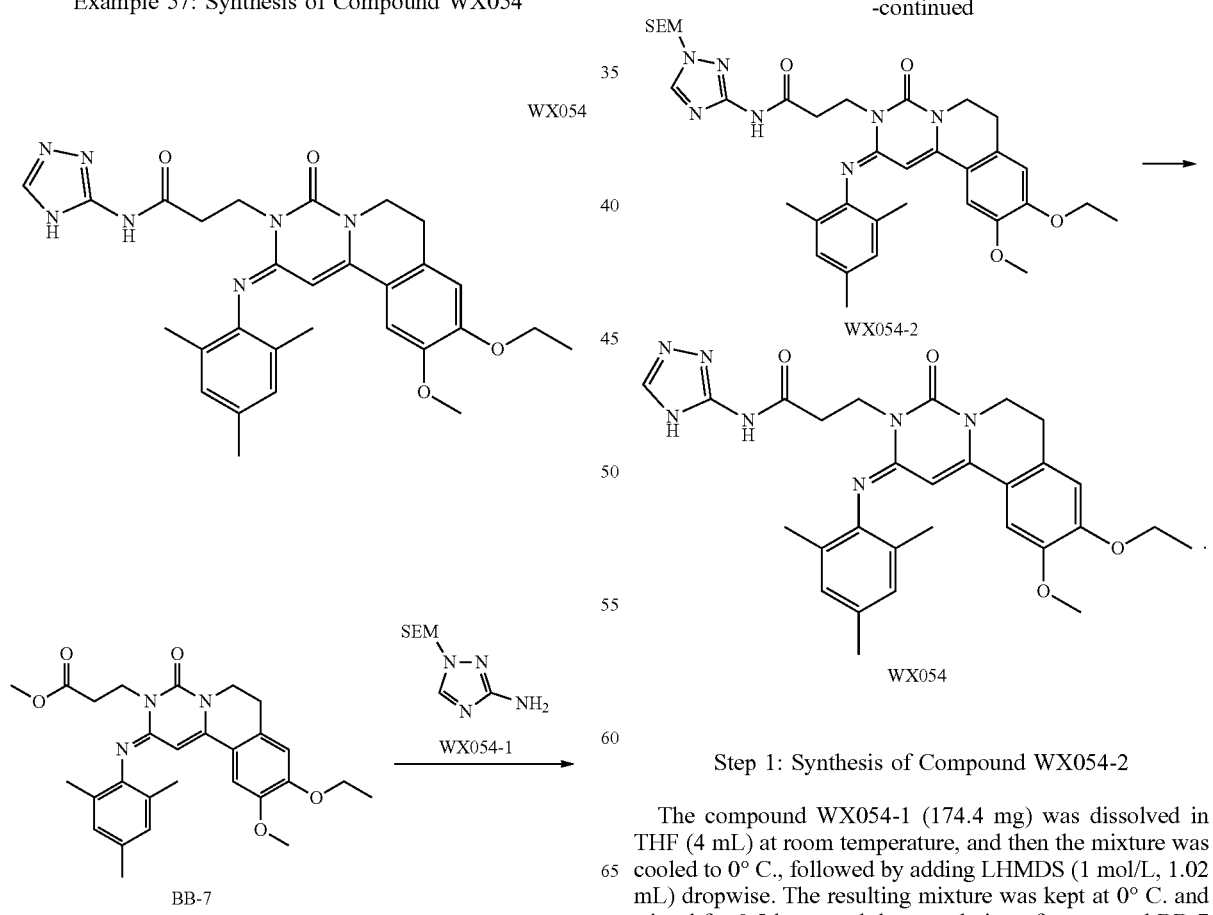

Step 1: Synthesis of Compound WX054-2

The compound WX054-1 (174.4 mg) was dissolved in THF (4 mL) at room temperature, and then the mixture was cooled to 0° C., followed by adding LHMDS (1 mol/L, 1.02 mL) dropwise. The resulting mixture was kept at 0° C. and stirred for 0.5 hour, and then a solution of compound BB-7

(200 mg) in THF (2 mL) was added dropwise. Then the mixture was allowed to warm to 30° C. naturally after the addition, and stirred for an additional 2 hours. The reaction was quenched with water (10 mL), and ethyl acetate (10 mL×3) was added for extraction. The organic phases were combined, washed successively with water (10 mL) and saturated brine (10 mL), dried over anhydrous sodium sulfate, filtered, and concentrated under reduced pressure, and the resulting residue was purified by HPLC to give compound WX054-2.

MS-ESI m/z: 674.6[M+H]$^+$.

Step 2: Synthesis of Compound WX054

Compound WX054-2 (20 mg) was dissolved in dichloromethane (5 mL) under nitrogen atmosphere, and then trifluoroacetic acid (1.54 g) was added, and the mixture was stirred at 25° C. for 3 hours. After the reaction was completed, the mixture was concentrated under reduced pressure to remove most of the solvent, and the resulting residue was purified by HPLC to give compound WX054.

$^1$H NMR (400 MHz, CD$_3$OD) δ=8.75 (br s, 1H), 7.14 (s, 2H), 6.96 (s, 1H), 6.77 (s, 1H), 5.65 (s, 1H), 4.70-4.62 (m, 2H), 4.20-4.10 (m, 4H), 3.68 (s, 3H), 3.20-3.10 (m, 2H), 3.04 (t, J=6.4 Hz, 2H), 2.36 (s, 3H), 2.26 (s, 6H), 1.41 (t, J=6.8 Hz, 3H). MS-ESI m/z: 544.3[M+H]$^+$.

Examples in the following table were synthesized with reference to the synthesis method of Example 57.

| Example | Fragment 1 | Fragment 2 | Structure of compound | Compound number |
|---|---|---|---|---|
| 58 | (triazole-SEM-NH$_2$) | BB-7 | (structure) | WX055 |
| 59 | (oxazole-NH$_2$) | BB-7 | (structure) | WX056 |
| 60 | (SEM-pyrazole-NH$_2$) | BB-7 | (structure) | WX057 |

Example 61

Synthesis of Compound WX058

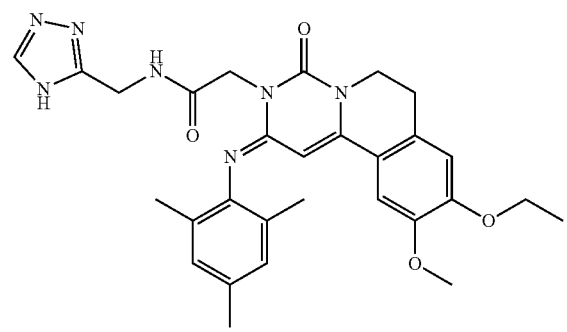

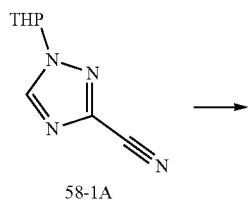

58-1A

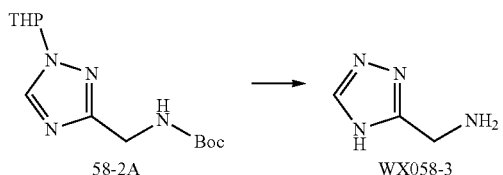

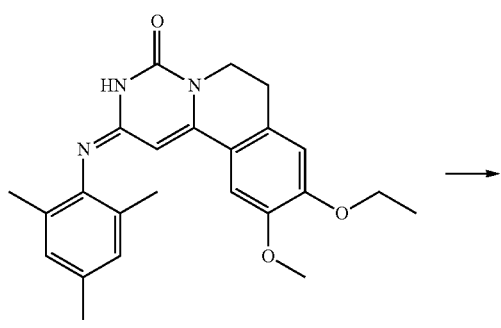

BB-1

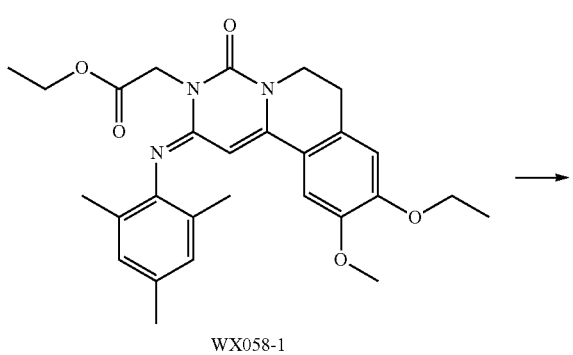

WX058-1

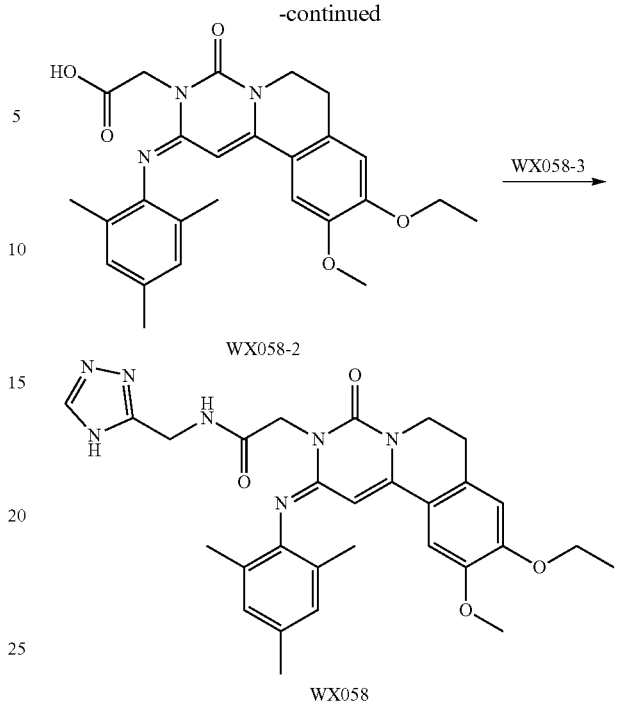

WX058-2

WX058

Step 1: Synthesis of Compound WX058-1

Compound BB-1 (5.00 g) was dissolved in 2-butanone (20 mL) at room temperature, and then ethyl 2-bromoacetate (4.12 g), sodium iodide (0.37 g) and potassium carbonate (3.41 g) were added successively. The reaction solution was stirred at 80° C. for 12 hours. The reaction solution was cooled to room temperature, diluted with dichloromethane (50 mL) and filtered. The filtrate was concentrated under reduced pressure, and the resulting residue was purified by flash silica gel column chromatography (eluent: petroleum ether/ethyl acetate=100/1–10/1) to give compound WX058-1.

$^1$H NMR (400 MHz, CDCl$_3$) δ=6.77 (s, 2H), 6.69 (s, 1H), 6.58 (s, 1H), 5.42 (s, 1H), 4.93 (br s, 2H), 4.16 (q, J=7.2 Hz, 2H), 4.05-3.96 (m, 4H), 3.69 (s, 3H), 2.82 (t, J=6.0 Hz, 2H), 2.19 (s, 3H), 1.93 (s, 6H), 1.40 (t, J=7.2 Hz, 3H), 1.21 (t, J=7.2 Hz, 3H).

Step 2: Synthesis of Compound WX058-2

Compound WX058-1 (0.30 g) was dissolved in ethanol (10 mL), water (4 mL) and tetrahydrofuran (6 mL) at room temperature, and then lithium hydroxide monohydrate (0.10 g) was added. The reaction solution was stirred at 25° C. for 8 hours. Then the reaction solution was concentrated under reduced pressure, followed by adding of water (10 mL). The aqueous phase was adjusted to pH=3-4 with 4 mol/L HCl, and solid was precipitated. The mixture was filtered and dried to give compound WX058-2. MS-ESI m/z: 464.2[M+H]$^+$.

Step 3: Synthesis of Compound WX058-3

Compound 58-1A (2.50 g) was dissolved in ethyl acetate (20 mL) at room temperature, followed by successive addition of (Boc)$_2$O (9.19 g), glacial acetic acid (8 mL) and Pd/C (0.25 g, 10% purity), and the reaction solution was stirred at 30° C. for 12 hours under 25 psi hydrogen atmosphere. Then the reaction solution was filtered and the filtrate was concentrated under reduced pressure, and the resulting residue was purified by flash silica gel column chromatography (eluent: petroleum ether/ethyl acetate=10/1–2/1) to give compound 58-2A.

¹H NMR (400 MHz, CDCl₃) δ=8.20 (s, 1H), 5.42-5.39 (m, 1H), 5.24 (br s, 1H), 4.44 (d, J=5.2 Hz, 2H), 4.08-4.06 (m, 1H), 3.74-3.70 (m, 1H), 2.10-2.04 (m, 4H), 1.70-1.63 (m, 2H), 1.46 (s, 9H).

Compound 58-2A (0.60 g) and hydrochloric acid-ethyl acetate solution (1 mL, 4 mol/L) were dissolved in ethyl acetate (2 mL) at room temperature. The reaction mixture was stirred at 30° C. for 30 minutes under nitrogen atmosphere. The solid was precipitated. The mixture was filtered, and the filter cake was washed with ethyl acetate (2 mL) and dried to give compound WX058-3. ¹H NMR (400 MHz, CD₃OD) δ=9.06 (s, 1H), 4.39 (s, 2H).

Step 4: Synthesis of Compound WX058

Compound WX058-2 (0.15 g) and WX058-3 (0.43 g) were dissolved in DMF (2 mL) at room temperature, followed by successive addition of triethylamine (0.1 mL) and HATU (0.18 g), and the reaction solution was stirred at 30° C. for 10 hours, then poured into water (20 mL), and extracted with ethyl acetate (20 mL×2). The organic phases were combined, dried over anhydrous sodium sulfate, filtered to remove the desiccant, and concentrated under reduced pressure, and the resulting residue was purified by HPLC to give compound WX058.

¹H NMR (400 MHz, CD₃OD) δ=8.64 (s, 1H), 7.14 (s, 2H), 6.99 (s, 1H), 6.83 (s, 1H), 5.70 (s, 1H), 5.18 (s, 2H), 4.69 (s, 2H), 4.28-4.11 (m, 4H), 3.71 (s, 3H), 3.07 (t, J=6.4 Hz, 2H), 2.38 (s, 3H), 2.22 (br s, 6H), 1.53-1.39 (m, 3H). MS-ESI m/z: 544.1[M+H]⁺.

Example 62: Synthesis of Compound WX059

WX059

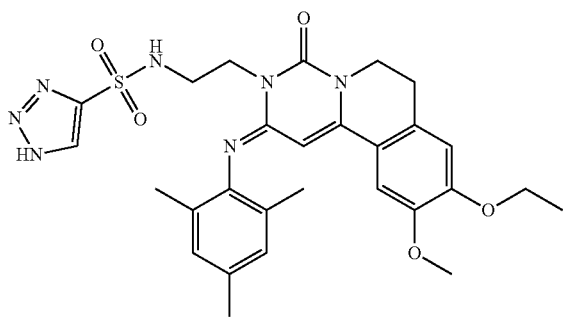

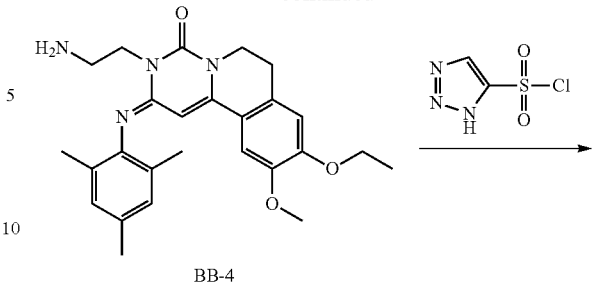

BB-4

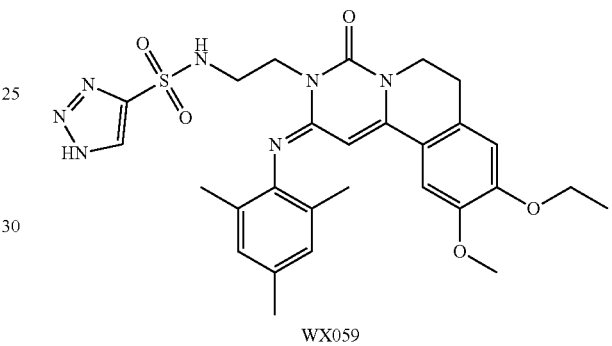

WX059

Step 1: Synthesis of Compound WX059

Compound BB-4 (30 mg) and 1H-1,2,3-triazole-5-sulfonyl chloride (22.42 mg) were dissolved in DMF (1 mL) at room temperature, followed by addition of triethylamine (13.54 mg), and the mixture was stirred at 20° C. After the reaction was completed, the mixture was poured into saturated brine (30 mL) and extracted with ethyl acetate (15 mL×3). The organic phases were combined, washed once with water (50 mL) and saturated brine (50 mL) successively, dried over anhydrous sodium sulfate and filtered to remove the desiccant. The filtrate was concentrated under reduced pressure, and the resulting residue was purified by HPLC to give compound WX059.

¹H NMR (400 MHz, CD₃OD) δ=8.29 (br s, 1H), 7.14 (br s, 2H), 6.98 (s, 1H), 6.79 (s, 1H), 5.66 (s, 1H), 4.51 (br s, 2H), 4.24-4.10 (m, 4H), 3.70 (s, 3H), 3.64 (br s, 2H), 3.06 (br s, 2H), 2.37 (s, 3H), 2.29 (s, 6H), 1.43 (t, J=6.8 Hz, 3H). MS-ESI m/z: 580.0[M+H]⁺.

Examples in the following table were synthesized with reference to the synthesis method of Example 62.

| Example | Fragment 1 | Fragment 2 | Structure of compound | Compound number |
|---|---|---|---|---|
| 63 | (imidazole sulfonyl chloride structure) | BB-4 | (WX060 structure) | WX060 |

Example 64: Synthesis of Compound WX064

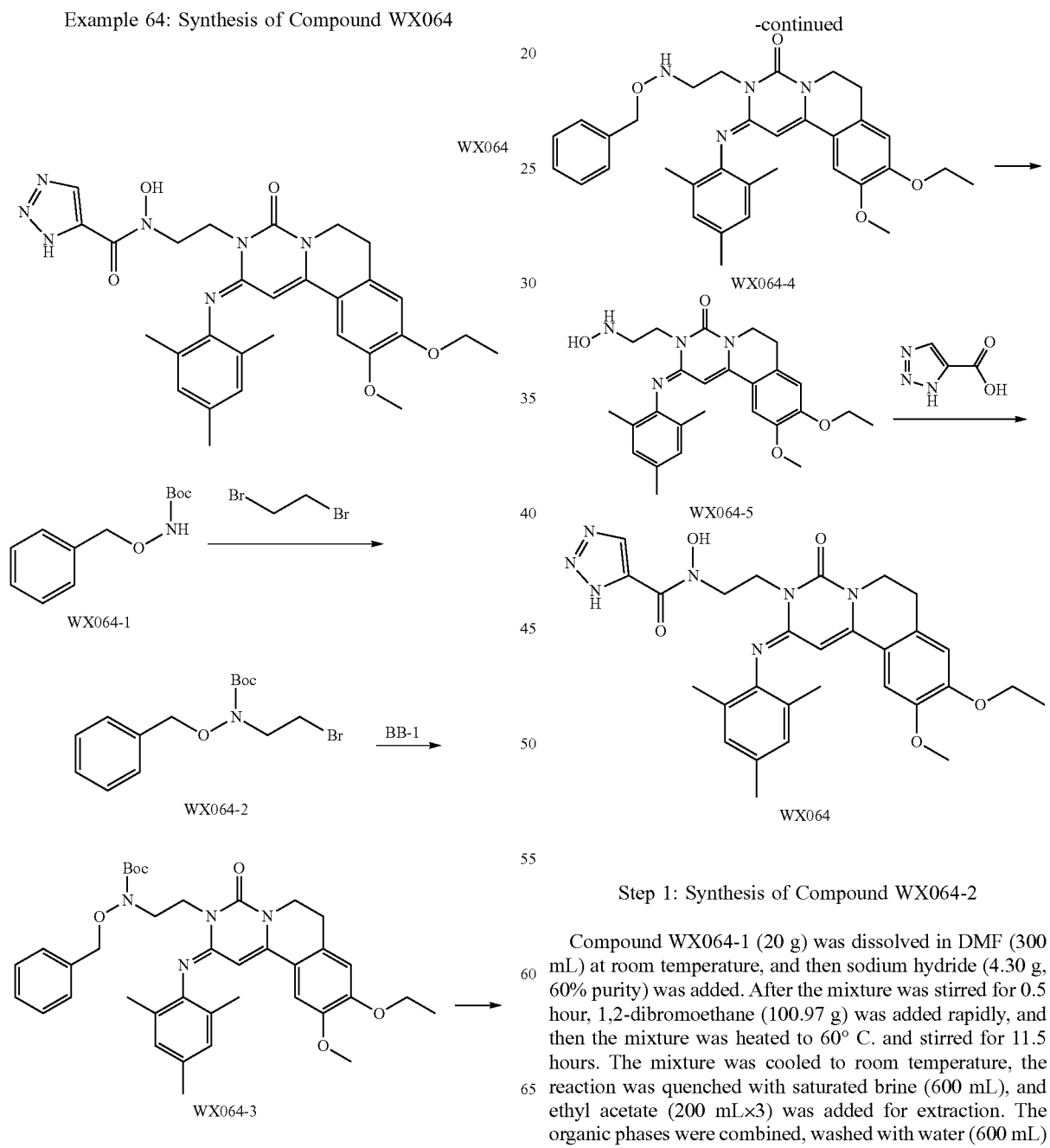

Step 1: Synthesis of Compound WX064-2

Compound WX064-1 (20 g) was dissolved in DMF (300 mL) at room temperature, and then sodium hydride (4.30 g, 60% purity) was added. After the mixture was stirred for 0.5 hour, 1,2-dibromoethane (100.97 g) was added rapidly, and then the mixture was heated to 60° C. and stirred for 11.5 hours. The mixture was cooled to room temperature, the reaction was quenched with saturated brine (600 mL), and ethyl acetate (200 mL×3) was added for extraction. The organic phases were combined, washed with water (600 mL)

and saturated saline (600 mL) successively, dried over anhydrous sodium sulfate, filtered, and concentrated under reduced pressure. The resulting residue was purified by flash silica gel column chromatography (eluent: petroleum ether/ethyl acetate=20/1-50/1) to give compound WX064-2.

MS-ESI m/z: 231.8[M−100+2+H]$^+$.

Step 2: Synthesis of Compound WX064-3

Compound WX064-2 (3.66 g) and compound BB-1 (1.5 g) were dissolved in DMF (20 mL) under nitrogen atmosphere, and then anhydrous potassium phosphate (4.71 g) and sodium iodide (3.33 g) were added. The reaction was then heated to 100° C. and stirred for 48 hours. Then the mixture was cooled to room temperature, the reaction was quenched with saturated brine (100 mL), and ethyl acetate (40 mL×3) was then added for extraction. The organic phases were combined, washed with water (200 mL×2), dried over anhydrous sodium sulfate, filtered, and concentrated under reduced pressure. The resulting residue was stirred in ethyl acetate (25 mL) for 5 minutes, the insolubles were removed by filtration, and the filtrate was concentrated and purified by prep-TLC (eluent: dichloromethane/methanol=10/1) to give compound WX064-3.

MS-ESI m/z: 655.6[M+H]$^+$.

Step 3: Synthesis of Compound WX064-4

Compound WX064-3 (700 mg) was dissolved in hydrogen chloride-ethyl acetate solution (4M, 7.67 mL) at room temperature, and the mixture was stirred at 40° C. for 3 hours. The reaction was quenched with saturated sodium bicarbonate solution (50 mL) and the reaction solution was extracted with dichloromethane (10 mL×4). The organic phases were combined, washed with saturated brine (40 mL), dried over anhydrous sodium sulfate, filtered and concentrated under reduced pressure to give compound WX064-4, which was used directly in next step.

MS-ESI m/z: 555.1[M+H]$^+$.

Step 4: Synthesis of Compound WX064-5

Compound WX064-4 (410 mg) was dissolved in methanol (10 mL) under nitrogen atmosphere, and then wet palladium on carbon (200 mg, 10% purity) was added. The mixture was then stirred under hydrogen balloon (15 psi) atmosphere at room temperature for 8 hours. The reaction solution was filtered (diatomite assisted filtration) to remove the catalyst, and the filtrate was concentrated under reduced pressure to give a crude product. The crude product was stirred in a mixed solvent of petroleum ether (15 mL) and ethyl acetate (0.5 mL) for 30 minutes and the mixture was filtered to give compound WX064-5.

MS-ESI m/z: 465.3[M+H]$^+$.

Step 5: Synthesis of Compound WX064

Compound WX064-5 (100 mg), 1,2,3-triazole-5-carboxylic acid (48.68 mg) and triethylamine (65.35 mg) were dissolved in dichloromethane (2 mL) at room temperature, and then T$_3$P (273.97 mg) was added. The mixture was heated to 40° C. and stirred for 6 hours. The reaction solution was diluted with dichloromethane (13 mL), washed with water (20 mL×3), dried over anhydrous sodium sulfate, filtered and concentrated under reduced pressure, and the resulting residue was purified by HPLC to give compound WX064.

$^1$H NMR (400 MHz, CDCl$_3$) δ=8.25 (s, 1H), 7.00 (s, 2H), 6.71 (s, 1H), 6.67 (s, 1H), 5.46 (s, 1H), 4.24 (t, J=5.6 Hz, 2H), 4.14 (q, J=6.8 Hz, 2H), 4.04-3.97 (m, 2H), 3.80 (br s, 2H), 3.74 (s, 3H), 2.94 (t, J=6.0 Hz, 2H), 2.34 (s, 3H), 2.17 (br s, 6H), 1.49 (t, J=6.8 Hz, 3H). MS-ESI m/z: 560.3[M+H]$^+$.

WX065

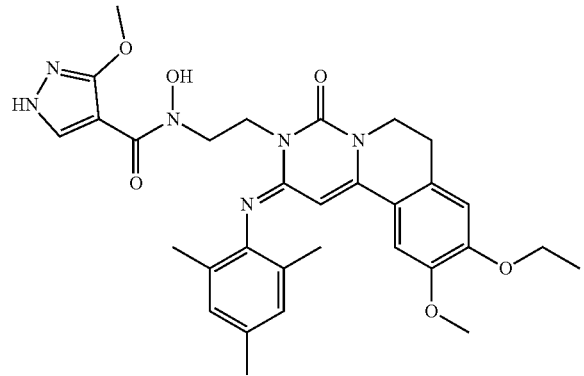

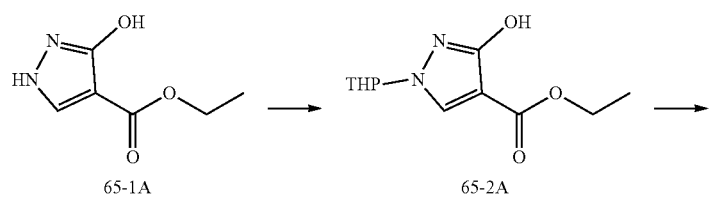

65-1A      65-2A

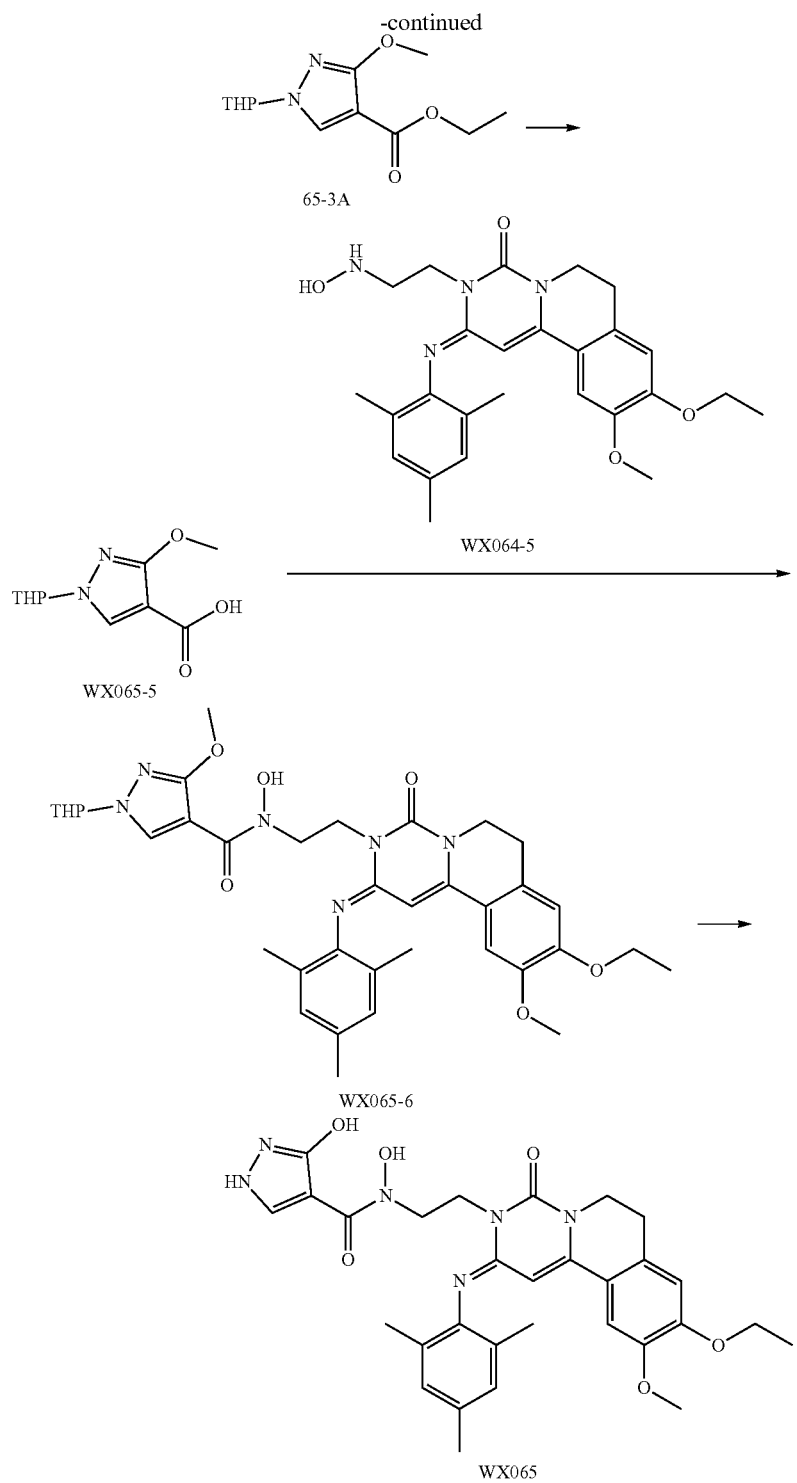

Example 65: Synthesis of Compound WX065

Step 1: Synthesis of Compound WX065-5

To a solution of compound 65-1A (2.00 g) and p-toluenesulfonic acid (1.10 g) in tetrahydrofuran (50 mL) was added dropwise DHP (2.15 g) at room temperature, and then the mixture was stirred at 20° C. for 12 hours. The reaction mixture was concentrated under reduced pressure, and the concentrate was dissolved in ethyl acetate (100 mL), washed once with saturated sodium bicarbonate (80 mL) and saturated brine (80 mL) successively, dried over anhydrous sodium sulfate, filtered, and concentrated under reduced pressure to give compound 65-2A. MS-ESI m/z: 241.2[M+H]⁺.

To a mixture of compound 65-2A (0.80 g) and potassium carbonate (2.30 g) in DMF (10 mL) was added dropwise methyl iodide (0.95 g) at 0° C., and then the resulting mixture was stirred at 25° C. for 12 hours. The reaction solution was poured into water (20 mL) and extracted with ethyl acetate (10 mL×2). The organic phases were combined, washed with saturated brine (20 mL), dried over anhydrous sodium sulfate, filtered, and then concentrated under reduced pressure to give compound 65-3A. MS-ESI m/z: 255.2[M+H]$^+$.

To a solution of compound 65-3A (0.80 g) in tetrahydrofuran (4 mL) was added dropwise a solution of sodium hydroxide (0.38 g) in water (8 mL) at 0° C., and then the mixture was stirred at 25° C. for 12 hours. The reaction solution was adjusted to pH=4 with 2 mol/L hydrochloric acid under an ice bath, and then extracted with ethyl acetate (20 mL×2). The organic phases were combined, washed with saturated brine (20 mL), dried over anhydrous sodium sulfate, filtered, and then concentrated under reduced pressure to give compound WX065-5.

MS-ESI m/z: 227.0[M+H]$^+$.

Step 2: Synthesis of Compound WX065-6

Compound WX064-5 (60.0 mg), WX065-5 (58.44 mg) and triethylamine (65.35 mg) were dissolved in DMF (1 mL) at room temperature, and then PyBOP (201.64 mg) was added. The mixture was then stirred at 20° C. for 12 hours. The mixture was purified by HPLC to give compound WX065-6. MS-ESI m/z: 673.4[M+H]$^+$.

Step 5: Synthesis of Compound WX065

Compound WX065-6 (40 mg) was dissolved in hydrogen chloride-ethyl acetate solution (4M, 1 mL), and the mixture was stirred at 20° C. for 1 hour. The reaction solution was concentrated under reduced pressure, and the concentrate was purified by HPLC to give compound WX065.

$^1$H NMR (400 MHz, CD$_3$OD) δ=7.95 (s, 1H), 7.12 (s, 2H), 6.98 (s, 1H), 6.80 (s, 1H), 5.68 (s, 1H), 4.69-4.66 (m, 2H), 4.45 (br s, 2H), 4.21 (t, J=6.4 Hz, 2H), 4.16 (q, J=7.2 Hz, 2H), 3.99 (br s, 3H), 3.70 (s, 3H), 3.07 (t, J=6.4 Hz, 2H), 2.36 (s, 3H), 2.24 (s, 6H), 1.43 (t, J=7.2 Hz, 3H). MS-ESI m/z: 589.1[M+H]$^+$.

Examples in the following table were synthesized with reference to the synthesis method of Example 65.

| Example | Fragment 1 | Fragment 2 | Structure of compound | Compound number |
|---|---|---|---|---|
| 66 | (structure) | WX065-4 | (structure) | WX066 |
| 67 | (structure) | WX065-4 | (structure) | WX067 |
| 68 | (structure) | WX065-4 | (structure) | WX068 |

NMR and MS Data of the Examples

| Example | Compound | ¹H-NMR | MS m/z [M + H]⁺ |
|---|---|---|---|
| 11 | WX004 | ¹H NMR (400 MHz, DMSO-d6)δ = 8.39 (br s, 1H), 7.08 (br s, 2H), 7.02 (s, 1H), 6.70 (s, 1H), 5.26 (s, 1H), 4.57 (br s, 2H), 4.09 (q, J = 6.8 Hz, 2H), 3.85 (br s, 2H), 3.69 (s, 3H), 3.52 (br s, 2H), 2.78 (br s, 2H), 2.29 (s, 3H), 2.23 (br s, 6H), 2.15 (br s, 2H), 1.41 (t, J = 6.8 Hz, 3H). | 530.0 |
| 13 | WX006 | ¹H NMR (400 MHz, CDCl₃)δ = 6.81 (s, 2H), 6.63 (s, 1H), 6.59 (s, 1H), 5.42 (s, 1H), 5.13 (br s, 1H), 4.40-4.29 (m, 2H), 4.05 (q, J = 7.2 Hz, 2H), 3.99-3.85 (m, 2H), 3.68 (s, 3H), 3.61-3.45 (m, 2H), 2.84-2.82 (m, 2H), 2.20 (s, 3H), 2.15 (s, 3H), 2.00 (s, 6H), 1.41 (t, J = 7.2 Hz, 3H). | 530.1 |
| 14 | WX007 | ¹H NMR (400 MHz, CD₃OD)δ = 7.91 (d, J = 2.0 Hz, 1H), 7.18 (s, 2H), 7.00 (s, 1H), 6.81 (s, 1H), 6.04 (d, J = 2.0 Hz, 1H), 5.69 (s, 1H), 4.59 (t, J = 6.4 Hz, 2H), 4.26-4.11 (m, 4H), 3.78 (t, J = 6.0 Hz, 2H), 3.71 (s, 3H), 3.08 (t, J = 6.4 Hz, 2H), 2.40 (s, 3H), 2.30 (s, 6H), 1.45 (t, J = 6.8 Hz, 3H). | 515.1 |
| 15 | WX008 | ¹H NMR (400 MHz, CD₃OD)δ = 8.05 (s, 2H), 7.17 (s, 2H), 7.00 (s, 1H), 6.83 (s, 1H), 5.71 (s, 1H), 4.80 (br s, 2H), 4.25 (br s, 2H), 4.18 (q, J = 6.8 Hz, 2H), 3.82 (br s, 2H), 3.72 (s, 3H), 3.11 (br s, 2H), 2.39 (s, 3H), 2.32 (s, 6H), 1.45 (t, J = 6.8 Hz, 1H). | 515.1 |
| 16 | WX009 | ¹H NMR (400 MHz, CD₃OD)δ = 7.60 (s, 1H), 7.17 (s, 2H), 7.00 (s, 1H), 6.81 (s, 1H), 5.68 (s, 1H), 4.59 (t, J = 6.0 Hz, 2H), 4.21-4.17 (m, 4H), 3.78 (t, J = 6.0 Hz, 2H), 3.71 (s, 3H), 3.08 (t, J = 6.40 Hz, 2H), 2.40 (s, 3H), 2.29 (s, 6H), 1.45 (t, J = 6.8 Hz, 3H). | 516.1 |
| 19 | WX016 | ¹H NMR (400 MHz, CD₃OD)δ = 8.29 (s, 1H), 7.16 (s, 2H), 6.98 (s, 1H), 6.82 (s, 1 H), 5.69 (s, 1H), 4.58 (t, J = 6.4 Hz, 2H), 4.19-4.13 (m, 4H), 3.92 (t, J = 6.0 Hz, 2H), 3.72 (s, 3H), 3.03 (t, J = 6.0 Hz, 2H), 2.40 (s, 3H), 2.28 (s, 6H), 1.45 (t, J = 6.8 Hz, 3H). | 544.1 |
| 20 | WX017 | ¹H NMR (400 MHz, CD₃OD)δ = 7.67 (br s, 2H), 7.18 (s, 2H), 6.99 (s, 1H), 6.82 (s, 1H), 5.70 (s, 1H), 4.65 (t, J = 5.6 Hz, 2H), 4.18-4.11 (m, 4H), 3.99 (t, J = 5.6 Hz, 2H), 3.72 (s, 3H), 3.06 (t, J = 6.0 Hz, 2H), 2.40 (s, 3H), 2.31 (s, 6H), 1.45 (t, J = 6.8 Hz, 3H). | 543.2 |
| 21 | WX018 | ¹H NMR (400 MHz, CD₃OD)δ = 7.71 (d. J = 2.0 Hz, 1H), 7.16 (s, 2H), 6.99 (s, 1H), 6.83 (s, 1H), 6.76 (d. J = 2.0 Hz, 1H), 5.70 (s, 1H), 4.55 (t. J = 6.4 Hz, 2H), 4.20-4.13 (m, 4H), 3.90 (t. J = 6.0 Hz, 2H), 3.72 (s, 3H), 3.03 (t. J = 6.4 Hz, 2H), 2.40 (s, 3H), 2.28 (s, 6H), 1.45 (t, J = 6.8 Hz, 3H). | 543.2 |
| 22 | WX019 | ¹H NMR (400 MHz, CD₃OD)δ = 8.11 (s, 1H), 7.39 (s, 1H), 7.17 (s, 2H), 6.99 (s, 1H), 6.82 (s, 1H), 5.69 (s, 1H), 4.58 (t. J = 6.4 Hz, 2H), 4.20-4.11 (m, 4H), 3.91 (t. J = 6.0 Hz, 2H), 3.72 (s, 3H), 3.04 (t. J = 6.4 Hz, 2H), 2.40 (s, 3H), 2.28 (s, 6H), 1.45 (t, J = 6.8 Hz, 3H). | 544.0 |
| 23 | WX020 | ¹H NMR (400 MHz, CD₃OD)δ = 9.47 (s, 1H), 7.18 (s, 2H), 6.99 (s, 1H), 6.83 (s, 1H), 5.70 (s, 1H), 4.62 (t. J = 6.0 Hz, 2H), 4.20-4.13 (m, 4H), 3.96 (t. J = 6.0 Hz, 2H), 3.72 (s, 3H), 3.04 (t. J = 6.4 Hz, 2H), 2.40 (s, 3H), 2.31 (s, 6H), 1.45 (t, J = 6.8 Hz, 3H). | 545.0 |
| 24 | WX021 | ¹H NMR (400 MHz, DMSO-d6)δ = 8.03 (t, J = 5.6 Hz, 1H),7.68 (s, 1H), 7.57 (s, 1H), 6.94 (s, 1H), 6.84 (s, 2H), 6.66 (s, 1H), 5.32 (s, 1H), 4.36 (t. J = 6.0 Hz, 2H), 4.06 (q, J = 6.8 Hz, 2H), 3.89 (t. J = 6.0 Hz, 2H), 3.68-3.58 (m, 5H), 2.87 (t. J = 5.6 Hz, 2H), 2.22 (s, 3H), 1.95 (s, 6H), 1.33 (t, J = 6.8 Hz, 3H). | 543.1 |
| 25 | WX022 | ¹H NMR (400 MHz, DMSO-d6)δ = 8.79 (br s, 1H), 6.96 (s, 1H), 6.88 (s, 2H), 6.68 (s, 1H), 5.36 (s, 1H), 4.40 (t, J = 6.0 Hz, 2H), 4.07 (q, J = 6.8 Hz, 2H), 3.89 (t, J = 6.0 Hz, 2H), 3.72-3.62 (m, 2H), 3.63 (s, 3H), 2.87 (t, J = 6.4 Hz, 2H), 2.23 (s, 3H), 1.96 (s, 6H), 1.34 (t, J = 6.8 Hz, 3H). | 545.4 |
| 26 | WX023 | ¹H NMR (400 MHz, CD₃OD)δ = 9.06 (s, 1H), 7.16 (s, 2H), 6.97 (s, 1H), 6.81 (s, 1H), 5.69 (s, 1H), 4.59 (t, J = 6.0 Hz, 2H), 4.19-4.09 (m, 4H), 3.93 (t, J = 6.4 Hz, 2H), 3.70 (s, 3H), 3.01 (t, J = 6.4 Hz, 2H), 2.38 (s, 3H), 2.27 (s, 6H), 1.43 (t, J = 6.8 Hz, 3H). | 561.2 |
| 27 | WX024 | ¹H NMR (400 MHz, CD₃OD)δ = 6.89 (s, 2H), 6.85 (s, 1H), 6.75 (s, 1H), 5.49 (s, 1H), 4.50 (t, J = 6.0 Hz, 2H), 4.09 (q, J = 6.8 Hz, 2H), 3.98 (t, J = 6.0 Hz, 2H), 3.84 (t, J = 6.0 Hz, 2H), 3.70 (s, 3H), 2.90 (t, J = 6.4 Hz, 2H), 2.48 (s, 3H), 2.27 (s, 3H), 2.01 (s, 6H), 1.41 (t, J = 6.8 Hz, 3H). | 558.3 |
| 28 | WX025 | ¹H NMR (400 MHz, CDCl₃)δ = 6.90 (br s, 2H), 6.72 (s, 1H), 6.66 (s, 1H), 5.48 (s, 1H), 5.21 (br s, 2H), 4.58 (br s, 2H), 4.16-4.06 (m, 4H), 3.87 (br s, 2H), 3.76 (s, 3H), 2.89 (br s, 2H), 2.30 (s, 3H), 2.04 (s, 6H), 1.48 (br t, J = 6.8 Hz, 3H). | 559.2 |

| Example | Compound | ¹H-NMR | MS m/z [M + H]⁺ |
|---|---|---|---|
| 29 | WX026 | ¹H NMR (400 MHz, CDCl₃)δ = 8.17 (br s, 1H), 6.94 (s, 2H), 6.72 (s, 1H), 6.59 (s, 1H), 5.51 (s, 1H), 4.72 (br s, 2H), 4.24-4.12 (m, 4H), 4.05-3.98 (m, 2H), 3.97 (s, 3H), 3.71 (s, 3H), 2.99 (br s, 2H), 2.30 (s, 3H), 2.08 (s, 6H), 1.49 (t, J = 6.8 Hz, 3H). | 574.0 |
| 30 | WX027 | ¹H NMR (400 MHz, CD₃OD)δ 7.15 (s, 2H), 6.97 (s, 1H), 6.81 (s, 1H), 5.68 (s, 1H), 4.56 (t, J = 6.0 Hz, 2H), 4.20-4.08 (m, 4H), 3.88 (t, J = 6.0 Hz, 2H), 3.70 (s, 3H), 3.02 (t, J = 6.4 Hz, 2H), 2.38 (s, 3H), 2.27 (s, 6H), 1.43 (t, J = 6.8 Hz, 3H). | 562.2 |
| 31 | WX028 | ¹H NMR (400 MHz, CD₃OD)δ = 7.17 (s, 2H), 6.99 (s, 1H), 6.83 (s, 1H), 5.70 (s, 1H), 4.57 (t, J = 6.0 Hz, 2H), 4.21-4.13 (m, 4H), 3.90 (t, J = 5.6 Hz, 2H), 3.72 (s, 3H), 3.05 (t, J = 6.4 Hz, 2H), 2.40 (s, 3 H), 2.28 (s, 6 H), 1.45 (t, J = 6.8 Hz, 3H). | 578.1 |
| 32 | WX029 | ¹H NMR (400 MHz, CD₃OD)δ = 7.02 (s, 2H), 6.92 (s, 1H), 6.76 (s, 1H), 5.57 (s, 1H), 4.51 (t, J = 6.0 Hz, 2H), 4.17-4.05 (m, 4H), 3.88 (t, J = 6.0 Hz, 2H), 3.68 (s, 3H), 2.97 (br s, 2H), 2.32 (s, 3H), 2.09 (s, 6H), 1.42 (t, J = 6.8 Hz, 3H). | 612.3 |
| 33 | WX030 | ¹H NMR (400 MHz, CD₃OD)δ = 7.15 (s, 2H), 6.97 (s, 1H), 6.80 (s, 1H), 5.68 (s, 1H), 4.68-4.51 (m, 2H), 4.15 (q, J = 6.8 Hz, 2H), 4.10 (t, J = 6.0 Hz, 2H), 4.02-3.92 (m, 2H), 3.70 (s, 3H), 3.00 (t, J = 6.0 Hz, 2H), 2.38 (s, 3H), 2.26 (s, 6H), 1.43 (t, J = 6.8 Hz, 3H). | 586.9 |
| 34 | WX031 | ¹H NMR (400 MHz, CD₃OD)δ = 7.16 (s, 2H), 6.97 (s, 1H), 6.82 (s, 1H), 5.70 (s, 1H), 4.60 (t, J = 6.0 Hz, 2H), 4.20-4.10 (m, 4H), 3.97 (t, J = 6.0 Hz, 2H), 3.94 (s, 3H), 3.70 (s, 3H), 3.02 (t, J = 6.4 Hz, 2H), 2.38 (s, 3H), 2.28 (s, 6H), 1.43 (t, J = 6.8 Hz, 3H). | 602.1 |
| 35 | WX032 | ¹H NMR (400 MHz, CD₃OD)δ = 7.15 (s, 2H), 6.96 (s, 1H), 6.81 (s, 1H), 5.69 (s, 1H), 4.57 (t, J = 6.0 Hz, 2H), 4.23-4.06 (m, 4H), 3.90 (t, J = 6.0 Hz, 2H), 3.70 (s, 3H), 3.03 (t, J = 6.4 Hz, 2H), 2.38 (s, 3H), 2.27 (s, 6H), 1.43 (t, J = 6.8 Hz, 3H). | 569.3 |
| 36 | WX033 | ¹H NMR (400 MHz, CD₃OD)δ = 7.16 (s, 2H), 6.98 (s, 1H), 6.82 (s, 1H), 5.69 (s, 1H), 4.55 (t, J = 6.0 Hz, 2H), 4.21-4.13 (m, 4H), 3.92 (t, J = 6.0 Hz, 2H), 3.71 (s, 3H), 3.04 (t, J = 6.4 Hz, 2H), 2.39 (s, 3H), 2.27 (s, 6H), 1.45 (t, J = 6.8 Hz, 3H). | 560.2 |
| 37 | WX034 | ¹H NMR (400 MHz, CDCl₃)δ = 7.79 (s, 1H), 6.86 (s, 2H), 6.68 (s, 1H), 6.65 (s, 1H), 5.46 (s, 1H), 4.61 (br s, 2H), 4.13 (q, J = 6.8 Hz, 2H), 4.06 (br s, 2H), 3.88 (br s, 2H), 3.73 (s, 3H), 2.89 (br s, 2H), 2.27 (s, 3H), 2.01 (s, 6H), 1.49 (t, J = 6.8 Hz, 3H). | 560.3 |
| 38 | WX035 | ¹H NMR (400 MHz, CD₃OD)δ = 8.40 (s, 1H), 7.15 (s, 2H), 6.98 (s, 1H), 6.80 (s, 1H), 5.66 (s, 1H), 4.56 (t, J = 6.0 Hz, 2H), 4.23-4.10 (m, 4H), 3.96 (t, J = 6.0 Hz, 2H), 3.70 (s, 3H), 3.04 (t, J = 6.4 Hz, 2H), 2.38 (s, 3H), 2.25 (s, 6H), 1.44 (t, J = 6.8 Hz, 3H). | 560.1 |
| 39 | WX036 | ¹H NMR (400 MHz, CD₃OD)δ = 6.94 (s, 2H), 6.87 (s, 1H), 6.77 (s, 1H), 5.52 (s, 1H), 4.48 (t, J = 6.0 Hz, 2H), 4.15 (s, 3H), 4.12-4.08 (m, 2H), 4.01 (t, J = 6.0 Hz, 2H), 3.87 (t, J = 6.0 Hz, 2H), 3.69 (s, 3H), 2.94 (t, J = 6.0 Hz, 2H), 2.29 (s, 3H), 2.06 (s, 6H), 1.41 (t, J = 6.8 Hz, 3H). | 574.1 |
| 40 | WX037 | ¹H NMR (400 MHz, CD₃OD)δ = 7.53 (br s, 1H), 7.14 (s, 2H), 6.97 (s, 1H), 6.80 (s, 1H), 5.67 (s, 1H), 4.54 (t, J = 6.0 Hz, 2H), 4.18-4.12 (m, 4H), 3.94-3.89 (m, 5H), 3.69 (s, 3H), 3.02 (t, J = 6.4 Hz, 2H), 2.37 (s, 3H), 2.25 (s, 6H), 1.43 (t, J = 6.8 Hz, 3H). | 573.3 |
| 41 | WX038 | ¹H NMR (400 MHz, CD₃OD)δ = 7.22 (s, 1H), 7.14 (s, 2H), 6.97 (s, 1H), 6.80 (s, 1H), 5.68 (s, 1H), 4.53 (t, J = 6.4 Hz, 2H), 4.16-4.14 (m, 4H), 3.90 (t, J = 6.4 Hz, 2H), 3.70 (s, 3H), 3.02 (t, J = 6.4 Hz, 2H), 2.37 (s, 3H), 2.26 (s, 6H), 1.43 (t, J = 6.8 Hz, 3H). | 559.2 |
| 42 | WX039 | ¹H NMR (400 MHz, CD₃OD)δ = 7.88 (s, 1H), 7.15 (s, 2H), 6.97 (s, 1H), 6.80 (s, 1H), 5.67 (s, 1H), 4.50 (t, J = 6.4 Hz, 2H), 4.19-4.12 (m, 4H), 3.85 (t, J = 6.4 Hz, 2H), 3.70 (s, 3H), 3.02 (t, J = 6.4 Hz, 2H), 2.38 (s, 3H), 2.27 (s, 6H), 1.43 (t, J = 6.8 Hz, 3H). | 559.3 |
| 43 | WX040 | ¹H NMR (400 MHz, CD₃OD)δ = 8.34 (s, 1H), 6.90 (s, 2H), 6.84 (s, 1H), 6.75 (s, 1H), 5.49 (s, 1H), 4.50 (t, J = 6.0 Hz, 2H), 4.09 (q, J = 6.8 Hz, 2H), 3.97 (t, J = 6.0 Hz, 2H), 3.89 (t, J = 6.0 Hz, 2H), 3.68 (s, 3H), 2.90 (t, J = 6.4 Hz, 2H), 2.27 (s, 3H), 2.04 (s, 6H), 1.41 (t, J = 6.8 Hz, 3H). | 560.1 |
| 44 | WX041 | ¹H NMR (400 MHz, CD₃OD)δ = 7.86 (s, 1H), 6.91 (s, 2H), 6.84 (s, 1H), 6.75 (s, 1H), 5.49 (s, 1H), 4.47 (t, J = 5.6 Hz, 2H), 4.09 (q, J = 6.8 Hz, 2H), 3.99 (t, J = 6.0 Hz, 2H), 3.84-3.78 (m, 5H), 3.68 (s, 3H), 2.90 (t, J = 6.0 Hz, 2H), 2.27 (s, 3H), 2.02 (s, 6H), 1.40 (t, J = 6.8 Hz, 3H). | 573.3 |

| Example | Compound | ¹H-NMR | MS m/z [M + H]⁺ |
|---|---|---|---|
| 45 | WX042 | ¹H NMR (400 MHz, DMSO-d6)δ = 8.00 (br s, 1H), 7.12 (s, 2H), 7.07 (s, 1H), 6.76 (s, 1H), 5.56 (s, 1H), 4.35 (br s, 2H), 4.17-4.06 (m, 4H), 3.68 (m, 2H), 3.64 (s, 3H), 2.97 (br s, 2H), 2.32 (s, 3H), 2.19 (s, 6H), 1.35 (t, J = 6.8 Hz, 3H). | 559.2 |
| 46 | WX043 | ¹H NMR (400 MHz, CD₃OD)δ = 6.99 (s, 1H), 6.90 (br s, 2H), 6.84 (s, 1H), 6.74 (s, 1H), 5.48 (s, 1H), 4.44 (br s, 2H), 4.08 (br d, J = 6.8 Hz, 2H), 3.97 (br s, 2H), 3.77 (br s, 2H), 3.68 (s, 3H), 2.89 (br s, 2H), 2.27 (s, 3H), 2.04 (s, 6H), 1.40 (t, J = 6.8 Hz, 3H). | 559.1 |
| 47 | WX044 | ¹H NMR (400 MHz, CDCl₃)δ = 8.29 (br s, 1H), 6.88 (br s, 2H), 6.72 (s, 1H), 6.67 (s, 1H), 6.46 (s, 1H), 5.50 (s, 1H), 4.60 (t, J = 5.6 Hz, 2H), 4.12 (q, J = 6.8 Hz, 2H), 4.06 (t, J = 6.0 Hz, 2H), 3.87 (t, J = 5.6 Hz, 2H), 3.76 (s, 3H), 2.90 (t, J = 6.0 Hz, 2H), 2.28 (s, 3H), 2.04 (s, 6H), 1.49 (t, J = 6.8 Hz, 3H). | 560.0 |
| 48 | WX045 | ¹H NMR (400 MHz, CD₃OD)δ 7.15 (s, 2H), 6.98 (s, 1H), 6.80 (s, 1H), 5.67 (s, 1H), 4.53 (t, J = 6.0 Hz, 2H), 4.25-4.07 (m, 4H), 3.85 (t, J = 6.0 Hz, 2H), 3.70 (s, 3H), 3.03 (t, J = 6.4 Hz, 2H), 2.37 (s, 3H), 2.27 (s, 6H), 1.43 (t, J = 6.8 Hz, 3H). | 560.0 |
| 49 | WX046 | ¹H NMR (400 MHz, CD₃OD)δ = 7.15 (br s, 2H), 6.97 (s, 1H), 6.79 (s, 1H), 5.67 (s, 1H), 4.56 (t, J = 6.0 Hz, 2H), 4.21-4.08 (m, 4H), 3.90 (t, J = 6.0 Hz, 2H), 3.69 (s, 3H), 3.01 (t, J = 6.4 Hz, 2H), 2.37 (s, 3H), 2.24 (s, 6H), 1.43 (t, J = 6.8 Hz, 3H). | 576.2 |
| 50 | WX047 | ¹H NMR (400 MHz, CD₃OD)δ = 8.52 (br s, 1H), 7.12 (br s, 2H), 6.95 (s, 1H), 6.80 (s, 1H), 5.41 (s, 1H), 4.80 (br s, 2H), 4.61 (br s, 2H), 4.14 (q, J = 6.8 Hz, 2H), 4.06-3.88 (m, 2H), 3.76 (s, 3H), 2.73 (t, J = 6.8 Hz, 2H), 2.36 (s, 3H), 2.30 (br s, 6H), 2.05 (br s, 2H), 1.43 (t, J = 6.8 Hz, 3H). | 558.0 |
| 51 | WX048 | ¹H NMR (400 MHz, CD₃OD)δ = 8.35 (br s, 1H), 7.13 (br s, 2H), 6.95 (s, 1H), 6.80 (s, 1H), 5.42 (s, 1H), 4.80 (br s, 2H), 4.59 (br s, 2H), 4.14 (q, J = 6.8 Hz, 2H), 4.05-3.84 (m, 2H), 3.77 (s, 3H), 2.71 (br s, 2H), 2.37 (s, 3H), 2.30 (br s, 6H), 2.10-1.95 (m, 2H), 1.43 (t, J = 6.8 Hz, 3H). | 558.4 |
| 52 | WX049 | ¹H NMR (400 MHz, CD₃OD)δ = 7.70 (br s, 1H), 7.63 (br s, 1H), 6.86 (br s, 2H), 6.83 (s, 1H), 6.71 (s, 1H), 5.12 (s, 1H), 4.80 (br s, 2H), 4.52 (t, J = 5.6 Hz, 2H), 4.09 (q, J = 6.8 Hz, 2H), 4.02-3.81 (m, 2H), 3.74 (s, 3H), 2.68-2.60 (m, 2H), 2.25 (s, 3H), 2.05 (br s, 8H), 1.41 (t, J = 6.8 Hz, 3H). | 557.3 |
| 53 | WX050 | ¹H NMR (400 MHz, CD₃OD)δ = 7.74 (br s, 1H), 7.13 (br s, 2H), 6.95 (s, 1H), 6.81-6.77 (m, 2H), 5.41 (s, 1H), 4.90-4.80 (m, 2H), 4.70-4.50 (m, 2H), 4.14 (q, J = 6.8 Hz, 2H), 4.02-3.85 (m, 2H), 3.76 (s, 3H), 2.72-2.66 (m, 2H), 2.36 (s, 3H), 2.30 (br s, 6H), 2.07-1.90 (m, 2H), 1.43 (t, J = 6.8 Hz, 3H). | 557.3 |
| 54 | WX051 | ¹H NMR (400 MHz, CD₃OD)δ = 7.09 (br s, 2H), 6.92 (s, 1H), 6.75 (s, 1H), 5.39 (s, 1H), 4.80 (br s, 2H), 4.61 (br s, 2H), 4.11 (q, J = 6.8 Hz, 2H), 3.94 (br s, 2H), 3.73 (s, 3H), 2.68 (t, J = 6.4 Hz, 2H), 2.33 (s, 3H), 2.26 (br s, 6H), 2.07-1.90 (m, 2 H), 1.40 (t, J = 6.8 Hz, 3H). | 559.3 |
| 55 | WX052 | ¹H NMR (400 MHz, CD₃OD)δ = 7.69 (br s, 1H), 7.08 (br s, 2H), 6.75 (br s, 2H), 6.64 (s, 1H), 5.23 (s, 1H), 4.44 (t, J = 5.6 Hz, 2H), 4.26 (t, J = 5.6 Hz, 2H), 4.11-4.07 (m, 4H), 3.74-3.70 (m, 5H), 2.34 (s, 3H), 2.20 (br s, 6H), 1.42 (t, J = 6.8 Hz, 3H). | 559.3 |
| 56 | WX053 | ¹H NMR (400 MHz, CD₃OD)δ = 8.18 (br s, 1H), 7.06 (s, 2H), 6.73 (s, 1H), 6.62 (s, 1H), 5.21 (s, 1H), 4.42 (t, J = 6.0 Hz, 2H), 4.24 (t, J = 5.2 Hz, 2H), 4.10-4.05 (m, 4H), 3.75-3.70 (m, 5H), 2.32 (s, 3H), 2.18 (s, 6H), 1.40 (t, J = 6.8 Hz, 3H). | 560.3 |
| 58 | WX055 | ¹H NMR (400 MHz, DMSO-d6)δ = 8.34 (br s, 1H), 7.85 (br s, 1H), 6.94 (s, 1H), 6.85 (s, 2H), 6.67 (s, 1H), 5.33 (s, 1H), 4.41 (br s, 2H), 4.06 (q, J = 7.2 Hz, 2H), 3.91 (br s, 2H), 3.62 (s, 3H), 2.89 (br s, 2H), 2.82 (t, J = 8.0 Hz, 2H), 2.22 (s, 3H), 1.96 (br s, 6H), 1.33 (t, J = 7.2 Hz, 3H). | 544.3 |
| 59 | WX056 | ¹H NMR (400 MHz, CDCl₃)δ = 7.29 (s, 1H), 6.96 (s, 1H), 6.89 (s, 2H), 6.73 (s, 1H), 6.67 (s, 1H), 5.51 (s, 1H), 4.62 (t, J = 6.4 Hz, 2H), 4.20-4.06 (m, 4H), 3.77 (s, 3H), 3.07 (t, J = 6.4 Hz, 2H), 2.91 (t, J = 6.4 Hz, 2H), 2.30 (s, 3H), 2.06 (s, 6H), 1.49 (t, J = 6.8 Hz, 3H). | 544.3 |
| 60 | WX057 | ¹H NMR (400 MHz, DMSO-d6)δ = 12.52 (br s, 1H), 10.01 (s, 1H), 7.82 (br s, 1H), 7.46 (br s, 1H), 6.94 (s, 1H), 6.86 (s, 2H), 6.67 (s, 1H), 5.33 (s, 1H), 4.40 (t, J = 8.0 Hz, 2H), 4.04 (q, J = 7.2 Hz, 2H), 3.92 (t, J = 6.4 Hz, 2H), 3.62 (s, 3H), 2.89 (t, J = 6.4 Hz, 2H), 2.73 (t, J = 8.0 Hz, 2H), 2.22 (s, 3H), 1.97 (s, 6H), 1.33 (t, J =7.2 Hz, 3H). | 543.3 |

| Example | Compound | ¹H-NMR | MS m/z [M + H]⁺ |
|---|---|---|---|
| 63 | WX060 | ¹H NMR (400 MHz, CD₃OD)δ = 8.26 (br s, 1H), 7.85 (br s, 1H), 7.14 (s, 2H), 6.97 (s, 1H), 6.78 (s, 1H), 5.66 (s, 1H), 4.47 (br s, 2H), 4.23-4.09 (m, 4H), 3.69 (s, 3H), 3.57 (br s, 2H), 3.05 (br s, 2H), 2.36 (s, 3H), 2.29 (s, 6H), 1.42 (t, J = 6.8 Hz, 3H). | 579.0 |
| 66 | WX066 | ¹H NMR (400 MHz, CD₃OD)δ = 6.98 (s, 2H), 6.90 (s, 1H), 6.77 (s, 1H), 5.57 (s, 1H), 4.62 (t, J = 4.4 Hz, 2H), 4.36 (t, J = 4.4 Hz, 2H), 4.16 (s, 3H), 4.14-4.07 (m, 4H), 3.69 (s, 3H), 2.98 (t, J = 6.0 Hz, 2H), 2.30 (s, 3H), 2.11 (s, 6H), 1.42 (t, J = 6.8 Hz, 3H). | 590.3 |
| 67 | WX067 | ¹H NMR (400 MHz, CD₃OD)δ = 7.12 (s, 2H), 6.98 (s, 1H), 6.80 (s, 1H), 5.68 (s, 1H), 4.68 (t, J = 4.4 Hz, 2H), 4.46 (t, J = 4.4 Hz, 2H), 4.22-4.16 (m, 4H), 4.01 (s, 3H), 3.70 (s, 3H), 3.07 (t, J = 6.4 Hz, 2H), 2.36 (s, 3H), 2.24 (s, 6H), 1.43 (t, J = 6.8 Hz, 3H). | 590.1 |
| 68 | WX068 | ¹H NMR (400 MHz, CD₃OD)δ = 7.17 (br s, 1H), 6.92 (s, 2H), 6.88 (s, 1H), 6.78 (s, 1H), 5.53 (s, 1H), 4.62 (br s, 2H), 4.33 (br s, 2H), 4.16-4.03 (m, 4H), 3.71 (s, 3H), 2.96 (t, J = 5.6 Hz, 2H), 2.29 (s, 3H), 2.06 (s, 6H), 1.43 (t, J = 6.8 Hz, 3H). | 575.2 |

Experimental Example 1

In Vitro Detection of the Inhibitory Activity of Compounds Against PDE 3A Enzyme Experimental objective: to determine the AMP/GMP expression based on fluorescence polarization, i.e., to trace binding of AMP/GMP to antibody so as to indicate enzyme activity.

Reagents:

Experimental buffer solution: 10 mM Tris-HCl (pH 7.5), 5 mM $MgCl_2$, 0.01% Brij 35, 1 mM Dithiothreitol (DTT), and 1% DMSO.

Enzyme: recombinant human PDE3A (Gene accession number: NM_000921; amino acid 669-end) was expressed by baculovirus in Sf9 insect cells using an N-terminal GST tag, with molecular weight being 84 kDa.

Enzyme substrate: 1 μM cAMP

Detection: Transcreener®AMP2/GMP2 antibody and AMP2/GMP2 AlexaFluor633 tracer.

Procedure:
1. The recombinant human PDE3A enzyme and enzyme substrate (1 μM cAMP) were each dissolved in newly-prepared experimental buffer solution;
2. The PDE3A enzyme buffer solution was transferred into reaction wells;
3. The compound which was dissolved in 100% DMSO was added to the reaction wells containing PDE3A enzyme buffer solution by acoustic technique (echo 550; millilambda range) and the mixture was incubated for 10 minutes at room temperature;
4. The enzyme substrate buffer solution was added to the above reaction wells to initiate reaction;
5. The resulting mixture was incubated at room temperature for 1 hour;
6. The detection mixture (Transcreener®AMP2/GMP2 antibody and AMP2/GMP2 AlexaFluor633 tracer) was added to stop the reaction, and the resulting mixture was incubated for 90 minutes while slowly mixing. The measurement range of fluorescence polarization was Ex/Em=620/688.

Data analysis: the fluorescence polarization signal was converted to nM based on AMP/GMP standard curve and the percentage enzyme activity relative to DMSO control calculated by Excel. GraphPad Prism was used for curve fitting (drawing medical icon). The experimental results are shown in Table 1.

Experimental Example 2

In Vitro Detection of the Inhibitory Activity of Compounds Against PDE 4B Enzyme Experimental objective: to determine the AMP/GMP expression based on fluorescence polarization, i.e., to trace binding of AMP/GMP to antibody so as to indicate enzyme activity.

Reagents:

Experimental buffer solution: 10 mM Tris-HCl (pH 7.5), 5 mM $MgCl_2$, 0.01% Brij 35, 1 mM DTT, and 1% DMSO.

Enzyme: recombinant human PDE4B (Gene accession number: NM_002600; amino acid 305-end) was expressed by baculovirus in Sf9 insect cells using an N-terminal GST tag, with molecular weight being 78 kDa.

Enzyme substrate: 1 μM cAMP

Detection: Transcreener®AMP2/GMP2 antibody and AMP2/GMP2 AlexaFluor633 tracer.

Procedure:
1. The recombinant human PDE4B enzyme and enzyme substrate (1 μM cAMP) were each dissolved in newly prepared experimental buffer solution;
2. The PDE4B enzyme buffer solution was transferred into reaction wells;
3. The compound which was dissolved in 100% DMSO was added to the reaction wells containing PDE4B enzyme buffer solution by acoustic technique (echo 550; millilambda range) and the mixture was incubated for 10 minutes at room temperature;
4. The enzyme substrate buffer solution was added to the above reaction wells to initiate reaction;
5. The resulting mixture was incubated at room temperature for 1 hour;
6. The detection mixture (Transcreener®AMP2/GMP2 antibody and AMP2/GMP2 AlexaFluor633 tracer) was added to stop the reaction, and the resulting mixture was incubated for 90 minutes while slowly mixing. The measurement range of fluorescence polarization was Ex/Em=620/688.

Data analysis: the fluorescence polarization signal was converted to nM based on AMP/GMP standard curve and the percentage enzyme activity relative to DMSO control calculated by Excel. GraphPad Prism was used for curve fitting (drawing medical icon).

The experimental results are shown in Table 1:

TABLE 1

Results of in vitro screening test for compounds

| Compound | PDE3A IC$_{50}$(nM) | PDE4B IC$_{50}$(nM) |
|---|---|---|
| WX001 | 0.041 | 6.5 |
| WX002 | <0.02 | 5 |
| WX003 | 0.66 | 2.2 |
| WX004 | 0.63 | 0.12 |
| WX005 | 0.18 | 5.7 |
| WX010 | 0.65 | 9.8 |
| WX015 | 0.26 | 0.56 |
| WX016 | 0.01 | 0.24 |
| WX017 | 0.28 | 0.43 |
| WX018 | 0.28 | 0.05 |
| WX019 | 0.53 | 0.48 |
| WX020 | 0.65 | 0.47 |
| WX021 | 0.25 | 1.1 |
| WX024 | 0.04 | 0.04 |
| WX025 | 0.09 | 0.44 |
| WX026 | 0.01 | 2.5 |
| WX036 | 0.03 | 0.41 |
| WX037 | 0.51 | 1.7 |
| WX047 | 0.10 | 0.16 |
| WX048 | 0.03 | 0.27 |
| WX049 | 0.30 | 0.05 |
| WX050 | 1.1 | 0.24 |
| WX052 | 0.50 | 0.18 |
| WX053 | 0.57 | 1.9 |
| WX054 | 0.03 | 2.7 |
| WX055 | 0.04 | 2.1 |
| WX056 | 0.14 | 9.1 |
| WX057 | 0.31 | 5.4 |
| WX064 | 0.01 | 1.4 |

Experimental Example 3

In Vitro Detection of the Inhibitory Activity of Compounds Against TNF-α in Human Peripheral Blood Mononuclear Cells Experimental objective: to express the anti-inflammatory activity at the cellular level of the test compound based on the level of TNF-α in human peripheral blood mononuclear cells (hPBMCs).

Procedure:
1. Normal human whole blood was collected into an EDTA anticoagulation tube;
2. The PBMCs were separated by Ficoll density gradient centrifugation, and then counted. The cell concentration was adjusted to $2 \times 10^6$/mL;
3. To each well of a U-bottomed 96-well plate were added $2 \times 10^5$ cells, 1 ng/mL LPS, and DMSO solutions of compound at concentrations of 100 μM, 10 μM, 1 μM, 100 nM, 10 nM, 1 nM, 100 pM and 10 pM, 200 μL per well;
4. The mixture was incubated for 24 hours, and then the supernatant was collected;
5. The level of TNF-α in supernatant was detected by ELIZA, Graphpad Prism software was used to fit inhibition curves and IC$_{50}$ was calculated.

The experimental results are shown in Table 2:

TABLE 2

In vitro test results for compounds

| Compound | hPBMC IC$_{50}$(nM) |
|---|---|
| WX003 | 3.1 |
| WX004 | 0.33 |
| WX015 | 0.36 |
| WX016 | 2.8 |
| WX018 | 0.09 |
| WX047 | 0.25 |
| WX054 | 1.8 |

Experimental Example 4

Pharmacokinetic Experiment in Beagle Dogs

In this study, male beagle dogs were selected as test animals, and liquid chromatography-tandem mass spectrometry (LC-MS/MS) method was used for quantitatively measuring the drug concentration in plasma of beagle dogs at different time points after intravenous injection or oral administration of compound WX036 so as to evaluate the pharmacokinetic characteristics of the compound WX036 in beagle dogs.

The clear solution of compound WX036 was injected into two 10-12 kg beagle dogs via the cephalic vein or saphenous vein, and the clear solution of test compound was administered intragastrically to two 10-12 kg beagle dogs (overnight fasted). The animals were all subjected to approximately 500 μL of blood collection each time from peripheral veins at 0.0333, 0.0833, 0.25, 0.5, 1, 2, 4, 6, 8, and 24 hours post-dose, and the blood was transferred into commercial centrifuge tubes containing 0.85-1.15 mg of K$_2$ EDTA*2H$_2$O anticoagulant, and plasma was taken by centrifugation at 3000 g for 10 minutes at 4° C. The plasma concentration was measured by LC-MS/MS method, and the relevant pharmacokinetic parameters were calculated by WinNonlin™ Version 6.3 (Pharsight, Mountain View, CA) pharmacokinetic software using non-compartmental model linear logarithmic trapezoid method.

TABLE 3

Pharmacokinetic parameters of compound WX036 in beagle dogs

| Pharmacokinetic parameters in beagle dogs | Intravenous injection (0.5 mg/kg) | | | Oral administration (3 mg/kg) | | | |
|---|---|---|---|---|---|---|---|
| | Plasma clearance (mL/min/kg) | Half life (h) | Area under plasma concentration-time curve (0-inf, nM · h) | Peak concentration (nM) | Time to peak (h) | Area under plasma concentration-time curve (0-inf, nM · h) | Bioavailability (%) |
| WX036 | 70.3 | 0.3 | 210 | 59.4 | 0.6 | 123 | 7.5 |

Experimental Example 5

Inhibitory Effect on the Activity of Isoenzymes (CYP1A2, CYP2C9, CYP2C19, CYP2D6 and CYP3A4) of Human Liver Microsomal Cytochrome P450

A total of 5 specific probe substrates of 5 isoenzymes of CYP, namely phenacetin (CYP1A2), diclofenac (CYP2C9), (S)-mephenytoin (CYP2C19), dextromethorphan (CYP2D6) and midazolam (CYP3A4) are each co-incubated with human liver microsomes and test compound, and then reduced nicotinamide adenine dinucleotide phosphate (NADPH) was added to initiate the reaction. After the reaction was completed, samples were treated, and the concentrations of 5 metabolites (acetaminophen, 4'-hydroxydiclofenac, 4'-hydroxymephenytoin, dextrorphan and 1'-hydroxymidazolam) generated by the specific substrates were quantitatively detected by LC-MS/MS to calculate the corresponding half inhibitory concentrations ($IC_{50}$).

TABLE 4

| | Inhibition against five CYP enzymes by compounds WX026 and WX036 | | | | |
|---|---|---|---|---|---|
| Compound | $IC_{50}$ (μM) | | | | |
| number | CYP1A2 | CYP2C9 | CYP2C19 | CYP2D6 | CYP3A4 |
| WX026 | 50 | 20 | 50 | 50 | 16 |
| WX036 | 50 | 31 | 50 | 50 | 50 |

Experimental Example 6

Pharmacodynamic Study in Cigarette Smoke-Induced Rat Acute Lung Injury Model

Experimental Animals
Male Sprague-Dawley rats (supplied by Shanghai SLAC Laboratory Animal Co., Ltd.), SPF grade, approximately 200 g.

Experimental Procedure
1. Animals were randomly divided into 3 groups according to weight after one-week adaptive feed;
2. On days 1-3 of the experiment, the corresponding compound of each group was atomized for 30 minutes. Then the animals in the model group and each compound-treated group were exposed to cigarette smoke for 1 hour, and after a 4-hour interval, the animals were exposed to cigarette smoke again for 1 hour. Cigarette smoke was exposed twice daily for 3 consecutive days. Control animals were exposed to room air;
3. On day 4 of the experiment, the corresponding compound of each group was atomized for 30 minutes, and then the animals in the model group and each compound-treated group inhaled the atomized 150 μg/mL LPS for 15 minutes. Three hours later (from the time starting atomization), the animals were exposed to cigarette smoke for 1 hour, and then the lung function (Penh) of the animals was examined; bronchoalveolar lavage fluid (BALE) was collected for cell counting after the animals were euthanized with $CO_2$.
4. Administration
Administration mode: atomizing the test compound at the maximum atomization rate (approximately 12 mL) with the whole-body exposure atomization device for 30 minutes.

Administration frequency: atomizing the drug or solvent 30 minutes per day in the morning before exposure to cigarette smoke, and performing administration before the inhalation of the atomized LPS on day 4.

5. Measurements of pharmacodynamic endpoints
(1) Total white blood cells in BALF;
(2) Mch-induced detection of pulmonary function (airway resistance index Penh);

TABLE 5

| | Experimental groups | | |
|---|---|---|---|
| Group | Number of animals | Compound concentration of atomized solution | Time of administration |
| Model group | 10 | — | 30 minutes before the first cigarette smoke exposure every day |
| WX036 low dose group | 10 | 0.05 mg/mL | 30 minutes before the first cigarette smoke exposure every day |
| WX036 high dose group | 10 | 0.15 mg/mL | 30 minutes before the first cigarette smoke exposure every day |

Figure 2:
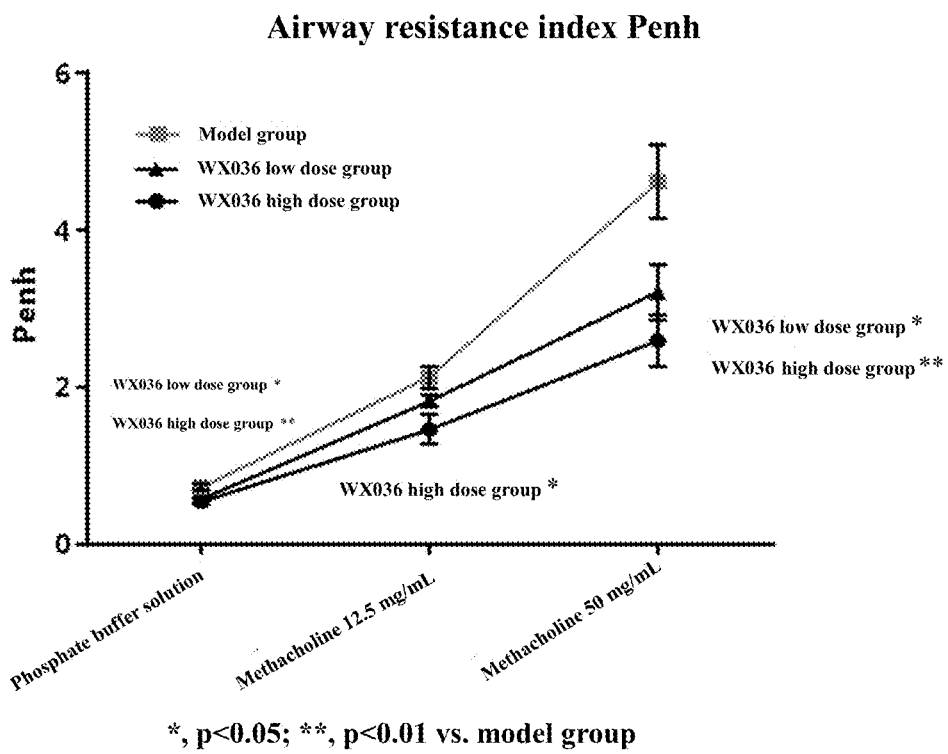
FIG. 2 shows the methacholine- (Mch-) induced detection of pulmonary function (airway resistance index Penh).

The experimental results are shown in FIG. 1 and FIG. 2.

What is claimed is:
1. A compound of formula (I), an isomer thereof or a pharmaceutically acceptable salt thereof,

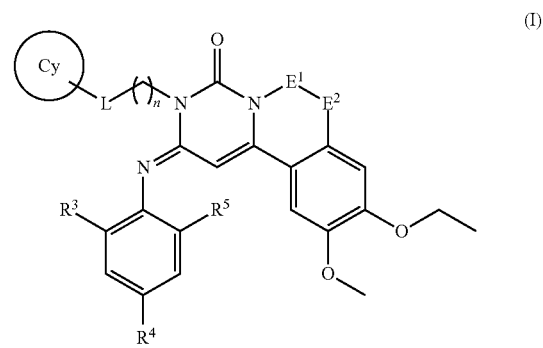

wherein,
a ring Cy is selected from the group consisting of 5-membered heterocyclyl and 5-membered heteroaryl, wherein the 5-membered heterocyclyl or 5-membered heteroaryl is optionally substituted by one or more of the following groups: amino, hydroxy, =O, halogen, cyano, $C_{1-12}$ alkyl, —C(O)NH$_2$, —C(O)NH($C_{1-6}$ alkyl), —C(O)N($C_{1-6}$ alkyl)$_2$, —COOH, —C(O)O ($C_{1-6}$ alkyl) or $C_{1-12}$ alkoxy, wherein the $C_{1-12}$ alkyl or $C_{1-12}$ alkoxy is optionally substituted by one or more groups selected from the group consisting of halogen, amino and hydroxy;
ring atoms of the ring Cy comprise at least one nitrogen atom;
L is selected from the group consisting of —N(R$^6$)—, —N(R$^6$)C(O)—, —C(O)N(R$^6$)—, —O—, —S—, —OC(O)—, —C(O)O—, —CH$_2$N(R$^6$)C(O)—, —CH$_2$C(O)N(R$^6$)—, —S(O)$_2$NH—, —NHS(O)$_2$— and a single bond;
n is 1, 2, 3 or 4;
E$^1$ is —(CH$_2$)$_m$—, wherein m is 1, 2 or 3;
E$^2$ is selected from the group consisting of —O—, —NH—, —S— and a single bond;

R³, R⁴ and R⁵ are each independently selected from the group consisting of hydrogen, halogen and $C_{1-6}$ alkyl, wherein the $C_{1-6}$ alkyl is optionally substituted by one or more groups selected from the group consisting of halogen, amino and hydroxy; and each R⁶ is independently selected from the group consisting of hydrogen, hydroxy and $C_{1-3}$ alkyl, wherein the $C_{1-3}$ alkyl is optionally substituted by one or more groups selected from the group consisting of halogen, amino and hydroxy.

2. The compound of formula (I), the isomer thereof or the pharmaceutically acceptable salt thereof according to claim 1, wherein the ring Cy is selected from the group consisting of 5-membered heterocyclyl and 5-membered heteroaryl, wherein the 5-membered heterocyclyl or 5-membered heteroaryl is optionally substituted by one or more of the following groups: amino, hydroxy, =O, halogen, cyano, $C_{1-6}$alkyl, —C(O)NH₂, —C(O)NH($C_{1-3}$ alkyl), —C(O)N($C_{1-3}$ alkyl)₂, —COOH, —C(O)O($C_{1-3}$ alkyl), $C_{1-6}$ alkoxy, or $C_{1-6}$ alkyl substituted by one or more halogens.

3. The compound of formula (I), the isomer thereof or the pharmaceutically acceptable salt thereof according to claim 1, wherein the ring Cy is selected from the group consisting of structural units

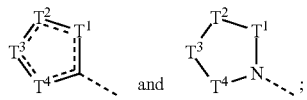

wherein

⫽ represents a single bond or double bond;

T¹, T², T³ and T⁴ are each independently selected from the group consisting of C=O, C(R¹), C(R¹)₂, O, N(R²), N and S;

each R¹ is independently selected from the group consisting of hydrogen, amino, hydroxy, halogen, cyano, $C_{1-12}$ alkyl, —C(O)NH₂, —C(O)NH($C_{1-6}$ alkyl), —C(O)N($C_{1-6}$ alkyl)₂, —COOH, —C(O)O($C_{1-6}$ alkyl) and $C_{1-12}$ alkoxy, wherein the $C_{1-12}$ alkyl or $C_{1-12}$ alkoxy is optionally substituted by one or more groups selected from the group consisting of halogen, amino and hydroxy;

each R² is independently selected from the group consisting of hydrogen, hydroxy and $C_{1-3}$ alkyl, wherein the $C_{1-3}$ alkyl is optionally substituted by one or more groups selected from the group consisting of halogen, amino and hydroxyl.

4. The compound of formula (I), the isomer thereof or the pharmaceutically acceptable salt thereof according to claim 3, wherein the structural unit

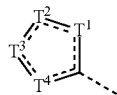

is selected from the group consisting of

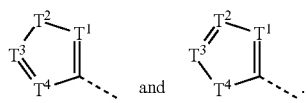

5. The compound of formula (I), the isomer thereof or the pharmaceutically acceptable salt thereof according to claim 1, wherein L is selected from the group consisting of —N(R⁶)—, —N(R⁶)C(O)—, —C(O)N(R⁶)—, —CH₂N(R⁶)C(O)—, —CH₂C(O)N(R⁶)—, —S(O)₂NH—, —NHS(O)₂— and a single bond.

6. The compound of formula (I), the isomer thereof or the pharmaceutically acceptable salt thereof according to claim 1, wherein n is selected from the group consisting of 1, 2 and 3.

7. The compound of formula (I), the isomer thereof or the pharmaceutically acceptable salt thereof according to claim 1, wherein R³, R⁴ and R⁵ are each independently selected from the group consisting of halogen and $C_{1-3}$ alkyl, wherein the $C_{1-3}$ alkyl is optionally substituted by 1, 2 or 3 halogens, amino or hydroxyl.

8. The compound of formula (I), the isomer thereof or the pharmaceutically acceptable salt thereof according to claim 1, wherein each R⁶ is independently selected from the group consisting of hydrogen, hydroxy and methyl, wherein the methyl is optionally substituted by 1, 2 or 3 halogens, amino or hydroxyl.

9. The compound of formula (I), the isomer thereof or the pharmaceutically acceptable salt thereof according to claim 1, wherein E¹ is selected from the group consisting of —(CH₂)₂— and —(CH₂)₃—.

10. The compound of formula (I), the isomer thereof or the pharmaceutically acceptable salt thereof according to claim 1, wherein E² is selected from the group consisting of —O— and a bond.

11. The compound of formula (I), the isomer thereof or the pharmaceutically acceptable salt thereof according to claim 3, wherein the compound of formula (I) is a compound of formula (II)

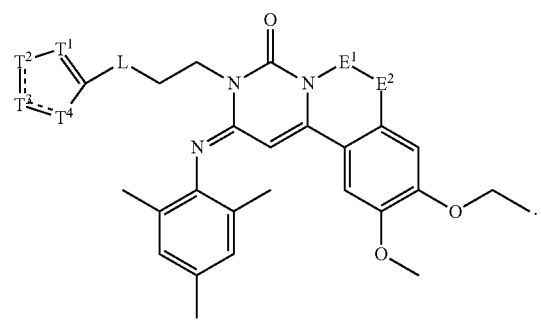

12. The compound of formula (I), the isomer thereof or the pharmaceutically acceptable salt thereof according to claim 1, wherein the compound selected from

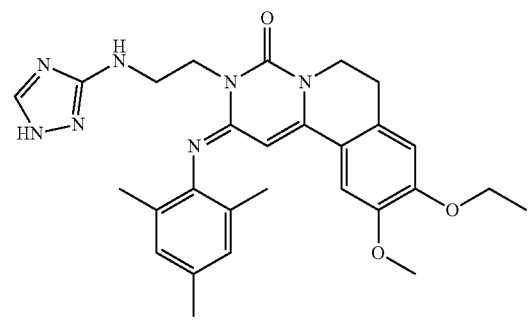

117
-continued
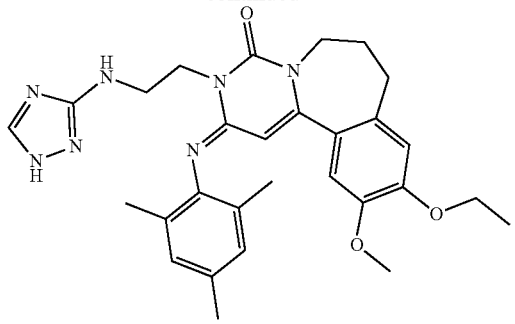
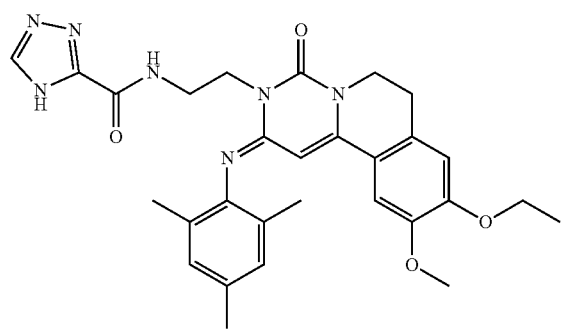
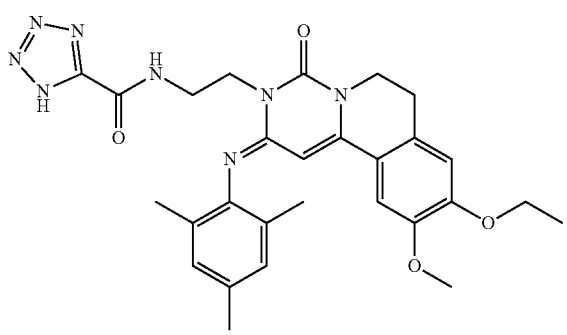
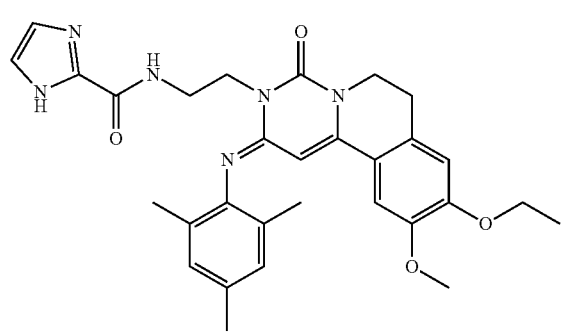
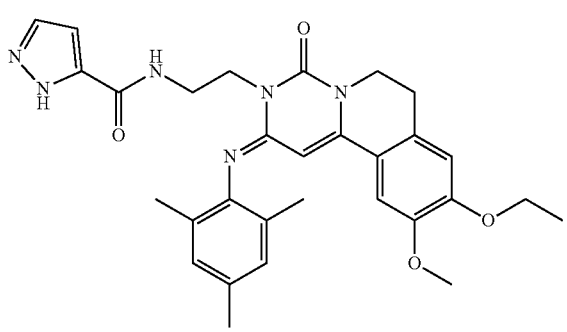
118
-continued
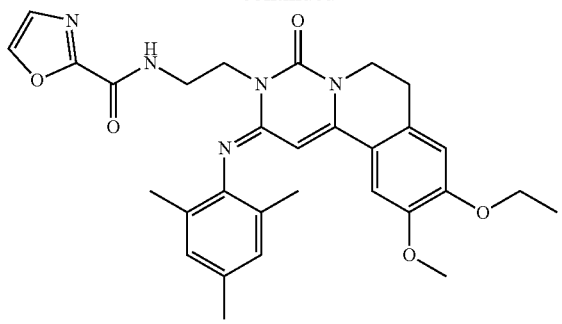
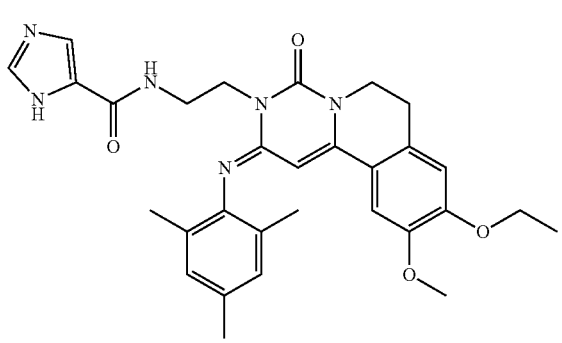
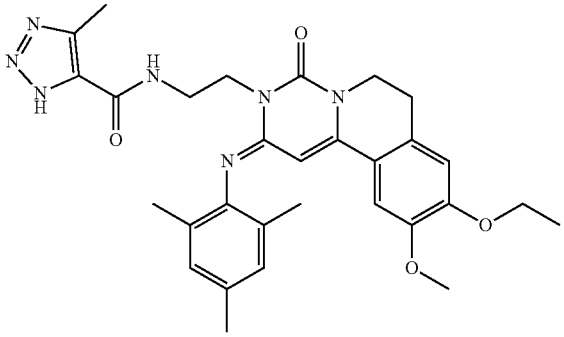
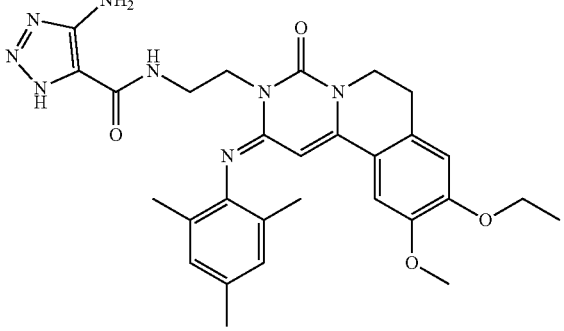

119
-continued
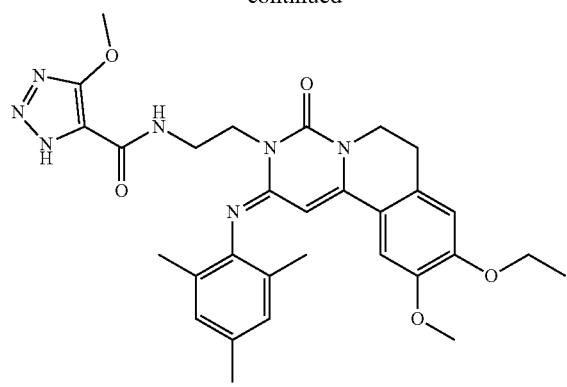
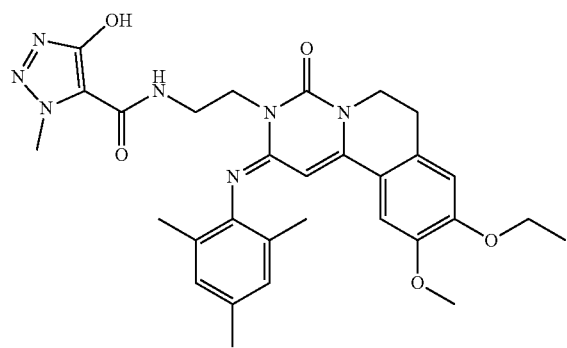
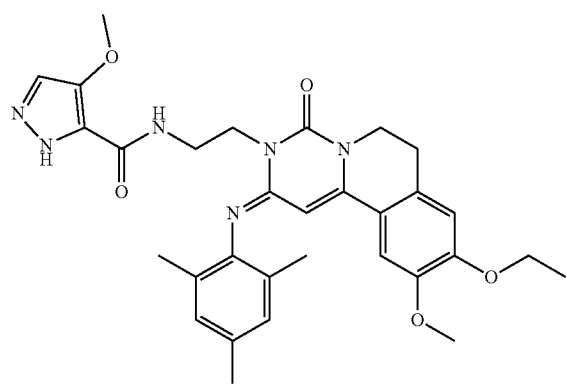
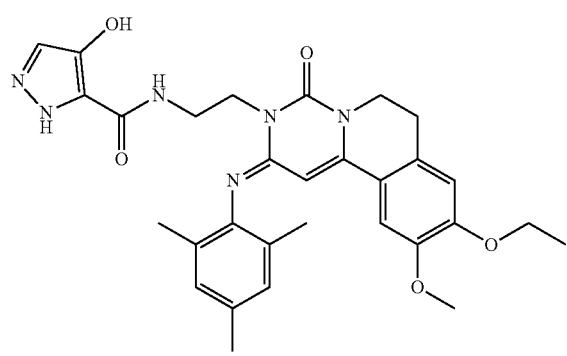
120
-continued
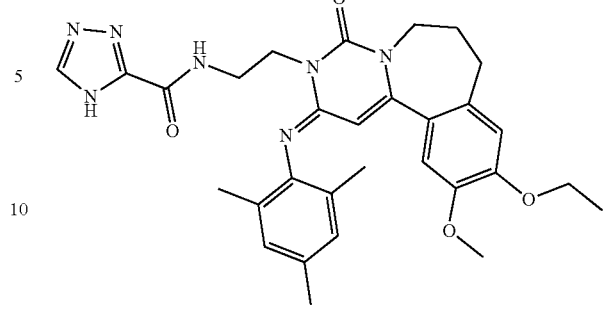
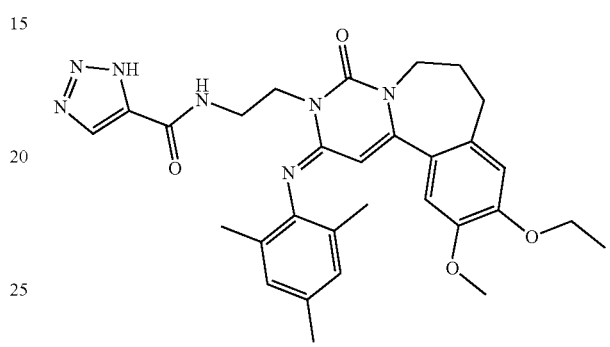
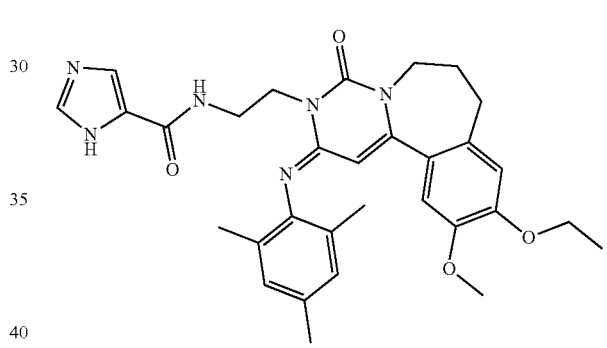
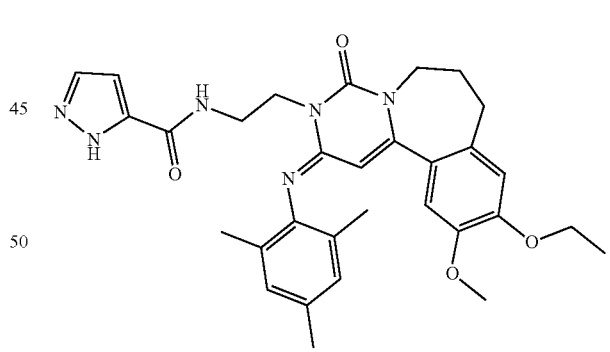
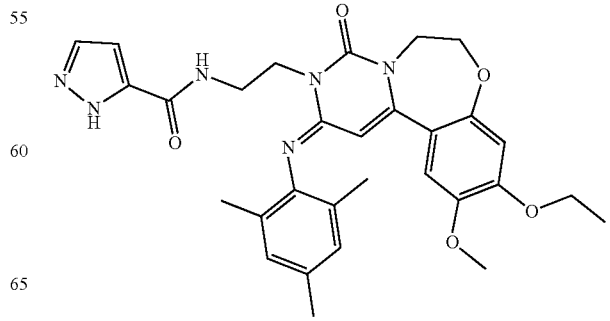

121
-continued
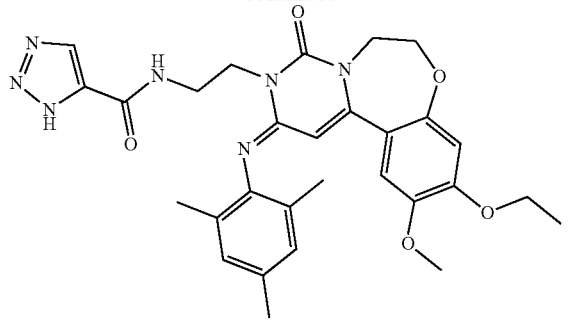
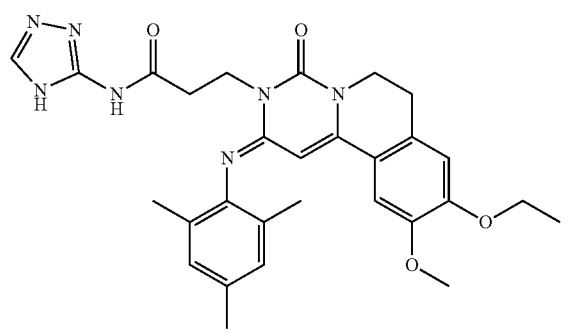
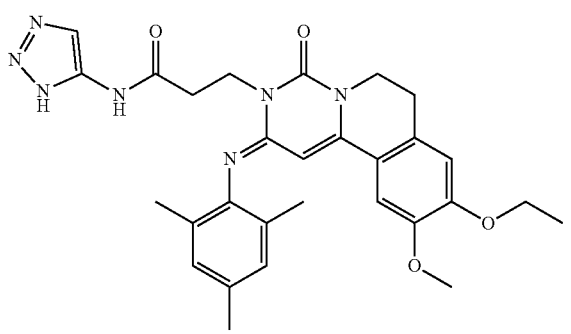 [SMILES: CCOc1cc2c(cc1OC)-c1c/c(=N\c3c(C)cc(C)cc3C)n(CCC(=O)Nc3cnn[nH]3)c(=O)n1CC2]
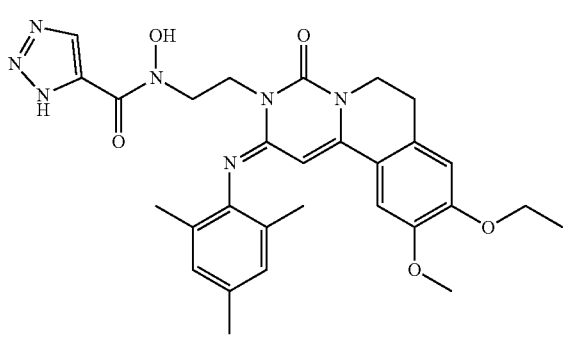
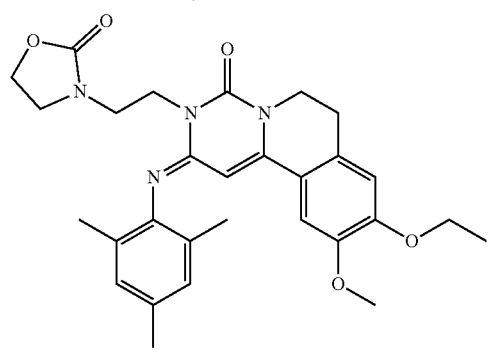
122
-continued
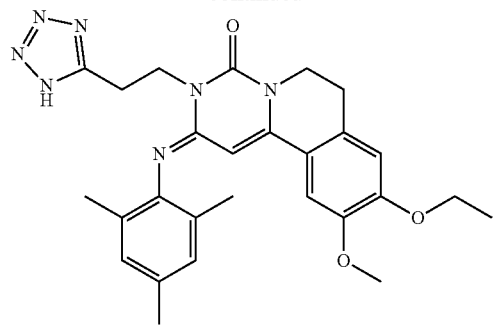
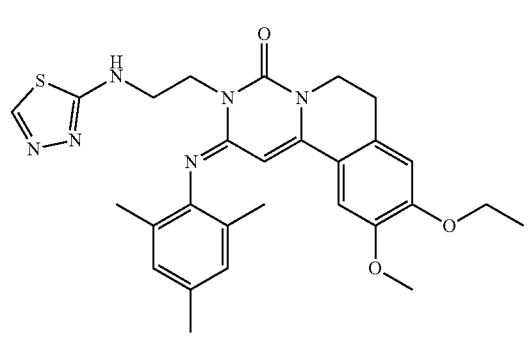
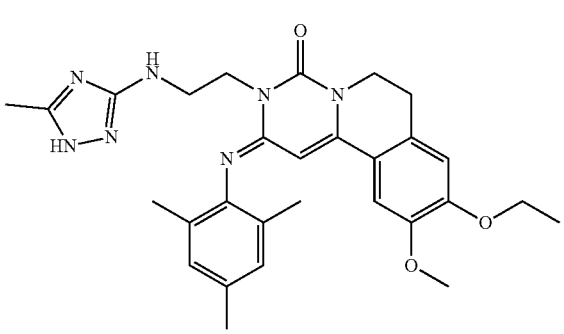
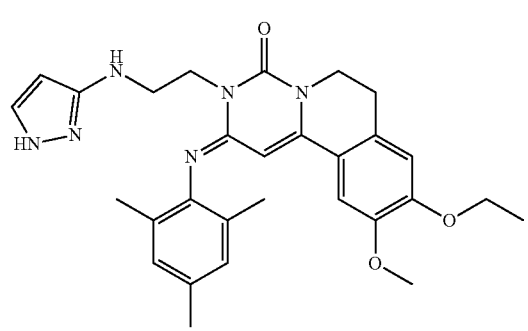
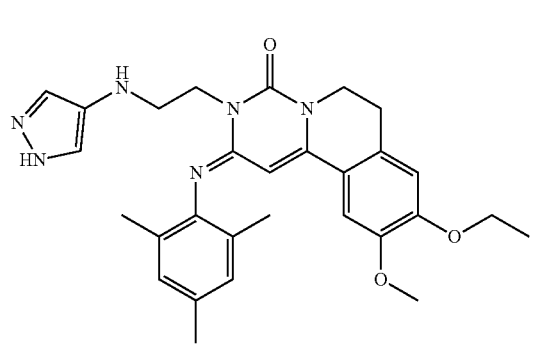

123
-continued
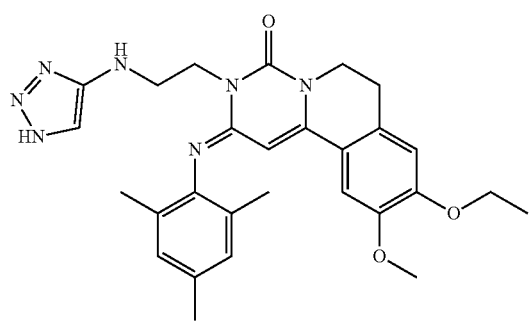
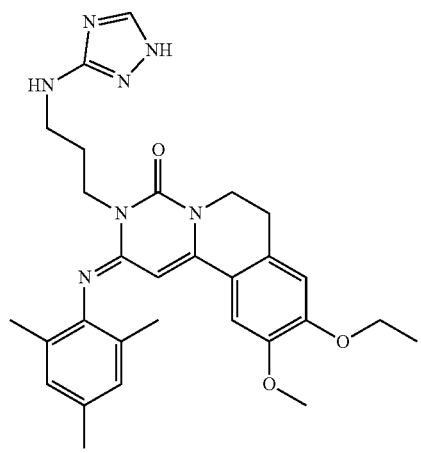
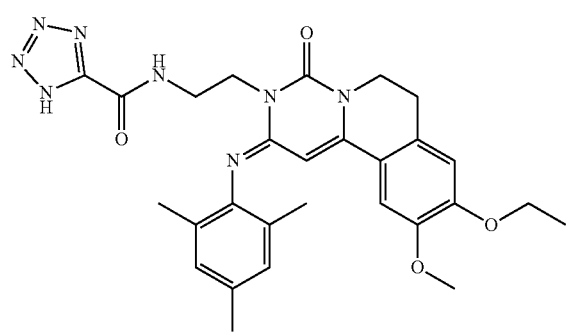
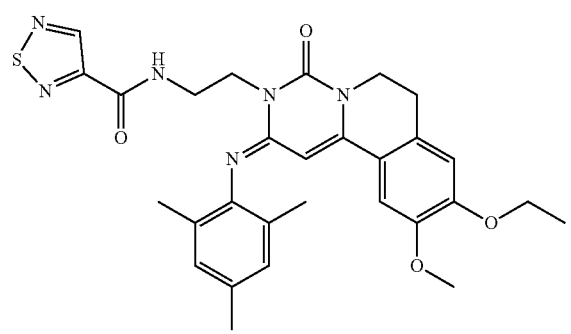
124
-continued
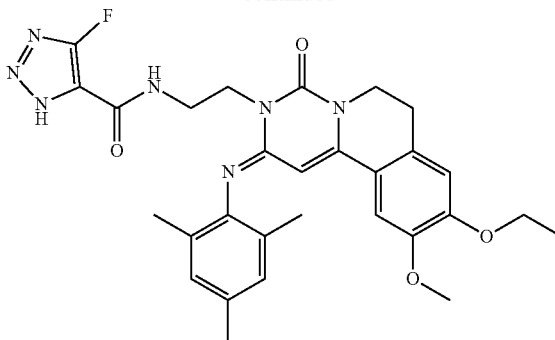
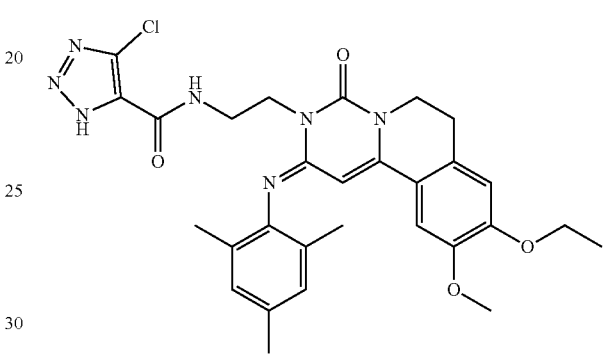
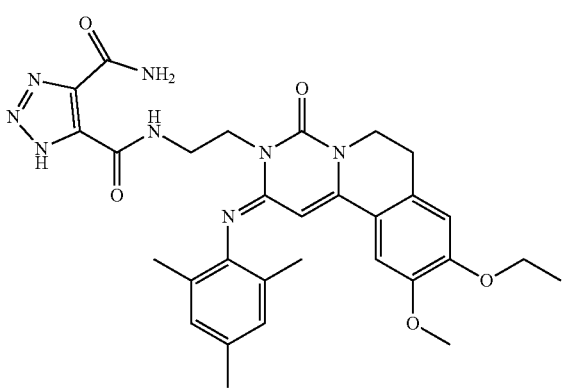

125
-continued
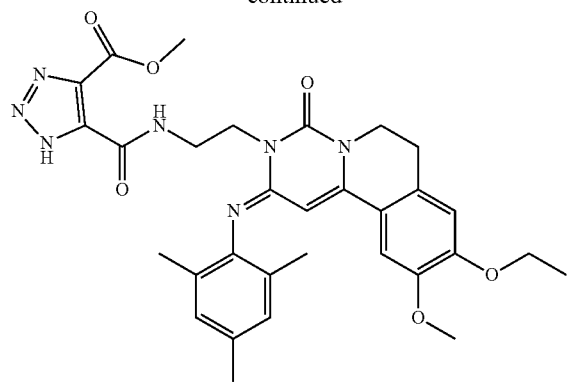
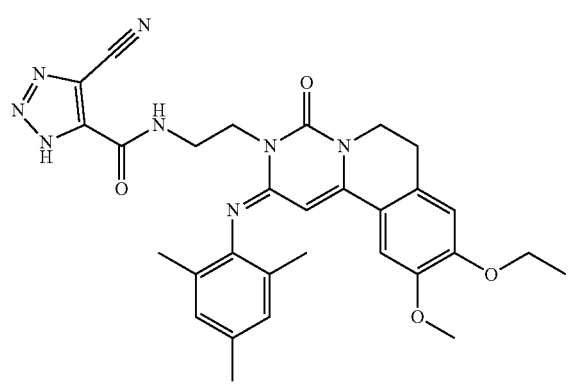
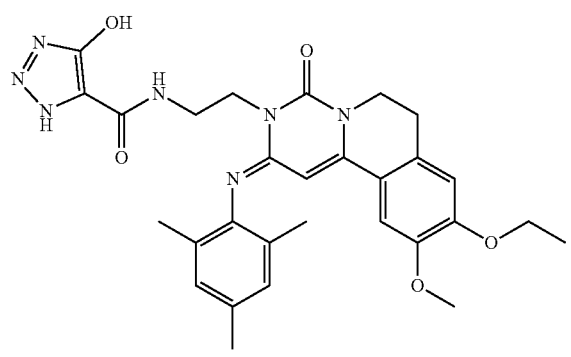
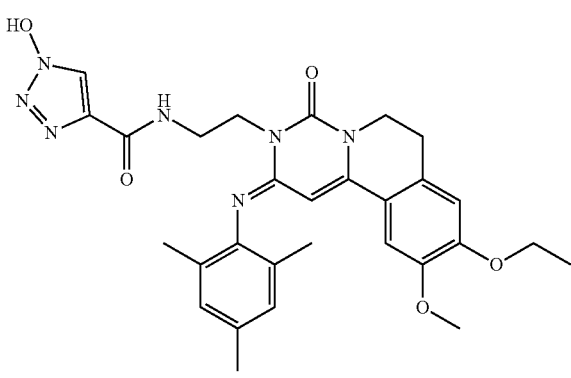
126
-continued
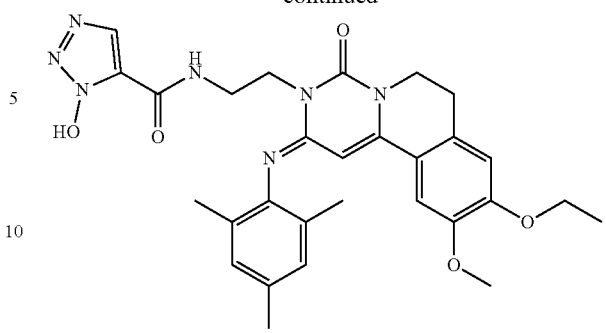
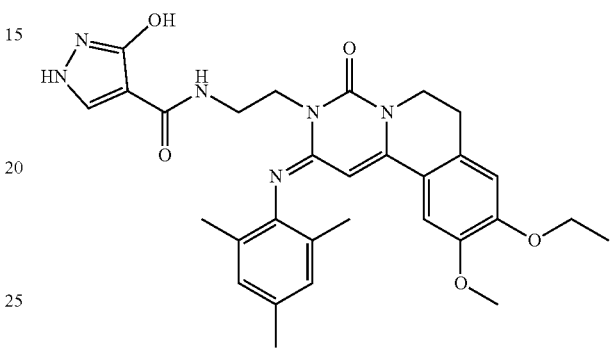
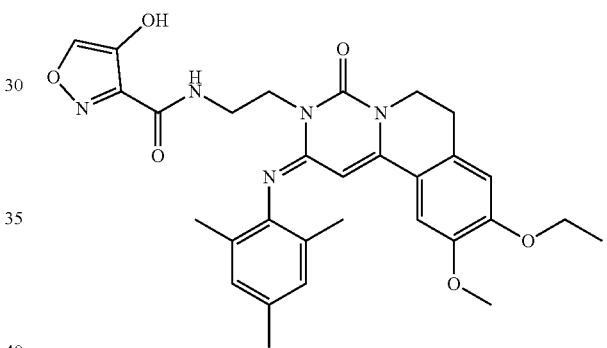
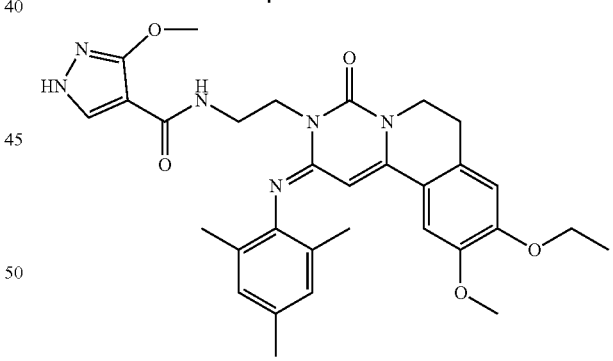
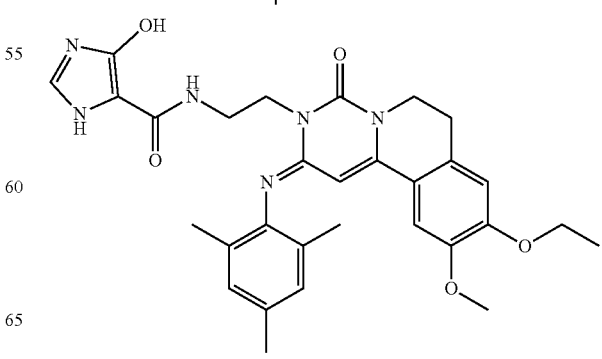

127
-continued
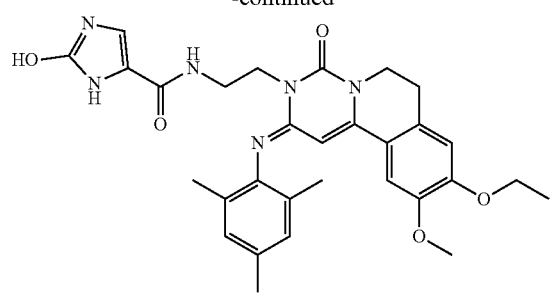
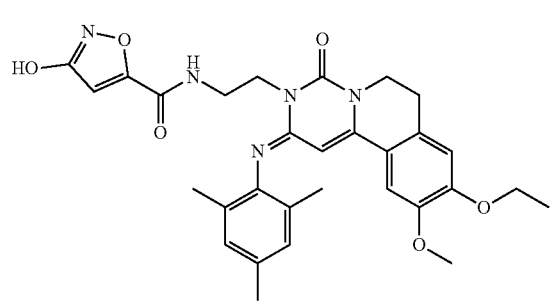
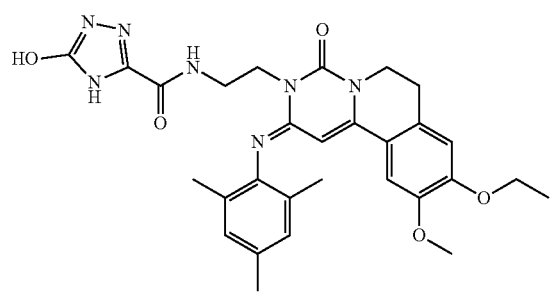
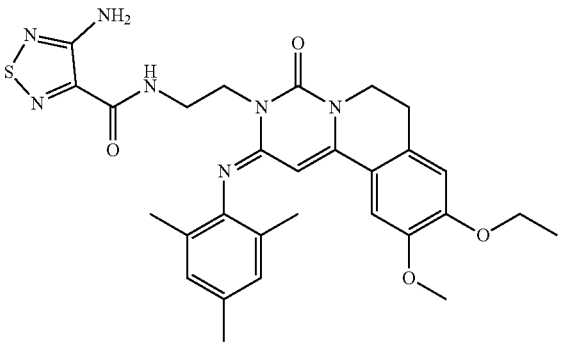
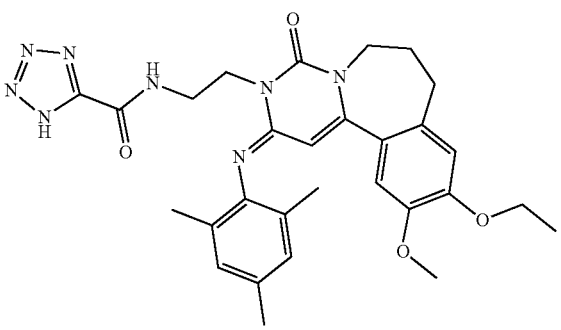
128
-continued
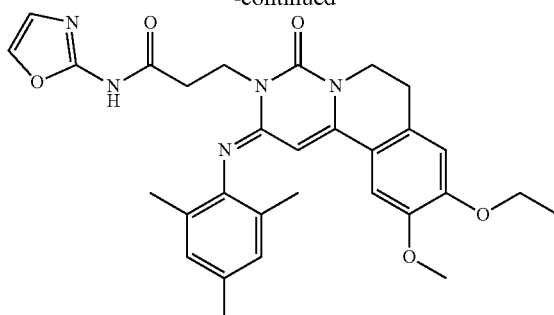
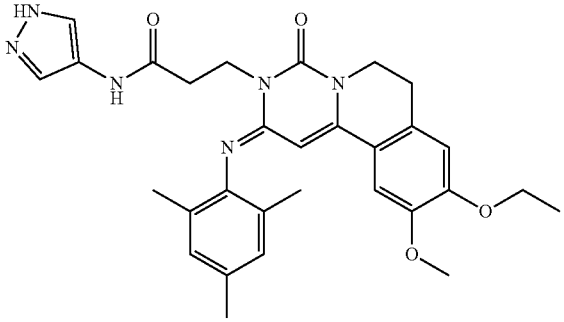 [SMILES: CCOc1cc2c(cc1OC)-c1c/c(=N\c3c(C)cc(C)cc3C)n(CCC(=O)Nc3cn[nH]c3)c(=O)n1CC2]
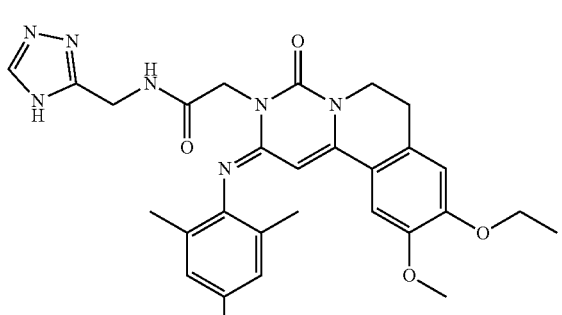
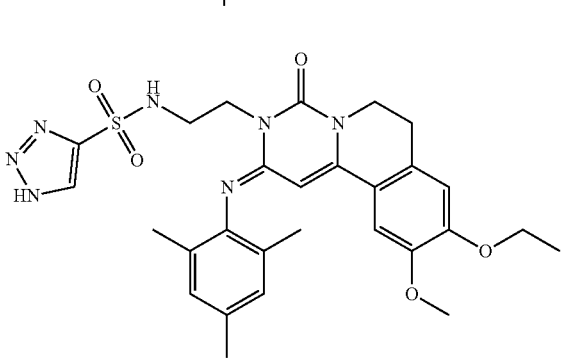
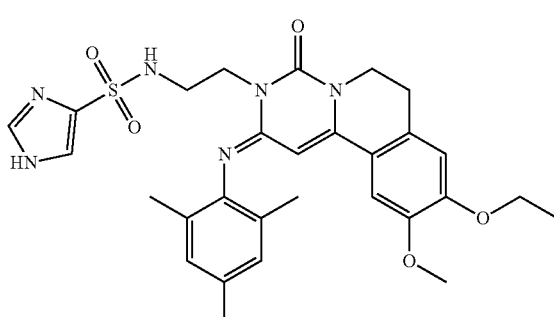

-continued

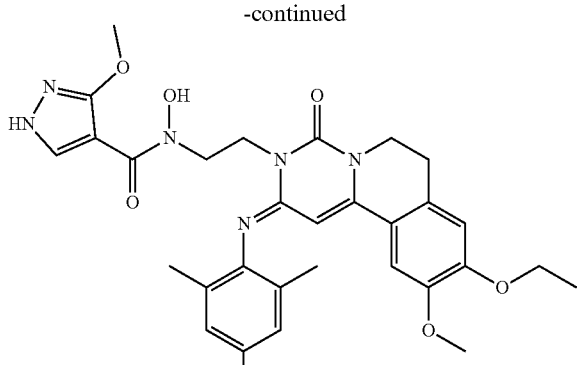

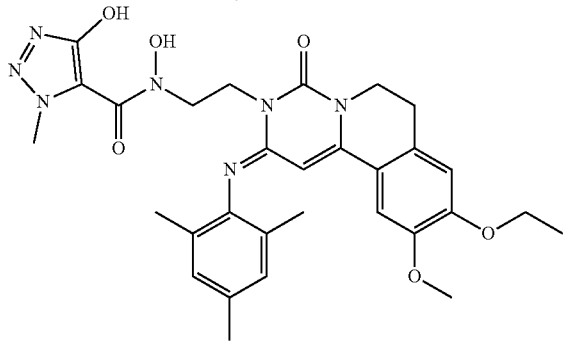

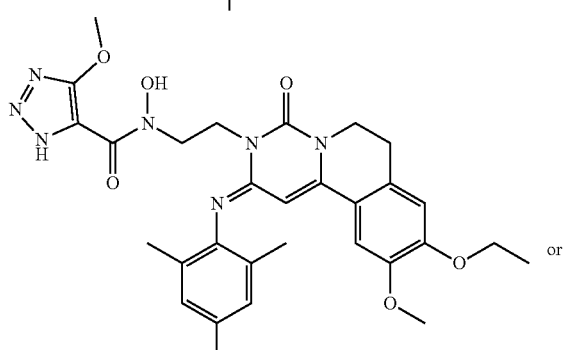 or

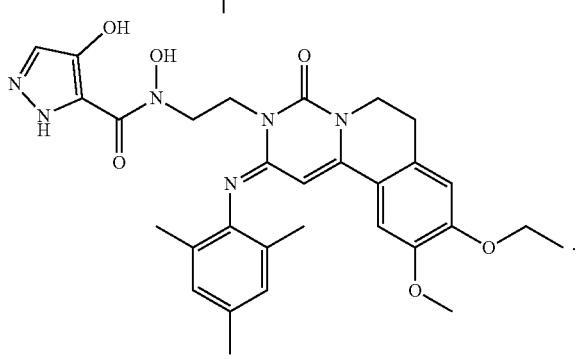

13. A pharmaceutical composition comprising the compound, the isomer thereof or the pharmaceutically acceptable salt thereof according to claim 1 and a pharmaceutically acceptable excipient, carrier or diluent.

14. A method for treating a disease related to PDE3 and/or PDE4 in a mammal, the disease being asthma or COPD, comprising administering to the mammal in need thereof a therapeutically effective amount of the compound, the isomer thereof or the pharmaceutically acceptable salt thereof according to claim 1.

15. The compound of formula (I), the isomer thereof or the pharmaceutically acceptable salt thereof according to claim 2, wherein the ring Cy is selected from the group consisting of 5-membered heterocyclyl and 5-membered heteroaryl, wherein the 5-membered heteroaryl is optionally substituted by one or more of the following groups: amino, hydroxy, $C_{1-6}$ alkyl, $C_{1-6}$ alkoxy, wherein the 5-membered heterocyclyl is optionally substituted by one or more =O.

16. The compound of formula (I), the isomer thereof or the pharmaceutically acceptable salt thereof according to claim 2, wherein the ring Cy is selected from the group consisting of oxazolidin-2-one, imidazolyl, pyrazolyl, oxazolyl, triazolyl, oxadiazolyl, tetrazolyl, thiadiazolyl and isoxazolyl, wherein the imidazolyl, pyrazolyl, oxazolyl, triazolyl, oxadiazolyl, tetrazolyl, thiadiazolyl or isoxazolyl is optionally substituted by one or more of the following groups: amino, hydroxy, halogen, cyano, $C_{1-6}$ alkyl, —C(O)NH$_2$, —C(O)NH($C_{1-3}$ alkyl), —C(O)N($C_{1-3}$ alkyl)$_2$, —COOH, —C(O)O($C_{1-3}$ alkyl), $C_{1-6}$ alkoxy, or $C_{1-6}$ alkyl substituted by one or more halogens.

17. The compound of formula (I), the isomer thereof or the pharmaceutically acceptable salt thereof according to claim 3, wherein $T^1$ is selected from the group consisting of $C(R^1)$, $C(R^1)_2$ and N, and $T^2$, $T^3$ and $T^4$ are each independently selected from the group consisting of C=O, $C(R^1)$, $C(R^1)_2$, O, $N(R^2)$, N and S; each $R^1$ is independently selected from the group consisting of hydrogen, amino, hydroxy, halogen, cyano, $C_{1-6}$ alkyl, —C(O)NH$_2$, —C(O)NH($C_{1-3}$ alkyl), —C(O)N($C_{1-3}$ alkyl)$_2$, —COOH, —C(O)O($C_{1-3}$ alkyl) and $C_{1-6}$ alkoxy, wherein the $C_{1-6}$ alkyl or $C_{1-6}$ alkoxy is optionally substituted by one or more groups selected from the group consisting of halogen, amino and hydroxyl; and each $R^2$ is independently selected from the group consisting of hydrogen, hydroxy and $C_{1-3}$ alkyl, wherein the $C_{1-3}$ alkyl is optionally substituted by 1, 2 or 3 halogens, amino or hydroxyl.

18. The compound of formula (I), the isomer thereof or the pharmaceutically acceptable salt thereof according to claim 4, wherein the structural unit

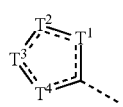

is selected from the group consisting of

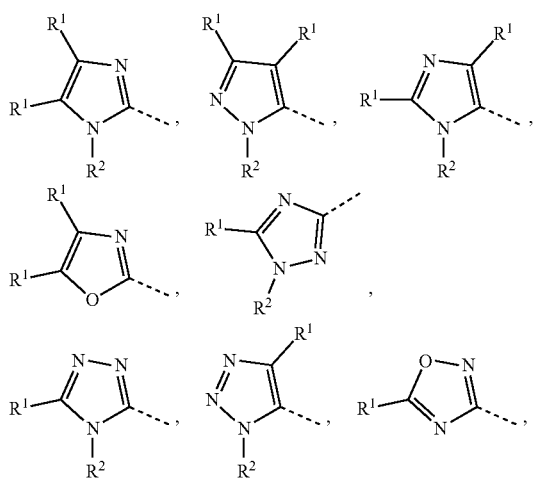

131

-continued

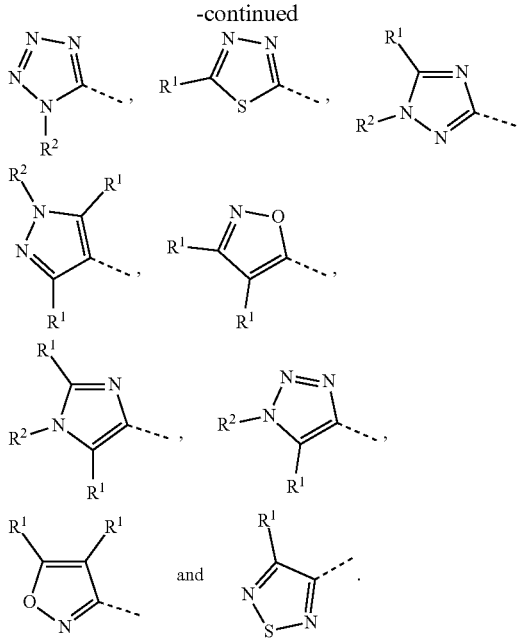

19. The compound of formula (I), the isomer thereof or the pharmaceutically acceptable salt thereof according to claim 4, wherein the structural unit

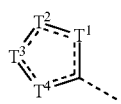

is selected from the group consisting of

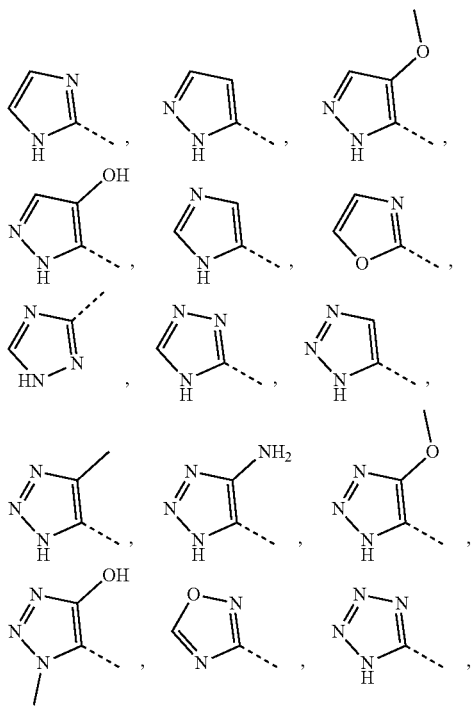

132

-continued

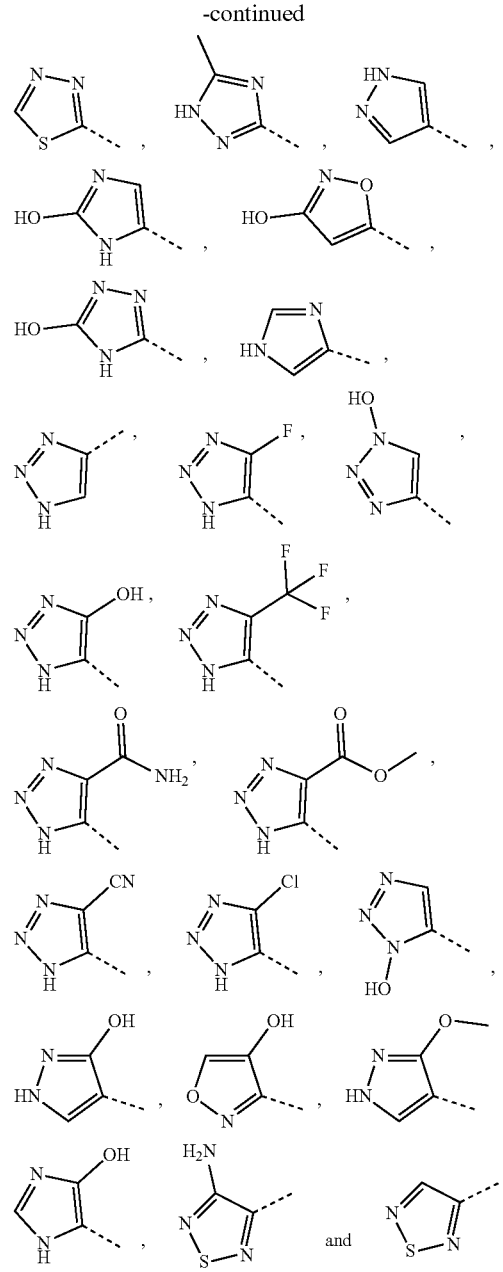

20. The compound of formula (I), the isomer thereof or the pharmaceutically acceptable salt thereof according to claim 1, wherein L is selected from the group consisting of —N(R$^6$)—, —N(R$^6$)C(O)—, —C(O)N(R$^6$)—, —CH$_2$N (R$^6$)C(O)—, —CH$_2$C(O)N(R$^6$)— and a single bond.

21. The compound of formula (I), the isomer thereof or the pharmaceutically acceptable salt thereof according to claim 1, wherein the ring Cy is selected from the group consisting of structural units

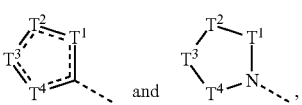

the structural unit

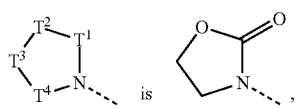 is and the structural unit

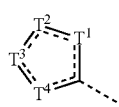

is selected from the group consisting of

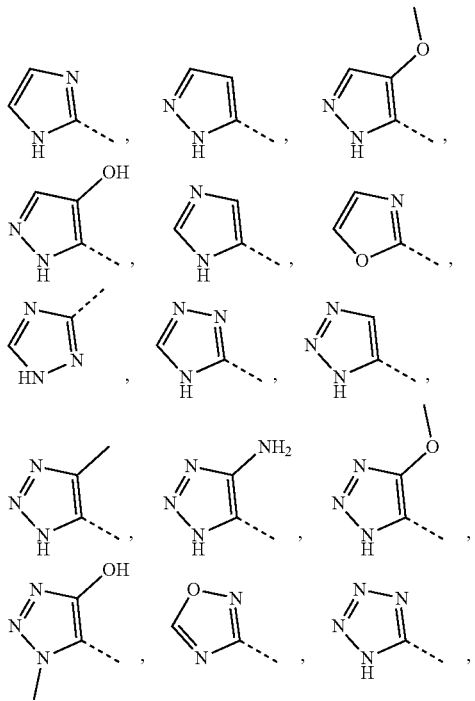

-continued

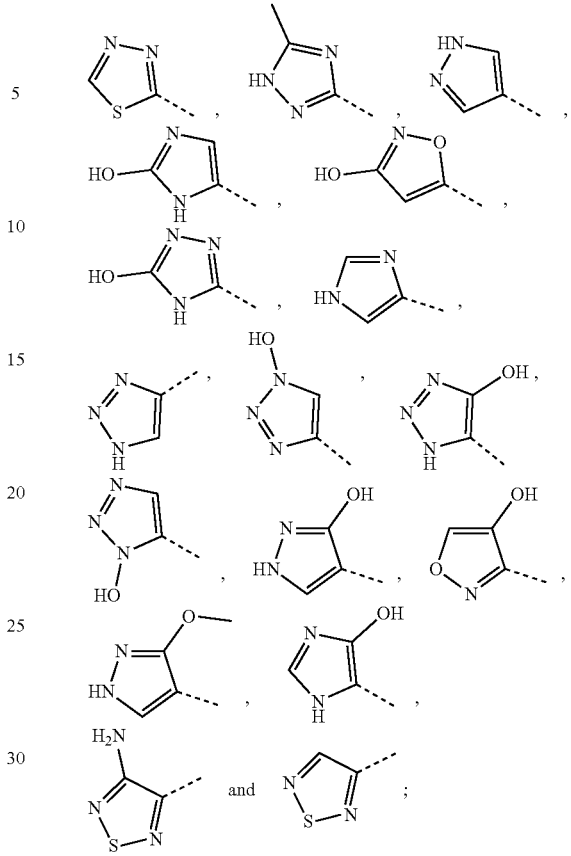

L is selected from the group consisting of —N(R$^6$)—, —N(R$^6$)C(O)—, —C(O)N(R$^6$)—, —CH$_2$N(R$^6$)C(O)—, —CH$_2$C(O)N(R$^6$)— and a single bond;

n is selected from the group consisting of 1, 2 and 3;

E$^1$ is —(CH$_2$)$_m$—, wherein m is 2 or 3;

E$^2$ is —O— or a single bond;

R$^3$, R$^4$ and R$^5$ are each independently C$_{1-3}$ alkyl; and each R$^6$ is independently selected from the group consisting of hydrogen and hydroxyl.

* * * * *

UNITED STATES PATENT AND TRADEMARK OFFICE
CERTIFICATE OF CORRECTION

PATENT NO. : 11,993,596 B2
APPLICATION NO. : 17/259089
DATED : May 28, 2024
INVENTOR(S) : Luo et al.

Page 1 of 1

It is certified that error appears in the above-identified patent and that said Letters Patent is hereby corrected as shown below:

In the Claims

At Column 117, Lines 27-40 (Claim 12), please delete " 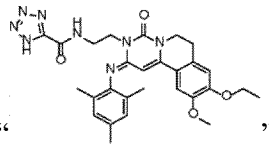 " and insert --  -- therefor.

Signed and Sealed this
First Day of October, 2024

Katherine Kelly Vidal
*Director of the United States Patent and Trademark Office*